United States Patent
Yu et al.

(10) Patent No.: US 8,859,851 B2
(45) Date of Patent: Oct. 14, 2014

(54) COLD-TOLERANT PLANTS EXPRESSING MYBS3 AND DREB1A PROTEINS

(75) Inventors: Su-May Yu, Taipei (TW); Chin-Fen Su, Kaohsiung (TW)

(73) Assignee: Academia Sinica, Taipei (TW)

( * ) Notice: Subject to any disclaimer, the term of this patent is extended or adjusted under 35 U.S.C. 154(b) by 513 days.

(21) Appl. No.: 13/197,187

(22) Filed: Aug. 3, 2011

(65) Prior Publication Data
US 2012/0036597 A1    Feb. 9, 2012

Related U.S. Application Data

(60) Provisional application No. 61/370,351, filed on Aug. 3, 2010.

(51) Int. Cl.
C12N 15/67    (2006.01)
C12N 15/82    (2006.01)
C07K 14/415    (2006.01)

(52) U.S. Cl.
CPC ................................. C12N 15/8273 (2013.01)
USPC ......... 800/289; 800/298; 800/320.2; 800/278

(58) Field of Classification Search
None
See application file for complete search history.

(56) References Cited

U.S. PATENT DOCUMENTS 7,291,768 B2    11/2007   Yu
2004/0107456 A1*   6/2004   Yu ................................ 800/278
2006/0225154 A1*  10/2006   Kasukabe et al. ............ 800/289

OTHER PUBLICATIONS

Su et al. A novel MYBS3-dependent pathway confers cold tolerance in rice. Plant Physiology. 2010. 153: 145-158.*
Cai et al.; "Identification of a MYB3R Gene Involved in Drought, Salt and Cold Stress in Wheat (*Triticum aestivum* L.)"; Gene; 485:146-152 (2011).
Zhai et al.; "A Single-Repeat R-3-MYB Transcription Factor MYBC1 Negatively Regulates Freezing Tolerance in *Arabidopsis*"; Biochemical and Biophysical Research Communications; 394:1018-1023 (2010).

* cited by examiner

*Primary Examiner* — Brent T Page
*Assistant Examiner* — Ashley K Buran
(74) *Attorney, Agent, or Firm* — Cesari and McKenna, LLP

(57) ABSTRACT

Disclosed are chill- or cold-tolerant plants and methods of making the plants. Also disclosed are methods for identifying a plant that is tolerant to chill.

6 Claims, 6 Drawing Sheets

Figure 5

```
GRMZM2G034   : ------------------*------------- :   -
sb01g02902   : ------------------------------- :   -
At3g1635     : ------------------------------- :   -
chr2.CM002   : ------------------A------------ : 308
sb03g00327   : ------------------------------- :   -
Glyma17g15   : ------------------------------- :   -
Glyma05g04   : ------------------------------- :   -
LjT37H17.8   : ------------------------------- :   -
GSVIVT0001   : ------------------------------- :   -
GSVIVT0001   : ------------NGKILLVWRL---------- : 345
At5g47390    : ------------------------------- :   -
OsMYBS3      : ------------------------------- :   -
GRMZM2G020   : ------------------------------- :   -
```

Figure 5 (conti.)

COLD-TOLERANT PLANTS EXPRESSING MYBS3 AND DREB1A PROTEINS

RELATED APPLICATION

This application claims priority of U.S. Provisional Application No. 61/370,351, filed on Aug. 3, 2010. The prior application is incorporated herein by reference in its entirety.

BACKGROUND

Various plants, including most important food crops, are not tolerant to cold. For example, rice seedlings are particularly sensitive to chilling in early spring in temperate and subtropical zones and in high elevation areas. Improvement of chilling tolerance in rice or other food crops may significantly increase their production. There is a need for cold-tolerant plants.

SUMMARY

This invention relates to using transgenic technology to generate cold-tolerant plants.

Accordingly, one aspect of this invention features a transgenic plant having a cell that has a MYBS3 gene expression level that is higher than a wild type MYBS3 protein level. Listed below is polypeptide sequence (SEQ ID NO: 1) and the nucleic acid sequence (SEQ ID NO: 2) of rice OsMybS3:

```
    1 ATCGATCGATCGATCTCCATAGGTGGGGGAAGGGAAGCTTTGGAAGGTGGAGGGACGGAG*(SEQ ID NO: 1)
   61 GGGGGGATGACGAGGCGGTGCTCGCACTGCAGCCACAACGGGCACAACTCGCGGACGTGC
              M   T   R   R   C   S   H   C   S   H   N   G   H   N   S   R   T   C
  121 CCCAACCGCGGGGTCAAGATCTTCGGGGTGCGCCTCACCGATGGCTCCATCCGCAAGAGC
          P   N   R   G   V   K   I   F   G   V   R   L   T   D   G   S   I   R   K   S
  181 GCCAGCATGGGGAACCTCTCCCTCCTCTCCTCCGCCGCCGGATCCACCAGCGGCGGCGCC
          A   S   M   G   N   L   S   L   L   S   S   A   A   G   S   T   S   G   G   A
  241 TCCCCCGCCGACGGCCCCGACGCCGCCCCACCGCCGCCGACGGCTACGCCTCCGACGAC
          S   P   A   D   G   P   D   A   A   P   T   A   A   D   G   Y   A   S   D   D
  301 TTCGTCCAGGGCTTCTCCTCCGCCACCCGCGACCGCAAGAAGGGTGTTCCTTGGACTGAA
          F   V   Q   G   F   S   S   A   T   R   D   R   K   K   G   V   P   W   T   E
  361 GAAGAACACCGGAGGTTTTTGCTTGGATTGCAAAAGCTTGGCAAAGGTGATTGGCGAGGA
          E   E   H   R   R   F   L   L   G   L   Q   K   L   G   K   G   D   W   R   G
  421 ATCTCTCGTAATTTCGTGGTCTCAAGAACACCTACTCAAGTAGCCAGTCATGCTCAGAAA
          I   S   R   N   F   V   V   S   R   T   P   T   Q   V   A   S   H   A   Q   K
  481 TATTTTATACGCCAATCCAATATGACCAGAAGGAAAAGAAGGTCTAGCCTTTTTGACATG
          Y   F   I   R   Q   S   N   M   T   R   R   K   R   R   S   S   L   F   D   M
  541 GTGCCAGATGAGTCTATGGACCTTCCACCACTTCCTGGAGGTCAAGAACCAGAGACCCAA
          V   P   D   E   S   M   D   L   P   P   L   P   G   G   Q   E   P   E   T   Q
  601 GTATTAAATCAACCAGCACTACCTCCACCGAAGGAGGAAGAGGAGGTAGATTCTATGGAG
          V   L   N   Q   P   A   L   P   P   P   K   E   E   E   E   V   D   S   M   E
  661 TCAGATACTTCTGCCGTTGCAGAGAGCTCTTCCGCTTCTGCTATCATGCCAGATAATTTG
          S   D   T   S   A   V   A   E   S   S   S   A   S   A   I   M   P   D   N   L
  721 CAGTCGACCTATCCAGTGATTGTTCCAGCTTATTTCTCGCCCTTTTTGCAATTCTCGGTT
          Q   S   T   Y   P   V   I   V   P   A   Y   F   S   P   F   L   Q   F   S   V
  781 CCTTTCTGGCAAAATCAGAAAGATGAAGATGGTCCTGTGCAAGAAACACATGAGATTGTC
          P   F   W   Q   N   Q   K   D   E   D   G   P   V   Q   E   T   H   E   I   V
  841 AAGCCTGTTCCAGTTCATTCAAAGAGCCCAATCAACGTTGATGAGCTTGTTGGCATGTCG
          K   P   V   P   V   H   S   K   S   P   I   N   V   D   E   L   V   G   M   S
  901 AAGCTCAGCATAGGAGAGTCCAATCAAGAGACAGAGTCTACTTCTCTTTCATTAAATCTG
          K   L   S   I   G   E   S   N   Q   E   T   E   S   T   S   L   S   L   N   L
  961 GTAGGAGGTCAAAATAGACAATCAGCTTTCCATGCAAATCCACCAACAAGGGCACAGGCA
          V   G   G   Q   N   R   Q   S   A   F   H   A   N   P   P   T   R   A   Q   A
 1021 TGATCTGGTTGTGCACACAACTGCATTTAGATGAATCCCAGGCAAAATAAGCTTTGCCTC
 1081 CTTGTTTTTTGTTTTTATTTTAAGATTAACCGTTCTCCGTAGTCTGTATCATGTGCTGT(SEQ ID NO: 2)
 1141 AAGTTATGCTATGTATGAATGTATCTGTTGTTTGTCTGGCACACATGATAAATCACTCTA
 1201 TGTTAACAAAATCAGTAATGGTAGTGCTGATCTTCGTGGTTGTACTGTTGTAAACTCTTT
 1261 TATAAGAAAAAAAAATATTAGTTAGTC
```

In the above-described transgenic plant, the MYBS3 gene encodes a polypeptide that is at least 40%, e.g., 50, 60, 70, 80, 85, 90, 95, 98, 99, or 100% identical to rice MYBS3 protein (SEQ ID NO: 1). For example, the MYBS3 gene can be a rice MYBS3 gene or its homologues, such as those from other plants (e.g., maize, wheat, barley, sorghum, sugarcane, turf grass, Miscanthus, switchgrass, soybean, canola, potato, tomato, bean, pea, or jatropha). The exemplary homologues are listed below:

> At5g47390 (DNA)

(SEQ ID NO: 43)

ATGACTCGTCGATGTTCTCACTGCAATCACAATGGCCACAACTCTCGGACTTGTCCCAATCGCGG

CGTGAAGCTCTTTGGTGTTCGGCTCACCGAAGGTTCGATCCGGAAAAGTGCAAGTATGGGTAATC

TTAGCCATTACACGGGTTCTGGATCGGGTGGGCATGGAACCGGGTCCAACACTCCGGGTTCTCCG

GGTGATGTCCCTGACCATGTCGCTGGTGATGGTTACGCTTCTGAGGATTTCGTTGCTGGCTCTTC

CTCTAGCCGCGAGAGAAAGAAAGGAACTCCATGGACAGAGGAAGAACACAGGATGTTCTTATTAG

GTTTACAGAAGCTGGGTAAAGGTGATTGGAGAGGTATCTCAAGAAACTATGTGACCACTAGGACA

CCTACACAAGTTGCTAGCCATGCTCAGAAGTATTTCATCAGACAATCCAATGTCTCTCGTCGCAA

AAGACGTTCTAGTCTCTTTGATATGGTTCCTGATGAGGTTGGAGATATTCCCATGGATTTGCAAG

AACCAGAGGAAGATAATATTCCTGTGGAAACTGAAATGCAAGGTGCTGACTCTATTCATCAGACA

CTTGCTCCTAGCTCACTTCACGCACCGTCAATCTTGGAAATCGAAGAATGTGAATCAATGGACTC

CACAAACTCTACCACCGGGGAACCAACCGCAACTGCCGCTGCTGCTTCTTCTTCTTCCAGACTAG

AAGAAACCACACAACTGCAATCACAACTGCAACCGCAGCCGCAACTACCTGGCTCATTCCCCATA

CTATATCCGACCTACTTTTCACCATATTACCCGTTTCCATTCCCAATATGGCCTGCTGGTTATGT

TCCTGAACCACCCAAGAAAGAGGAAACTCATGAAATTCTCAGACCAACTGCTGTGCACTCGAAAG

CTCCTATCAATGTTGACGAGCTTCTTGGTATGTCTAAGCTCAGCCTTGCAGAGTCCAACAAACAT

GGAGAATCCGATCAGTCTCTTTCATTGAAGCTAGGTGGCGGGTCATCTTCAAGACAATCAGCATT

TCACCCGAATCCTAGCTCTGATAGTTCAGACATCAAAAGCGTGATACACGCTTTATAAAAGACCT

GAGGAAGTGATGGTCTAAAATGGG

>At5g47390 (Protein)

(SEQ ID NO: 44)

MTRRCSHCNHNGHNSRTCPNRGVKLFGVRLTEGSIRKSASMGNLSHYTGSGSGGHGTGSNTPGSP

GDVPDHVAGDGYASEDFVAGSSSSRERKKGTPWTEEEHRMFLLGLQKLGKGDWRGISRNYVTTRT

PTQVASHAQKYFIRQSNVSRRKRRSSLFDMVPDEVGDIPMDLQEPEEDNIPVETEMQGADSIHQT

LAPSSLHAPSILEIEECESMDSTNSTTGEPTATAAAASSSSRLEETTQLQSQLQPQPQLPGSFPI

LYPTYFSPYYPFPFPIWPAGYVPEPPKKEETHEILRPTAVHSKAPINVDELLGMSKLSLAESNKH

GESDQSLSLKLGGGSSSRQSAFHPNPSSDSSDIKSVIHAL

> At3g16350 (DNA)

(SEQ ID NO: 45)

ATGACTCGTCGGTGTTCGCATTGTAGCAACAATGGGCACAATTCACGCACGTGTCCAACGCGTGG

TGGTGGCACGTGCGGTGGAAGTGGCGGAGGAGGAGGAGGTGGTGGTGGAGGAGGGTCTGGTTCCT

CCTCCGCCGTGAAGTTATTTGGTGTGAGGTTAACGGATGGCTCGATTATTAAAAAGAGTGCGAGT

ATGGGTAATCTCTCGGCATTGGCTGTTGCGGCGGCGGCAACGCACCACCGTTTATCTCCGTC

GTCTCCTCTGGCGACGTCAAATCTTAATGATTCGCCGTTATCGGATCATGCCCGATACTCTAATT

TGCATCATAATGAAGGGTATTTATCTGATGATCCTGCTCATGGTTCTGGGTCTAGTCACCGTCGT

GGTGAGAGGAAGAGAGGTGTTCCTTGGACTGAAGAGGAACATAGACTATTCTTAGTCGGTCTTCA

GAAACTCGGGAAGGAGATTGGCGCGGTATTTCGAGAAACTATGTAACGTCAAGAACTCCTACAC

AAGTGGCTAGTCATGCTCAAAAGTATTTTATTCGACATACTAGTTCAAGCCGCAGGAAAAGACGG

TCTAGCCTCTTCGACATGGTTACAGATGAGATGGTAACCGATTCATCGCCAACACAGGAAGAGCA

GACCTTAAACGGTTCCTCTCCAAGCAAGGAACCTGAAAAGAAAGCTACCTTCCTTCACTTGAGC

-continued

```
TCTCACTCAATAATACCACAGAAGCTGAAGAGGTCGTAGCCACGGCGCCACGACAGGAAAAATCT

CAAGAAGCTATAGAACCATCAAATGGTGTTTCACCAATGCTAGTCCCGGGTGGCTTCTTTCCTCC

TTGTTTTCCAGTGACTTACACGATTTGGCTCCCTGCGTCACTTCACGGAACAGAACATGCCTTAA

ACGCTGAGACTTCTTCTCAGCAGCATCAGGTCCTAAAACCAAAACCTGGATTTGCTAAAGAACGT

GTGAACATGGACGAGTTGGTCGGTATGTCTCAGCTTAGCATAGGAATGGCGACAAGACACGAAAC

CGAAACTTCCCCTTCCCCGCTATCTTTGAGACTAGAGCCCTCAAGGCCATCAGCGTTTCACTCGA

ATGGCTCGGTTAATGGTGCAGATTTGAGTAAAGGCAACAGCGCGATTCAGGCTATCTAA
```

>At3g1635 (Protein)
(SEQ ID NO: 46)

```
MTRRCSHCSNNGHNSRTCPTRGGGTCGGSGGGGGGGGGGGGSGSSSAVKLFGVRLTDGSIIKKSAS

MGNLSALAVAAAAATHHRLSPSSPLATSNLNDSPLSDHARYSNLHHNEGYLSDDPAHGSGSSHRR

GERKRGVPWTEEEHRLFLVGLQKLGKGDWRGISRNYVTSRTPTQVASHAQKYFIRHTSSSRRKRR

SSLFDMVTDEMVTDSSPTQEEQTLNGSSPSKEPEKKSYLPSLELSLNNTTEAEEVVATAPRQEKS

QEAIEPSNGVSPMLVPGGFFPPCFPVTYTIWLPASLHGTEHALNAETSSQQHQVLKPKPGFAKER

VNMDELVGMSQLSIGMATRHETETSPSPLSLRLEPSRPSAFHSNGSVNGADLSKGNSAIQAI
```

> GRMZM2G034110_T01 (DNA)
(SEQ ID NO: 47)

```
ATGACGCGGCGGTGCTCGCACTGCAGCCACAACGGGCACAACTCGCGGACGTGCCCCAACCGCGG

GGTCAAGATCTTCGGGGTGCACCTCACCGATGGCTCGGCCATCCGCAAGAGCGCGAGCATGGGGA

ACCTCTCCCTCCTCTCCGCGGGATCCACCAGCGGCGGCGCGTCCCCCGCCGACGGGCCCGACCTC

GCCGACGGCGGCGGGGGCTACGCCTCCGACGACTTCGTCCAGGGGTCGTCCTCCGCCAGCCGCGA

TCGAAAGAAAGGTGTTCCTTGGACTGAAGAAGAACACCGGAGGTTTTTGCTGGGATTACAAAAGC

TCGGGAAAGGGGATTGGCGAGGAATTTCTCGTAATTTTGTGGTCTCAAGAACACCTACTCAAGTA

GCAAGTCATGCTCAAAAGTATTTTATACGCCAATCAAATATGAGCAGAAGGAAGAGAAGGTCTAG

CCTTTTCGACATGGTTCCTGATGAGTCCATGGACCTTCCGCCCCTTCCTGGAAGTCAAGAACCAG

AGACCTCAATGTTAAATCAACCGCCACTGCCTCCTGCTGTGGAGGAGGAGGTGGAATCGATGGAG

TCAGATACTTCTGCTGTCGCAGAGAGTTCTGGAGCTTCTGCTCTCATGCCCGAGAGTTTACAGCC

TACCTATCCGATGATTGTTCCAGCTTATTTCTCGCCGTTCTTGCAATTCTCAGTTCCTTTCTGGC

CAAATCAGGAAGATGGAGGCGATCTTCCCCAAGAAACACACGAGATTGTCAAGCCTGTTGCAGTT

CATTCCCAGAATCCAATTAATGTTGATGAACTCGTGGGCATGTCAAAGCTAAGCATATGGGAGCA

TGGTCAGGAGACAGTGTCTACTTCTCTGTCGCTAAATCTGCTAGGGGGTCAAAATAGGCAGTCGG

CTTTCCATGCAAACCCTCAAACAAGAGCTCAAGCCTGA
```

>GRMZM2G034110_T01 (Protein)
(SEQ ID NO: 48)

```
MTRRCSHCSHNGHNSRTCPNRGVKIFGVHLTDGSAIRKSASMGNLSLLSAGSTSGGASPADGPDL

ADGGGGYASDDFVQGSSSASRDRKKGVPWTEEEHRRFLLGLQKLGKGDWRGISRNFVVSRTPTQV

ASHAQKYFIRQSNMSRRKRRSSLFDMVPDESMDLPPLPGSQEPETSMLNQPPLPPAVEEEVESME

SDTSAVAESSGASALMPESLQPTYPMIVPAYFSPFLQFSVPFWPNQEDGGDLPQETHEIVKPVAV

HSQNPINVDELVGMSKLSIWEHGQETVSTSLSLNLLGGQNRQSAFHANPQTRAQA
```

> GRMZM2G020934_T01 (DNA)
(SEQ ID NO: 49)

```
ATGGCTCGGCCATCCGCAAGAGCGCAAGCATGGGGAACCTCTCCCTCCTCTCCGCGGGGTCAACC

AGCGGCGGCGCGTCGCCCGCCGACGGGCCCGACCTCGCCGACGGCGGCGGGGGCTACGCCTCCGA

CGACTTCGTCCAGGGGTCGTCCTCCGCCAGCCGCGAGCGTAAGAAAGGTGTTCCTTGGACTGAAG

AAGAACACCGGAGGTTTTTTGCTGGGATTACAAAAAGCTTGGGGAAAGGTGATTGGCGAGGGGA
```

-continued

TTTTCTCGTAATTTTCGTGGTCTCAAAGAACACCCTACTCAAAGTAGCAAAGTCATGCTCAAAAA

ATATTTTATACGTCAAATCAAATATGAGCAGAAGGGAAGAGAAGGTCTAGCCTTTTTTGACATG

GTGCCTGATGAGTCCATGGACCTTCCACCCCTTCCTGGAAGTCAAGAGCCAGAGACCTCAGTGTT

AAATCAACCACCACTGCCTCCCCCTGTGGAGGAGGAGGAGGAGGTGGAATCGATGGAGTCAGATA

CTTCTGCTGTTGCGGAGAGTTCTGCAGCTTCAGCTCTTATGCCCGAGAGTTTACAGCCTACCTAT

CCGATGATTGTTCCAGCTTATTTCTCACCGTTCTTGCAATTCTCAGTTCCTTTCTGGCCAAATCA

GGAAGATGGAGGTGATCTGCCTCAAGAAACGCACGAGATTGTCAAGCCTGTTGCAGTTCATTCCA

AGAATCCAATTAATGTTGATGAACTTGTGAGCATGTCAAAGCTAAGCATAGGGGAGCCTGGTCAG

GAAACGGTGTCTACTTCTCTGTCGTTAAATCTGCTGGTGGGTCAAAATAGGCAGTCGGCCTTCCA

TGCAAATCCTCAAACGAGGGCTCAAGCTTGA

>GRMZM2G020934_T01 (Protein)
(SEQ ID NO: 50)
MARPSARAQAWGTSPSSPRGQPAAARRPPTGPTSPTAAGATPPTTSSRGRPPPAASVRKVFLGLK

KNTGGFLLGITKSLGKGDWRGDFLVIFVVSKNTLLKVAKSCSKNIFIRQIKYEQKGREGLAFFDM

VPDESMDLPPLPGSQEPETSVLNQPPLPPPVEEEEEVESMESDTSAVAESSAASALMPESLQPTY

PMIVPAYFSPFLQFSVPFWPNQEDGGDLPQETHEIVKPVAVHSKNPINVDELVSMSKLSIGEPGQ

ETVSTSLSLNLLVGQNRQSAFHANPQTRAQA

> Sb01g029020.1 (DNA)
(SEQ ID NO: 51)
ATGACGCGGCGGTGCTCGCACTGCAGCCACAACGGGCACAACTCGCGGACGTGCCCCAACCGCGG

GGTCAAGATCTTCGGGGTGCGCCTCACCGATGGCTCCGCCATCCGCAAGAGCGCCAGCATGGGGA

ACCTCTCCCTCCTCTCCGCGGGATCCACCAGCGGCGGCGCGTCCCCCGCCGACGGGCCCGACCTC

GCCGACGGCGGCGCCGGGGGATACGCCTCCGACGACTTCGTCCAGGGCTCCTCCTCCGCCAGCCG

CGAGCGCAAGAAGGTGTTCCTTGGACTGAAGAAGAACACCGGAGGTTTTTGCTGGGATTACAAA

AGCTTGGGAAAGGTGATTGGCGAGGAATTTCTCGTAATTTCGTGGTCTCAAGAACACCTACTCAA

GTAGCAAGTCATGCTCAAAAATATTTTATACGTCAATCAAATATGAGCAGAAGGAAGAGAAGGTC

TAGCCTTTTTGACATGGTGCCTGATGAGTCCATGGACCTTCCACCCCTTCCTGGAAGTCAAGAAC

CAGAGACCTCAGTGTTAAATCAAGCACCACTGCCGCCTCCTGTGGAGGAGGAGGTGGAATCAATG

GAGTCAGATACTTCTGCTGTTGCAGAGAGTTCTACGGCTTCTGCTCTCATGCCCGAGAGTTTACA

ACCTAATTATCCGATGATTGTTCCAGCTTATTTCTCACCGTTCTTGCAATTCTCAGTTCCTTTCT

GGCCAAATCAGGAAGATGGAGGCGATCTGCCCCAAGAAACACACGAGATTGTCAAGCCTGTGGCA

GTTCATTCCAAGAATCCAATTAATGTTGATGAACTTGTGGGCATGTCAAAGCTAAGCATAGGGGA

GCCTGGTCAGGAGACAGTTTCTACTTCTCTGTCGCTAAATCTGCTAGGGGGTCAAAATAGGCAGT

CGGCTTTCCATGCAAATCCTCAAACGAGAGCTCAAGCCTGA

>Sb01g029020.1 (Protein)
(SEQ ID NO: 52)
MTRRCSHCSHNGHNSRTCPNRGVKIFGVRLTDGSAIRKSASMGNLSLLSAGSTSGGASPADGPDL

ADGGAGGYASDDFVQGSSSASRERKKGVPWTEEEHRRFLLGLQKLGKGDWRGISRNFVVSRTPTQ

VASHAQKYFIRQSNMSRRKRRSSLFDMVPDESMDLPPLPGSQEPETSVLNQAPLPPPVEEEVESM

ESDTSAVAESSTASALMPESLQPNYPMIVPAYFSPFLQFSVPFWPNQEDGGDLPQETHEIVKPVA

VHSKNPINVDELVGMSKLSIGEPGQETVSTSLSLNLLGGQNRQSAFHANPQTRAQA

>Sb03g003270.1 (DNA)

-continued (SEQ ID NO: 53)
ATGACGCGGAGGTGCTCGCACTGCAGCAACAACGGCCACAACTCGCGCACCTGCCCCGCCCGCTC

CGGCGGCGGGGTGAGGCTATTTGGCGTGCGCCTCACAACGGCGCCGGCTCCGGCGGCGATGAAGA

AGAGCGCCAGCATGAGCTGCATCGCGTCCTCGCTCGGGGCGGGTCCGGGGGCTCGTCGCCGCCG

GCGGGAGGAGTGGGTGGTGGCAGGGGAGGAGGAGACGGCGGGGCCGGCTACGTCTCCGATGATCC

CGGGCACGCCTCCTGCTCGACGAATGGCCGCGTCGAGCGGAAGAAAGGTACACCTTGGACTGAAG

AAGAGCATAGAATGTTTCTGATGGGTCTTCAGAAGCTTGGTAAGGGAGATTGGCGCGGGATATCT

CGAAACTTTGTTGTTTCCAGGACCCCGACTCAAGTGGCAAGCCATGCTCAAAAGTACTTTATTAG

ACAGACAAACTCATCAAGACGGAAGAGGCGGTCAAGCTTGTTTGACATGGTTGCAGAAATGCCAG

TAGACGAGTCCCTAGCTGCTGCGGAACAAATTACTATCCAAAATACTCAAGATGAAGCTGCAAGT

TCAAATCAACTGCCGACCTTACATCTTGGGCATCAGAAGGAAGCAGAGTTTGCTAAGCAAATGCC

AACTTTTCAGCTAAGGCAGCATGAGGAATCTGAATATGCAGAACCTTCATTGACATTACCAGATT

TAGAGATGAACTCCAGTGTACCATTCAATACCATAGCTGTTCCGACGATGCCAGCATTCTACCCT

GCGTTGGTCCCTGTTCCACTAACTCTTTGGCCTCCAAGTGTTGCCCATGTGGAGGACGCAGGCAC

AACCCATGAAATCCTAAAACCAACTCCTTTGAATGGTAAGGAGGTGATTAAAGCAGATGATGTTG

TTGGTATGTCTAAGCTCAGCATTGGTGAGGCCAGCTCTGGCTCCATGGAACCCACAGCTCTTTCC

CTTCAGCTTATTGGATCGACAGATACAAGGCAGTCAGCTTTTCATGTGAGTCCACCAATGAATAG

ACCTGAACTAAGCAAGAGAAACAGCAGTCCAATTCATGCCGTTTGA

>Sb03g003270.1 (Protein)

(SEQ ID NO: 54)
MTRRCSHCSNNGHNSRTCPARSGGGVRLFGVRLTTAPAPAAMKKSASMSCIASSLGGGSGGSSPP

AGGVGGGRGGGDGGAGYVSDDPGHASCSTNGRVERKKGTPWTEEEHRMFLMGLQKLGKGDWRGIS

RNFVVSRTPTQVASHAQKYFIRQTNSSRRKRRSSLFDMVAEMPVDESLAAAEQITIQNTQDEAAS

SNQLPTLHLGHQKEAEFAKQMPTFQLRQHEESEYAEPSLTLPDLEMNSSVPFNTIAVPTMPAFYP

ALVPVPLTLWPPSVAHVEDAGTTHEILKPTPLNGKEVIKADDVVGMSKLSIGEASSGSMEPTALS

LQLIGSTDTRQSAFHVSPPMNRPELSKRNSSPIHAV

> Glyma17g15330.1 (DNA)

(SEQ ID NO: 55)
ATGACGCGGCGTTGCTCGCATTGCAGCCACAATGGGCACAACTCAAGAACTTGCCCTAACCGCGG

GGTGAAGCTCTTCGGGGTCCGATTAACCGATGGGTCGATCCGGAAGAGTGCTAGCATGGGCAATC

TAACCCACTATGCCGGTTCCGGGTCGGGTCCACTCCATACCGGGTTGAATAACCCCGGTTCGCCC

GGGGAAACCCCCGATCATGCCGCCGCAGTCGCCGACGGTTACTTGTCCGAGGACTTCGTTCCCGG

GTCTTCTTCTAGCTCCCGTGAAAGAAAGAAGGGTGTTCCATGGACTGAGGAGGAACATAGAATGT

TTTTACTCGGATTGCAGAAGCTGGGCAAAGGTGATTGGCGTGGAATTGCAAGGACCTATGTTATA

TCAAGGACACCTACTCAAGTGGCTAGCCATGCTCAGAAATATTTCATCAGGCAGAGCAATGTGTC

CAGGCGGAAAAGACGGTCCAGCTTGTTTGATATTGTTGCAGATGAAGCAGCTGACACTGCAATGG

TACAGCAAGACTTCTTGTCTGCTAATCAGTTACCCACTGAAACAGAAGGCAATAACCCCTTGCCA

GCTCCTCCTCCCCTCGACGAAGAGTGCGAATCCATGGATTCCACAAACTCAAATGATGGAGAGCC

TGCCCCATCAAAGCCAGAAAACACACAGTCATCTTATCCAATGTTATATCCTGCATATTATTCTC

CGGTGTTCCCGTTTCCTCTGCCCTATTGGTCAGGATACAGTCCAGAGTCCACCAAGAAGGAGGAG

ACACATGAAGTACTGAAGCCAACTGCAGTTCATTCTAAAAGCCCTATCAATGTTGATGAACTGGT

TGGCATTTCAAAATTGAGTTTAGGGGAGTCTATTGGTGACTCTGGTCCCTCCTCTCTGTCTCGAA

-continued

```
AACTTATCGAAGAAGGACCCTCTAGACAGTCAGCTTTTCATGCAACACCGACATGTGGCAGTTCA

AATGGCAGTGCCATCCATGCAGTTTAA
```

>Glyma17g15330.1 (Protein)

(SEQ ID NO: 56)

```
MTRRCSHCSHNGHNSRTCPNRGVKLFGVRLTDGSIRKSASMGNLTHYAGSGSGPLHTGLNNPGSP

GETPDHAAAVADGYLSEDFVPGSSSSSRERKKGVPWTEEEHRMFLLGLQKLGKGDWRGIARTYVI

SRTPTQVASHAQKYFIRQSNVSRRKRRSSLFDIVADEAADTAMVQQDFLSANQLPTETEGNNPLP

APPPLDEECESMDSTNSNDGEPAPSKPENTQSSYPMLYPAYYSPVFPFPLPYWSGYSPESTKKEE

THEVLKPTAVHSKSPINVDELVGISKLSLGESIGDSGPSSLSRKLIEEGPSRQSAFHATPTCGSS

NGSAIHAV
```

> Glyma05g04950.1 (DNA)

(SEQ ID NO: 57)

```
ATGACGCGGCGTTGCTCGCATTGCAGCCACAATGGGCACAACTCCAGAACCTGCCCTAACCGCGG

GGTTAAGCTCTTCGGGGTCCGATTAACCGACGGGTCGATCCGGAAGAGCGCCAGCATGGGCAACC

TAACCCACTACGCTGGTTCCGGGTCGGCCCCGCTCCATGTCGGGTTGAATAACCCGGGTTCACCC

GGGGAGACGCCCGATCACGCCGCCGCCGCCGACGGCTACGCCTCCGAGGACTTCGTTCCCGG

GTCTTCTTCTAGCTCCCGTGAAAGAAAGAAGGGTGTTCCATGGACTGAGGAGGAACATAGAATGT

TTTTGCTCGGATTGCAGAAGCTGGGCAAAGGTGATTGGCGTGGAATTGCAAGGAACTATGTTATA

TCAAGGACGCCTACTCAAGTGGCCAGCCATGCTCAGAAATATTTCATCAGGCAAAGCAATGTGTC

CAGGCGAAAAGACGGTCCAGCTTGTTTGATATTGTTGCAGATGAAGCAGCTGACACTGCAATGG

TACAGCAAGACTTCTTGTCTGCTAATGAGTTACCAACTGAAACAGAAGGCAATAACCCCTTGCCT

GCTCCTCCTCCCCTCGATGAAGAGTGTGAATCAATGGATTCCACAAACTCAAATGATGGAGAGCC

TGCCCCATCAAAGCCAGAAAACACACATCCATCTTATCCTATGTTATATCCTGCGTATTATTCTC

CAGTGTTCCCGTTTCCTCTGCCCTATTGGTCAGGATACAGTCCAGAGCCCACCAAGAAGGAGGAA

ACACATGAAGTGCTGAAACCAACTGCAGTACATTCTAAAAGCCCTATCAATGTTGATGAACTGGT

TGGCATATCAAAACTGAGTTTAGGGGAGTCTATTGGTGACTCGGGTCCCTCCACCCTGTCTCGAA

AACTTATTGAAGAAGGACCCTCTAGACAATCAGCTTTTCATGCAACACCAACATGTGGTGATATG

AATGGCAGTGCCATCCATGCAGTTTAA
```

>Glyma05g04950.1 (Protein)

(SEQ ID NO: 58)

```
MTRRCSHCSHNGHNSRTCPNRGVKLFGVRLTDGSIRKSASMGNLTHYAGSGSAPLHVGLNNPGSP

GETPDHAAAAADGYASEDFVPGSSSSSRERKKGVPWTEEEHRMFLLGLQKLGKGDWRGIARNYVI

SRTPTQVASHAQKYFIRQSNVSRRKRRSSLFDIVADEAADTAMVQQDFLSANELPTETEGNNPLP

APPPLDEECESMDSTNSNDGEPAPSKPENTHPSYPMLYPAYYSPVFPFPLPYWSGYSPEPTKKEE

THEVLKPTAVHSKSPINVDELVGISKLSLGESIGDSGPSTLSRKLIEEGPSRQSAFHATPTCGDM

NGSAIHAV
```

> GSVIVT00013475001 (DNA)

(SEQ ID NO: 59)

```
ATGACTCGCCGCTGCTCGCATTGCAGTCACAACGGGCACAATTCCAGGACATGCCCCAACCGCGG

GGTCAAGATCTTCGGGGTTCGATTGACTGATGGGTTGATCCGTAAGAGTGCTAGTATGGGCAATC

TCAGCCACTACGCCGGGTCGACCTCTGGTCATCATCAGAACGGCGTTTCCGGTAACAATTCGGTC

TCTCCCGGAGAGACTCCAGAGCACGGCGCCGCGGCCGATGGATACGCCTCCGAGGGTTTCGTTCC

CGGTTCATCATCCAGCCGGGAGCGCAAGAAAGGCACTCCATGGACTGAAGAGGAACACAGAATGT

TTCTACTTGGACTGCAGAAGCTTGGAAAAGGGGATTGGCGTGGAATTTCACGTAATTATGTTATA
```

-continued

TCAAGGACACCTACTCAAGTCGCCAGCCATGCTCAGAAATATTTCATCAGGCAAACTAATGTGTC

TAGGAGAAAAAGACGGTCCAGCTTGTTTGATATTGTAGCTGATGAATCTGTCGACACTCCAATGG

TATCACGGGATTTCTTCTCCACCAACCCTTCGCAAGCTGAAACACTAAGCAATAACCCATTGCCT

GTTCCTCCGGCTCTGGATGAAGAATGTGAATCAATGGATTCTACCAACTCGAATGATGGAGAACC

GCCCATTCCAAAGCCGGATGGCTTACAAGGCTGTCCCCCAGTAATATATCCTACTTATTTCTCAC

CATTCTTCCCATTTTCTTTTCCATTCTGGCCGGGAAACAGTTCAGAGCCAACTAAAATGGAGACT

CATGAGGTGCTTAAGCCAACAGCTGTACATTCTAAGAGTCCAATCAATGTTGATGAGCTGGTTGG

CATGTCAAAACTGAGTTTAGGAGAATCCATCGGTCATGCTGGTCCCTCCTCTCTCACACTGAAAC

TGCTTGAAGGGTCAAGCAGGCAATCTGCTTTCCATGCTAATCCAGCCTCTGGCAGTTCAAGCATG

AACTCGAGCGGCAGTCCAATCCATGCAGTTTGA

>GSVIVT00013475001 (Protein)
(SEQ ID NO: 60)
MTRRCSHCSHNGHNSRTCPNRGVKIFGVRLTDGLIRKSASMGNLSHYAGSTSGHHQNGVSGNNSV

SPGETPEHGAAADGYASEGFVPGSSSSRERKKGTPWTEEEHRMFLLGLQKLGKGDWRGISRNYVI

SRTPTQVASHAQKYFIRQTNVSRRKRRSSLFDIVADESVDTPMVSRDFFSTNPSQAETLSNNPLP

VPPALDEECESMDSTNSNDGEPPIPKPDGLQGCPPVIYPTYFSPFFPFSFPFWPGNSSEPTKMET

HEVLKPTAVHSKSPINVDELVGMSKLSLGESIGHAGPSSLTLKLLEGSSRQSAFHANPASGSSSM

NSSGSPIHAV

> GSVIVT00012218001 (DNA)
(SEQ ID NO: 61)
ATGACTCGCCGCTGCTCGCATTGCAGTCACAACGGGCACAATTCCAGGACATGCCCCAACCGCGG

GGTCAAGATCTTCGGGGTTCGATTGACTGATGGGTTGATCCGTAAGAGTGCTAGTATGGGCAATC

TCAGCCACTACGCCGGGTCGACCTCTGGTCATCATCAGAACGGCGTTTCCGGTAACAATTCGGTC

TCTCCCGGAGAGACTCCAGAGCACGGCGCCGCGGCCGATGGATACGCCTCCGAGGGTTTCGTTCC

CGGTTCATCATCCAGCCGGGAGCGCAAGAAAGGCACTCCATGGACTGAAGAGGAACACAGAATGT

TTCTACTTGGACTGCAGAAGCTTGGAAAAGGGGATTGGCGTGGAATTTCACGTAATTATGTTATA

TCAAGGACACCTACTCAAGTCGCCAGCCATGCTCAGAAATATTTCATCAGGCAAACCAATGTGTC

TAGGAGAAAAAGACGGTCCAGCTTGTTTGATATTGTAGCTGATGAATCTGTTGACACTCCAATGG

TATCACGGGATTTCTTCTCCACCAACCCTTCGCAAGCTGAAACACTAAGCAATAACCCATTGCCT

GTTCCTCCGGCTCTGGATGAAGAATGTGAATCAATGGATTCTACCAACTCGAATGATGGAGAACC

ACCCATTCCAAAGCCGGATGGCTTACAAGGCTGTCCCCCAGTAATATATCCTACTTATTTCTCGC

CATTCTTCCCATTTTCTTTTCCATTCTGGCCGGGAAACAGTTCAGAGCCAACTAAAATGGAGACT

CATGAGGTGCTTAAGCCAACAGCTGTACATTCTAAGAGTCCAATCAATGTTGATGAGCTGGTTGG

CATGTCAAAACTGAGTTTAGGAGAATCCATCGGTCATGCTGGTCCCTCCTCTCTCACACTGAAAC

TGCTTGAAGGGTCAAGCAGGCAATCTGCTTTCCATGCTAATCCAGCCTCTGGCAGTTCAAGCATG

AACTCGAGCGGCAGTCCAATCCATGCACCCAATGGGAAGATTCTGCTGGTATGGAGATTGTAG

>GSVIVT00012218001 (Protein)
(SEQ ID NO: 62)
MTRRCSHCSHNGHNSRTCPNRGVKIFGVRLTDGLIRKSASMGNLSHYAGSTSGHHQNGVSGNNSV

SPGETPEHGAAADGYASEGFVPGSSSSRERKKGTPWTEEEHRMFLLGLQKLGKGDWRGISRNYVI

SRTPTQVASHAQKYFIRQTNVSRRKRRSSLFDIVADESVDTPMVSRDFFSTNPSQAETLSNNPLP

VPPALDEECESMDSTNSNDGEPPIPKPDGLQGCPPVIYPTYFSPFFPFSFPFWPGNSSEPTKMET

HEVLKPTAVHSKSPINVDELVGMSKLSLGESIGHAGPSSLTLKLLEGSSRQSAFHANPASGSSSM

NSSGSPIHAPNGKILLVWRL

> LjT37H17.80.nd (DNA)

(SEQ ID NO: 63)

ATGACCCGGCGATGCTCGCATTGCAGCCATGGTGGCCACAACGCCAGGACCTGCCCCAACCGCGG

AGTCAAGCTTTTCGGTGTCCGATTGACTGATGGCTCGATCCGGAAGAGTGCTAGTATGGGTAATC

TCACCCACTACACTGGCTCCGGGTCTGGACCTCTTCTTGGTGGGTCCAATAACCCTGATTCTCCC

GGTGAAACCCCTGATCACGCCGCCGCTGCTGACGGTTACGCCTCTGAGGATTTTGTTCCTGGCTC

TTCTTCTAGCTCCCGTGAAAGAAAAAAGGGCACTCCATGGACTGAGGAGGAACACAGAATGTTTT

TACTTGGATTGCAGAAACTGGGCAAAGGTGATTGGCGTGGAATTGCAAGGAACTATGTTATTTCA

AGGACACCTACTCAAGTGGCCAGTCATGCTCAGAAATATTTCATCAGGCAAAGCAATGTGTCTAG

GAGAAAGAGACGGTCCAGCTTGTTTGATATTGTTGCAGATGATGCGTCCGACACTCCAATGGTAG

AGCAAGACTTCTTGTCAGCTAATCAGCTACAGACTGAAACAGAAGGCAATAACCCTTTGCCTGCT

CCTCCTCCCATTGATGAAGAGTGTGAATCCATGGATTCCACAAACTCAATAGATGGAGACTCTGC

CCTGTTAAAGCCCGACACTCCAATACCGCCAACCTACCCGGTGTTATATCCTGCATATTATCCTC

CATTCTACCCGTATCCTCTGCCTTATTGGTCTGGATACAGTCCTGCAGAGCCCCCAAAGAAAGAG

GAGACACATGAAGTGGTGAAGCCAACTGCGGTGCTTTCCAAAAGCCCAATCAATGTGGATGAACT

TGTCGGCATGTCAAAACTGAGTTTGGGAGACTCCATTGGTGACTCTGGCCCCTCCTCTCTGTCTC

GAAAACTCGTCGAAGAAGGACCTTCCAGACAATCAGCTTTTCATGCTACTCCAGCATGTGGCAGT

TCAAATATAAATGGCAGTGTCATACATGCAGTTTAA

>LjT37H17.80.nd (Protein)

(SEQ ID NO: 64)

MTRRCSHCSHGGHNARTCPNRGVKLFGVRLTDGSIRKSASMGNLTHYTGSGSGPLLGGSNNPDSP

GETPDHAAAADGYASEDFVPGSSSSSRERKKGTPWTEEEHRMFLLGLQKLGKGDWRGIARNYVIS

RTPTQVASHAQKYFIRQSNVSRRKRRSSLFDIVADDASDTPMVEQDFLSANQLQTETEGNNPLPA

PPPIDEECESMDSTNSIDGDSALLKPDTPIPPTYPVLYPAYYPPFYPYPLPYWSGYSPAEPPKKE

ETHEVVKPTAVLSKSPINVDELVGMSKLSLGDSIGDSGPSSLSRKLVEEGPSRQSAFHATPACGS

SNINGSVIHAV

>chr2.CM0028.230.nd (DNA)

(SEQ ID NO: 65)

ATGTCTCGCACGTGCTCACAGTGCGGCAACAACGGCCACAACTCCCGCACATGCACCGACACCGC

CGCCGCTGGAGACAACGGCATCATGCTCTTCGGCGTGCGCCTCACCGAAGGCTCCACCTCCTCCT

CCGCCTTCATCAGGAAGAGCGCTAGCATGAACAACCTCTCCCAGTATAACGAACCCGAATCCAAC

CCCGCTGACGCAGCTGGCTACGCCTCCGACGACGTCGTTCATCCCTCCGCACGCGCCCGCGACCG

CAAGCGAGGTGTGCCTTGGACGGAAGAAGAACACAAACTGTTTCTGTTGGGATTGCATAAAGTGG

GGAAGGGAGATTGGAGAGGAATTTCTAGAAACTTCGTCAAAACTCGCACACCCACTCAGGTTGCT

AGTCATGCTCAGAAGTATTTCCTCCGCCGTCACAACCATAACCGCCGGCGCCGGAGATCTAGCCT

TTTCGACATCACCACCGATACGGTGATGGAATCTTCAACAATAATGGAGGAAGAACAAGATCAGC

AAGAAATGGTGCCGCCAGCTACCTCCGCCGTGTATCCGCCGTTACATTACGGTGGCTTCCACGGC

CCAGCGTTTCCAATGGCTCTGTCTCCGGTGGTATTGCCGGTGGCCGGAGGGGAAAGACCGGCAAG

GCCGATTAGGCCAACGCCGATTTTCCCTGTGCCTCCGTCTTCTAAGATGGCTAGTTTGAACTTGA

AAGAGAAAGCAGCTTCTCCTTCCCCTTCTTCTCCATTTGAGCCTCTACCGCTGTCGCTGAAGCTG

CAGCCATCTCCGCCGCCGTCCAAGGATCATTCTCCGGCAACCAGTAGCCACTCGTCGCCATCATC

GCCGTCTTCTTCATCATCTTTTTCAGGCTATGTCTGCAGGGAAGTTCAGCGGTGGTGGAGATAGCA

TTATTAGTGTTGCTTGA

```
-continued
>chr2.CM0028.230.nd (Protein)
                                                    (SEQ ID NO: 66)
MSRTCSQCGNNGHNSRTCTDTAAAGDNGIMLFGVRLTEGSTSSSAFIRKSASMNNLSQYNEPESN

PADAAGYASDDVVHPSARARDRKRGVPWTEEEHKLFLLGLHKVGKGDWRGISRNFVKTRTPTQVA

SHAQKYFLRRHNHNRRRRRSSLFDITTDTVMESSTIMEEEQDQQEMVPPATSAVYPPLHYGGFHG

PAFPMALSPVVLPVAGGERPARPIRPTPIFPVPPSSKMASLNLKEKAASPSPSSPFEPLPLSLKL

QPSPPPSKDHSPATSSHSSPSSPSSSSSFQAMSAGKFSGGGDSIISVA
```

As shown below, SEQ ID NOs: 44, 46, 48, ..., and 66 share at least 44% homology with SEQ ID NO: 1. Also see FIG. 5 for a multiple protein sequence alignment.

| No. | Species | Gene ID | Identities (%) | Positives (%) |
|-----|---------|---------|----------------|---------------|
| 1 | Arabidopsis thaliana | AT5G47390 | 56 | 66 |
| 2 | Arabidopsis thaliana | AT3G16350 | 45 | 55 |
| 3 | Zea May | GRMZM2G034110_T01 | 86 | 90 |
| 4 | Zea May | GRMZM2G020934_T01 | 62 | 69 |
| 5 | Sorghum bicolor (Sorghum) | Sb01g029020.1 | 87 | 90 |
| 6 | Sorghum bicolor (Sorghum) | Sb03g003270.1 | 44 | 56 |
| 7 | Glycine max (Soybean) | Glyma17g15330.1 | 61 | 72 |
| 8 | Glycine max (Soybean) | Glyma05g04950.1 | 58 | 71 |
| 9 | Vitis vinifera (Wine Grape) | GSVIVT00013475001 | 62 | 71 |
| 10 | Vitis vinifera (Wine Grape) | GSVIVT00012218001 | 62 | 71 |
| 11 | Lotus japonicus (Lotus) | LjT37H17.80.nd | 59 | 71 |
| 12 | Lotus japonicus (Lotus) | chr2.CM0028.230.nd | 57 | 68 |

As used herein, "percent homology" of two sequences is determined using the algorithm described in Karlin and Attschul, *Proc, Natl. Acad. Sci. USA* 87:2264-2268, 1990, modified as described in Karlin and Altschul, *Proc. Natl. Acad. Sci. USA* 90:5873-5877, 1993. Such an algorithm is incorporated into the NBLAST and XBLAST programs of Altschul et al., *J Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See the NCBI website at ncbi.nlm,nih.gov.

In a preferred embodiment, the cell also has a DREB1 gene expression level that is higher than a wild type DREB1 protein level so that the plant over-expresses both MYBS3 and DREB1. Listed below are cDNA and protein sequences of DREB1A, 1B, 1C, and 1D.

```
OsDREB1A (dehydration-responsive element-binding protein
1A) LOC_Os09g35030
CDS >12009.m06503
                                                    (SEQ ID NO: 3)
ATGTGCGGGATCAAGCAGGAGATGAGCGGCGAGTCGTCGGGGTCGCCGTGCAGCTCGGCG

TCGGCGGAGCGGCAGCACCAGACGGTGTGGACGGCGCCGCCGAAGAGGCCGGCGGGGCGG

ACCAAGTTCAGGGAGACGAGGCACCCGGTGTTCCGCGGCGTGCGGCGGAGGGGCAATGCC

GGGAGGTGGGTGTGCGAGGTGCGGGTGCCCGGCGGCGCGGCTGCAGGCTCTGGCTCGGC

ACGTTCGACACCGCCGAGGGCGCGGCGCGCGCACGACGCCGCCATGCTCGCCATCAAC

GCCGGCGGCGGCGGCGGGGGAGCATGCTGCCTCAACTTCGCCGACTCCGCGTGGCTC

CTCGCCGTGCCGCGCTCCTACCGCACCCTCGCCGACGTCCGCCACGCCGTCGCCGAGGCC

GTCGAGGACTTCTTCCGGCGCCGCCTCGCCGACGACGCGCTGTCCGCCACGTCGTCGTCC

TCGACGACGCCGTCCACCCCACGCACCGACGACGACGAGGAGTCCGCCGCCACCGACGGC

GACGAGTCCTCCTCCCCGGCCAGCGACCTGGCGTTCGAACTGGACGTCCTGAGTGACATG

GGCTGGGACCTGTACTACGCGAGCTTGGCGCAGGGGATGCTCATGGAGCCACCATCGGCG

GCGCTCGGCGACGACGGTGACGCCATCCTCGCCGACGTCCCACTCTGGAGCTACTAG
```

-continued

Protein >12009.m06503

(SEQ ID NO: 4)
MCGIKQEMSGESSGSPCSSASAERQHQTVWTAPPKRPAGRTKFRETRHPVFRGVRRRGNA

GRWVCEVRVPGRRGCRLWLGTFDTAEGAARAHDAAMLAINAGGGGGGACCLNFADSAWL

LAVPRSYRTLADVRHAVAEAVEDFFRRRLADDALSATSSSSTTPSTPRTDDDEESAATDG

DESSSPASDLAFELDVLSDMGWDLYYASLAQGMLMEPPSAALGDDGDAILADVPLWSY*

OsDREB1B (dehydration-responsive element-binding protein
1B)LOC_Os09g35010
CDS >12009.m06501

(SEQ ID NO: 5)
ATGGAGGTGGAGGAGGCGGCGTACAGGACGGTGTGGTCGGAGCCGCCGAAGAGGCCGGCG

GGAAGGACCAAGTTCAGGGAGACGAGGCACCCGGTGTACCGCGGCGTGCGGCGGCGCGGG

GGGCGGCCGGGCGCGGCGGGGAGGTGGGTGTGCGAGGTGCGGGTGCCCGGGGCGCGCGGC

TCCAGGCTGTGGCTCGGCACGTTCGCCACCGCCGAGGCGGCGGCGCGCGCACGACGCC

GCCGCGCTGGCGCTCCGCGGCAGGGCCGCCTGCCTCAACTTCGCCGACTCCGCGTGGCGG

ATGCCGCCCGTCCCCGCGTCCGCCGCGCTCGCCGGCGCGAGGGGGGTCAGGGACGCCGTC

GCCGTGGCCGTCGAGGCGTTCCAGCGCCAGTCGGCCGCGCCGTCGTCTCCGGCGGAGACC

TTCGCCAACGATGGCGACGAAGAAGAAGACAACAAGGACGTGTTGCCGGTGGCGGCGGCG

GAGGTGTTCGACGCGGGGCGTTCGAGCTCGACGACGGGTTCAGGTTCGGCGGGATGGAC

GCCGGGTCGTACTACGCGAGCTTGGCGCAGGGGCTGCTCGTCGAGCCGCCGGCCGCCGGA

GCGTGGTGGAGGACGGCGAGCTCGCCGGCTCCGACATGCCGCTCTGGAGCTACTAA

Protein >12009.m06501

(SEQ ID NO: 6)
MEVEEAAYRTVWSEPPKRPAGRTKFRETRHPVYRGVRRRGGRPGAAGRWVCEVRVPGARG

SRLWLGTFATAEAAARAHDAAALALRGRAACLNFADSAWRMPPVPASAALAGARGVRDAV

AVAVEAFQRQSAAPSSPAETFANDGDEEEDNKDVLPVAAAEVFDAGAFELDDGFRFGGMD

AGSYYASLAQGLLVEPPAAGAWWEDGELAGSDMPLWSY*

OsDREB1C (dehydration-responsive element-binding protein
1C)LOC_Os06g03670
CDS >13106.m00305

(SEQ ID NO: 7)
ATGGAGTACTACGAGCAGGAGGAGTACGCGACGGTGACGTCGGCGCCGCCGAAGCGGCCG

GCGGGGAGGACCAAGTTCAGGGAGACGAGGCACCCGGTGTACCGCGGCGTGCGGCGGCGG

GGGCCCGCGGGGCGGTGGGTGTGCGAGGTCAGGGAGCCCAACAAGAAGTCCCGCATCTGG

CTCGGCACCTTCGCCACCGCCGAGGCCGCCGCGCGCGCCCACGACGTCGCCGCGCTCGCC

CTCCGCGGCCGCGGCGCGTGCCTCAACTTCGCCGACTCGGCCCGCCTCCTCCGCGTCGAC

CCGGCCACCCTCGCCACCCCCGACGACATCCGCCGCGCCGCCATCGAGCTCGCCGAGTCA

TGCCCGCACGACGCCGCCGCCGCCGCCGCCTCCAGCTCCGCCGCCGCCGTCGAGGCCTCC

GCCGCCGCCGCGCCCGCCATGATGATGCAGTACCAGGACGACATGGCGGCGACGCCGTCC

AGCTACGACTACGCGTACTACGGCAACATGGACTTCGACCAGCCGTCCTACTACTACGAC

GGGATGGGCGGCGGCGGCGAGTACCAGAGCTGGCAGATGGACGGCGACGACGATGGTGGC

GCCGGCGGCTACGGCGGCGGCGACGTCACACTCTGGAGCTACTGA

Protein >13106.m00305

(SEQ ID NO: 8)
MEYYEQEEYATVTSAPPKRPAGRTKFRETRHPVYRGVRRRGPAGRWVCEVREPNKKSRIW

LGTFATAEAAARAHDVAALALRGRGACLNFADSARLLRVDPATLATPDDIRRAAIELAES

CPHDAAAAASSSAAAVEASAAAAPAMMMQYQDDMAATPSSYDYAYYGNMDFDQPSYYYD

GMGGGGEYQSWQMDGDDDGGAGGYGGGDVTLWSY*

-continued

OsDREB1D (dehydration-responsive element-binding protein
1D)LOC_Os06g06970
CDS >13106.m00721
(SEQ ID NO: 9)
ATGGAGAAGAACACCGCCGCCAGCGGGCAATTGATGACCTCCTCCGCGGAGGCGACGCCG

TCGTCGCCGAAGCGGCCGGCGGGGCGAACCAAGTTCCAGGAGACGAGGCACCTAGTGTTC

CGTGGGGTGCGATGGCGTGGGTGCGCGGGGCGGTGGGTGTGCAAGGTGCGTGTCCCGGGC

AGCCGCGGTGACCGTTTCTGGATAGGCACGTCTGACACCGCCGAGGAGACCGCGCGCACG

CACGACGCCGCCATGCTCGCCTTGTGCGGGGCCTCCGCCAGCCTCAACTTCGCCGACTCT

GCCTGGCTGCTCCACGTCCCGCGCGCCCCCGTCGTCTCCGGACTCCGGCCACCAGCTGCC

CGATGTGCAACGCGCTGCCTGCAAGGCCATCGCCGAGTTCCAGCGCCGGGCCGGGGAGC

ACCGCCACTGCCACTGCCACCTCCGGCGATGCTGCATCGACCGCTCCTCCGTCGGCACCC

GTTCTGTCAGCCAAACAATGCGAATTCATCTTTCTTTCTTCACTAGATTGTTGGATGTTA

ATGTCAAAGCTTATCAGCAGTAGCAGAGCAAAAGGATCGTTGTGCCTGCGAAAAAATCCC

ATTTCATTTTGCATGGTTACAAATTCTTACACTGCTCTTTTGCTCGAATACATTATATTG

CAGATGAATTCAATGATCGTTTTAATCCACGAATTATCAAAATATCAAGTCTTTCTGCTA

CTAACCATGATAACACACCACCTTTTTCAATGGAGGAGGTAG

Protein >13106.m00721
(SEQ ID NO: 10)
MEKNTAASGQLMTSSAEATPSSPKRPAGRTKFQETRHLVFRGVRWRGCAGRWVCKVRVPG

SRGDRFWIGTSDTAEETARTHDAAMLALCGASASLNFADSAWLLHVPRAPVVSGLRPPAA

RCATRCLQGHRRVPAPGRGSTATATATSGDAASTAPPSAPVLSAKQCEFIFLSSLDCWML

MSKLISSSRAKGSLCLRKNPISFCMVTNSYTALLLEYIILQMNSMIVLIHELSKYQVFLL

LTMITHHLFQWRR*

The above-mentioned level of wild type MYBS3 or DREB1 protein can be the MYBS3 or DREB 1 gene expression level in a wild type cell of a wild type plant. To achieve this overexpression, the genes can be under the control of native, constitutive, tissue-specific, developmental stage-specific, or other inducible promoters.

The above-described transgenic plant can be rice, maize, wheat, barley, sorghum, sugarcane, turf grass, Miscanthus, switchgrass, soybean, canola, potato, tomato, bean, pea, or jatropha. The transgenic plant is more tolerant to chill than the wild type plant.

In a second aspect, the invention features a method of generating the above-described plant. The method includes steps of introducing into a cell of a plant a first nucleic acid that encodes a polypeptide containing the amino acid sequence of MYBS3 protein; and expressing the MYBS3 protein in the cell. The level of the MYBS3 protein in the cell is higher than a wild type MYBS3 protein level. In one embodiment, the method further includes introducing into the cell of the plant a second nucleic acid that encodes a second polypeptide containing the amino acid sequence of DREB1 protein; and expressing the DREB1 protein in the cell. The level of the DREB1 protein in the cell is higher than a wild type DREB1 protein level.

In a third aspect, the invention features a method of identifying a plant that is tolerant to chill. The method can be carried out by obtaining a sample from a candidate plant, and determining the MYBS3 gene expression level in the sample. The candidate plant is determined to be tolerant to chill if the expression level is above a predetermined level. The predetermined level is the level in a wild type plant. With this method, one can use MYBS3 as a marker for molecular breeding plants and selecting chill tolerant plants.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Figure 5:
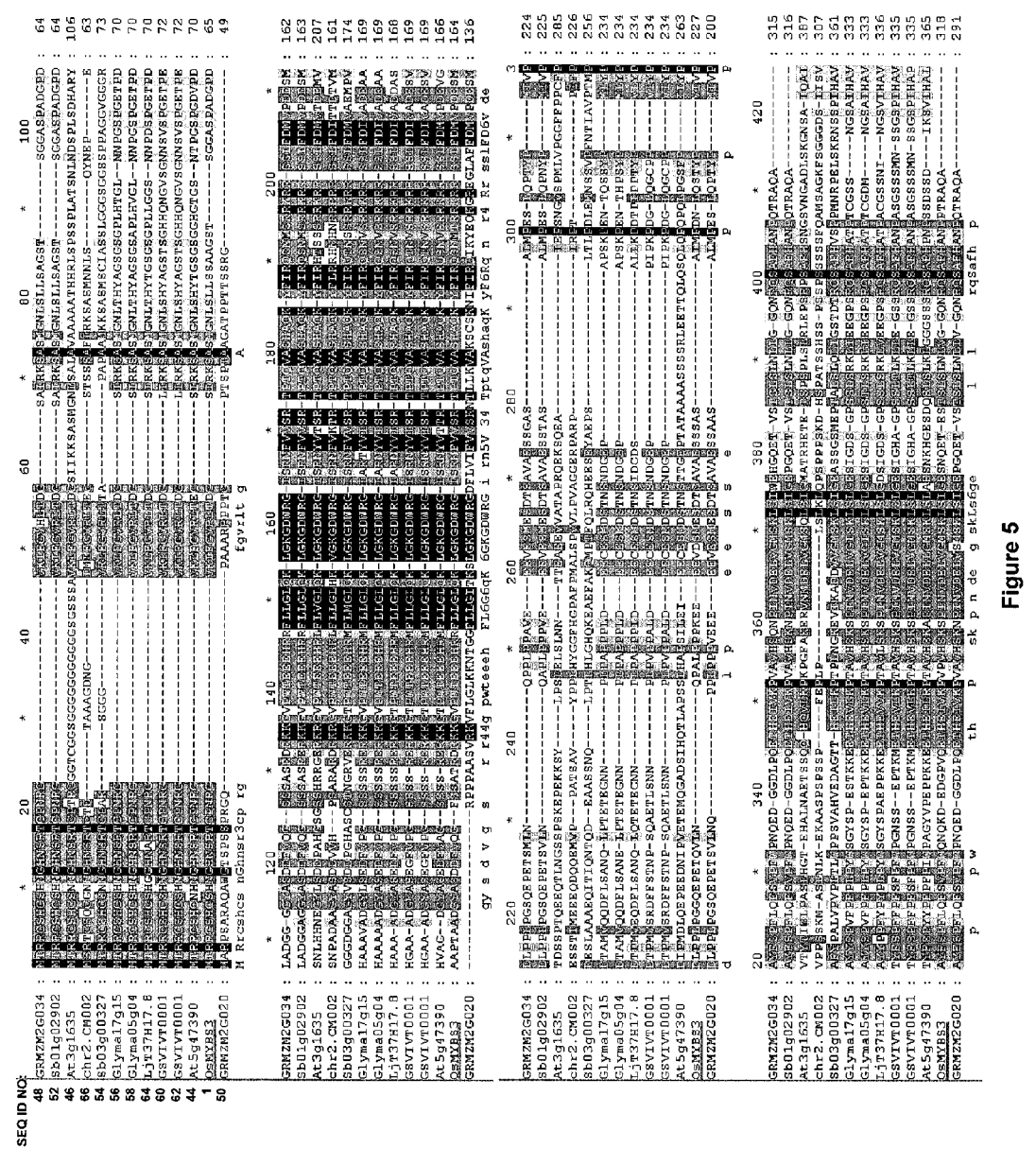

FIG. 5 is a sequence alignment of thirteen MYB3 proteins, one from rice and two from each of *Arabidopsis thaliana, Zea May*, sorghum, soybean, twine grape, and lotus.

DETAILED DESCRIPTION

Figure 1:
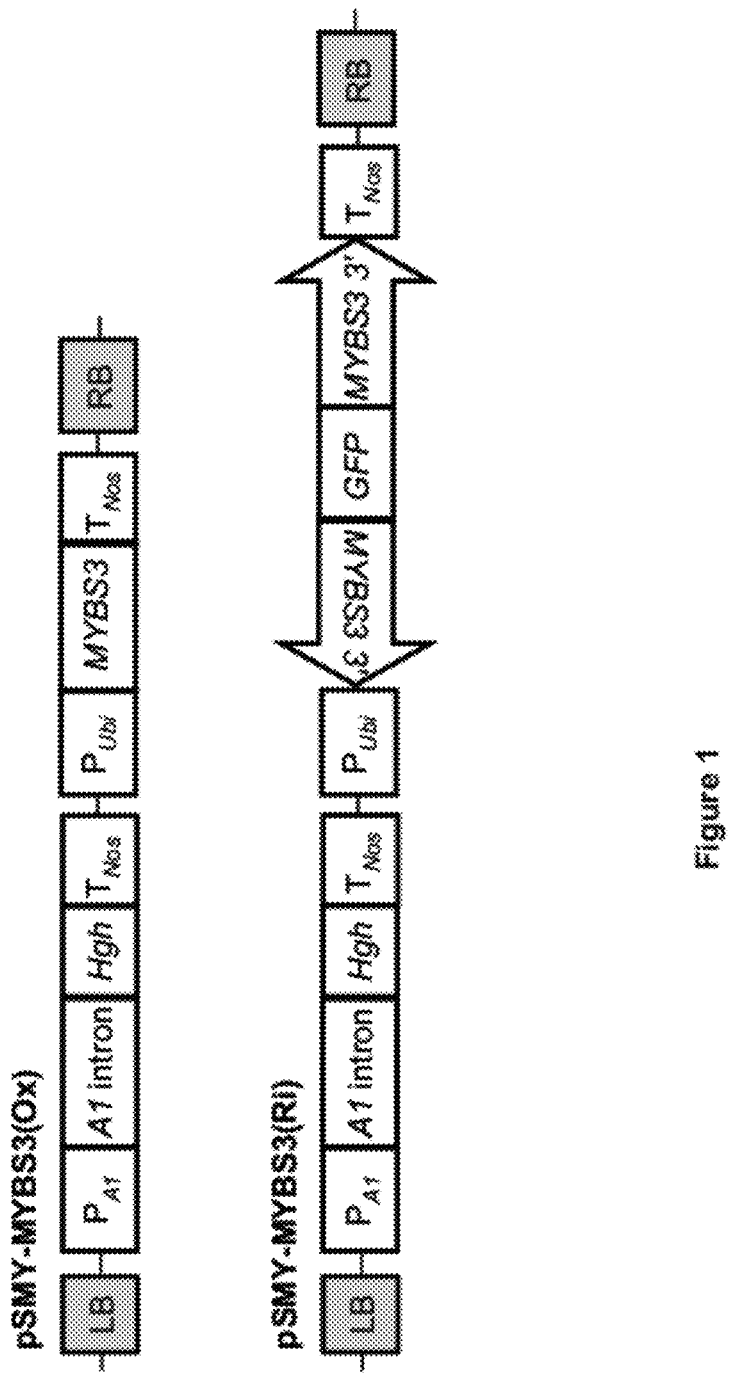
FIG. 1 shows two constructs for respectively over-expressing and under-expressing MYBS3 in transgenic rice; namely, pSMY-MYBS3(Ox), an over-expression construct; and pSMY-MYBS3(Ri), an under-expression construct. $P_{A1}$, Hgh, $T_{Nos}$, $P_{Ubi}$, LB, and RB denote A1 promoter, hygromycin phosphotransferase, nopalin synthase terminator, Ubi promoter, left border of T-DNA, and right border of T-DNA, respectively.

This invention is based, at least in part, on the unexpected discoveries of that over-expression of MYBS3 in a plant increased the cold tolerance.

MYBS3 is a single DNA-binding repeat (1R) MYB transcription factor previously shown to mediate sugar signaling in rice. MYBS3 also plays a critical role in cold adaptation in rice. Gain- and loss-of-function analyses indicates that MYBS3 is sufficient and necessary for enhancing cold tolerance in rice. Transgenic rice constitutively over-expressing MYBS3 tolerates 4° C. for at least 1 week, and exhibits no yield penalty in normal field conditions. Transcription profiling of transgenic rice over- or under-expressing MYBS3 lead to identification of many genes in the MYBS3-mediated cold signaling pathway. Several genes activated by MYBS3 as well as inducible by cold have previously been implicated in various abiotic stress response and/or tolerance in rice and other plant species. Surprisingly, MYBS3 represses the well-known DREB1/CBF-dependent cold signaling pathway in rice, and the repression appears to act at the transcriptional level. DREB1 responds quickly and transiently while MYBS3 responds slowly to cold stress, which suggests distinct pathways act sequentially and complementarily for adapting short- and long-term cold stress in rice. This novel pathway, which controls cold adaptation in rice as well as other plants, forms the basis for this invention.

A transgenic plant described in the invention can be generated by introducing into the plant or a part thereof an expression construct comprising a DNA sequence encoding a MYB3 protein, a DREB1 protein, or both. Expression constructs are provided by the present invention for the stable transformation of plants with a gene encoding a MYB3 protein, a DREB1 protein, or both. These constructs comprise a DNA sequence encoding a MYB3 protein or a DREB1 protein which is operably linked to regulatory sequences which are capable of directing the expression of a MYB3 protein, a DREB1 protein, or both. These regulatory sequences may also include sequences capable of directing transcription in plants, either constitutively, or stage and/or tissue specific, depending on the use of the plant or parts thereof. The expression constructs provided may be inserted into a vector, preferably a plasmid, used in bacteria-mediated transformation of the selected plant host. The expression construct is then preferably integrated into the genome of the plant host.

A transgene is a nucleic acid sequence (encoding, e.g., one or more subject polypeptides), which is partly or entirely heterologous to a plant cell into which it is introduced, or, is homologous to an endogenous gene of the plant or cell into which it is introduced but is intended to be inserted into the plant genome in such a way as to alter the genome (e.g., it is inserted at a location which differs from that of the natural gene or its insertion results in a knockout). A transgene can include one or more operably linked transcriptional regulatory sequences (e.g., an enhancer sequence) and any other nucleic acid, such as an intron, that may be necessary for optimal expression of a nucleic acid of interest.

A "transformed" and "transgenic cell refer to a host cell or organism into which a heterologous nucleic acid molecule has been introduced. The nucleic acid molecule can be stably integrated into the genome generally known in the art. Accordingly, a transgenic cell is a cell containing a transgene. A transgenic plant is any plant in which one or more, or all, of the cells of the plant include a transgene. The transgene can be introduced into the cell by introduction into a precursor cell by way of deliberate genetic manipulation, such as by T-DNA mediated transfer, electroporation, or protoplast transformation. The transgene may be integrated within a chromosome, or it may be an extrachromosomally replicating DNA.

The term "heterologous" refers to portions of a nucleic acid and indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extra-chromosomal nucleic acid. In contrast, a naturally translocated piece of chromosome would not be considered heterologous in the context of this patent application, as it comprises an endogenous nucleic acid sequence that is native to the mutated cell. A heterologous nucleic acid, gene, or protein can be one that originates from a foreign species, or, if from the same species, is substantially modified from its original form. For example, a maize ubiquitin (Ubi) promoter operably linked to a nucleic acid sequence encoding a rice MYB3 protein is one form of a sequence heterologous to rice. If a promoter and a coding sequence are from the same species, one or both of them can be substantially modified from their original forms.

Rice is one of the most important food crops in the world, and increases in rice yield could significantly ease the pressure on world food production. Rice is also a powerful model for functional genomics study for dissecting genetic networks of stress responses in cereal crops. Low temperatures are one of the major environmental stresses that adversely affect rice productivity in temperate and subtropical zones and in high elevation areas. Rice seedlings are particularly sensitive to chilling in early spring in these areas, leading to slow seedling development, yellowing, withering, reduced tillering and stunted growth (Andaya, et al., 2003, J Exp Bot 54: 2579-2585). Rice cannot be grown in approximately 7,000,000 hectares of land in south and south-east Asia due to cold stress (Sthapit, et al., 1998, Crop Sci 38: 660-665); in temperate regions such as California (USA), cold is an important stress that results in delayed heading and yield reduction due to spikelet sterility (Peterson, et al., 1974, California Agriculture, 28(7), 12-14). Thus, improvement of chilling tolerance may significantly increase rice production.

Plants respond and adapt to cold stress at the molecular and cellular levels as well as induce an array of biochemical and physiological alterations that enable them to survive (Bohnert et al., 1995, Cell 7: 1099-1111; and Browse, et al., 2001, Curr Opin Plant Biol 4: 241-246). Under cold stress, the expression of many genes is induced in various plant species (Hughes, et al., 1996, J Exp Bot 47: 291; and Thomashow, 1999, Annu Rev Plant Physiol Plant Mol Biol 50: 571-59), and the products of these genes function not only in adaptations promoting stress tolerance, e.g., biosynthesis of osmotica (Chen, et al., 2002, Curr Opin Plant Biol 5: 250-257; and Taji, et al., 2002, Plant J 29: 417-426), generation of antioxidants (Prasad, et al., 1994, Plant Cell 6: 65-74), and increased membrane fluidity (Murata and Los, 1997, Plant Physiol 115: 875-879; and Orvar, et al., 2000, Plant J 23: 785-794), but also in the regulation of gene expression and signaling transduction in stress responses, e.g., transcription factors and proteins involved in RNA processing and nuclear export (Yamaguchi-Shinozaki, et al., 2006, Annu Rev Plant Biol 57: 781-803; and Chinnusamy, et al., 2007, Trends Plant Sci 12: 444-451). Deciphering the mechanisms by which plants perceive and transmit cold signals to cellular machinery to activate adaptive responses is of critical importance for developing breeding strategies to enhance cold stress tolerance in crops.

In *Arabidopsis* and rice, the CBF/DREB1-dependent cold response pathway has been shown to play a predominant role in freezing-tolerance through the process of cold acclimation (Thomashow, 1999, Annu Rev Plant Physiol Plant Mol Biol 50: 571-59; Yamaguchi-Shinozaki, et al., 2006, Annu Rev Plant Biol 57: 781-803; and Chinnusamy, et al., 2007, Trends Plant Sci 12: 444-451). The DREB1/CBF family, including DREB1A/CBF3, DREB1B/CBF1, and DREB1C/CBF2, are able to bind to and activate the cis-acting elements DRE (dehydration-responsive element) (Yamaguchi-Shinozaki, et al., 1994, Plant Cell 6: 251-264; and Stockinger, et al., 1997, Proc Natl Acad Sci USA 94: 1035-104) or CRT (C-repeat) (Baker, et al., 1994, Plant Mol Biol 24: 701-713) on promoters of several cold-responsive genes (CORs) (Gilmour, et al., 1998, Plant J 16: 433-442; Jaglo-Ottosen, et al., 1998, Science 280: 104-106; Liu, et al., 1998, Plant Cell 10: 1391-1406; Medina, et al., 1999, Plant Physiol 119: 463-470).

Rice DREB1A and DREB1B are induced by cold stress, and constitutive over-expression of these genes leads to induction of stress-responsive genes, increased tolerance to high-salt and cold, and growth retardation under normal conditions in transgenic *Arabidopsis* and rice (Dubouzet, et al., 2003, Plant J 33: 751-763; and Ito, et al., 2006, Plant Cell Physiol 47: 141-153), indicating the evolutionary conservation of the DREB1/CBF cold-responsive pathway in monocots and dicots. However, in comparison to *Arabidopsis* and other cereals like wheat and barley that cold acclimate (Wen, et al., 2002, Plant Physiol 129: 1880-1891), rice does not undergo acclimation process and is more sensitive to low temperature exposures. Microarray analysis demonstrated the existence of 22 cold-regulated genes in rice, which have not been reported in *Arabidopsis* (Rabbani, et al., 2003, Plant Physiol 133: 1755-1767). These studies also indicate that plant species vary in their abilities to adapt to cold stress.

Other rice proteins have also been shown to be involved in cold tolerance. For example, a zinc-finger protein iSAP1 confers cold, dehydration, and salt tolerance in transgenic tobacco (Mukhopadhyay, et al., 2004, Proc Natl Acad Sci USA 101: 6309-6314); the rice MYB4 transcription factor confers chilling and freezing tolerances by enhancing the COR gene expression and proline accumulation in *Arabidopsis* (Vannini, et al., 2004, Plant J 37: 115-127), and improves cold and drought tolerances by accumulating osmolyte in transgenic apples (Pasquali, et al., 2008, Plant Cell Rep 27: 1677-1686). Overexpression of the rice cold-, drought-, and salt-inducible MYB3R-2 (an R1R2R3 MYB) gene enhances cold, drought, and salt tolerance by regulating some stress-responsive genes involved in the CBF-dependent or CBF-independent pathways in *Arabidopsis* (Dai, et al., 2007, Plant Physiol 143: 1739-1751; and Ma, et al., 2009, Plant Physiol 150: 244-256).

The expression of DREB1 is subjected to regulation by several factors. For example, it is affected by members in the same DREB1 family. The *Arabidopsis* cbf2 mutant, in which CBF2/DREB 1 C is disrupted, shows higher freezing, dehydration and salt tolerance than the wild-type plant, indicating that DREB1C/CBF2 acts as a repressor of CBF1/DREB1B and CBF3/DREB1A expression (Novillo, et al., 2004, Proc Natl Acad Sci USA 101: 3985-3990). The expression of DREB1/CBF is activated by Inducer of CBF Expression 1, ICE1 (a MYC-like basic helix-loop-helix-type transcription factor) (Chinnusamy, et al., 2003, Genes Dev 17: 1043-1054), CAX1 (a $Ca^{2+}/H^+$ transporter) (Catala, et al., 2003, Plant Cell 15: 2940-2951), CBL1 (a $Ca^{2+}$ sensor) (Albrecht, et al, 2003, Plant J 36: 457-470), and LOS4 (a DEAD-box RNA helicase) (Gong, et al., 2002, Proc Natl Acad Sci USA 99: 11507-11512), and repressed by FRY2 (a transcription factor) (Xiong, et al., 2002, Proc Natl Acad Sci USA 99: 10899-1090), HOS1 (a putative RING finger E3 ligase) (Lee, et al., 2001, Genes Dev 15: 912-924), and ZAT12 (a $C_2H_2$ zinc finger transcription factor) (Vogel, et al., 2005, Plant J 41: 195-211), during cold acclimation in *Arabidopsis*. The mechanism by which these factors affect the expression of CBF/DREB1 is not clear.

Previously, three MYB transcription factors, MYBS1, MYBS2, and MYBS3 each with a single DNA binding domain (1R MYB), were identified in rice and shown to bind specifically to the TA box (TATCCA) in the sugar response complex (SRC) of α-amylase gene (αAmy3) promoter (Lu, et al., 2002, Plant Cell 14: 1963-1980). MYBS1 and MYBS2 transactivate, while MYBS3 represses, the sugar starvation-inducible αAmy3 SRC activity in rice (Lu, et al., 2002, Plant Cell 14: 1963-1980). The rice MYBS3 homologue in *Arabidopsis* (AGI code: At5g47390) is activated by ABA, $CdCl_2$ and NaCl (Yanhui, et al., 2006, Plant Mol Biol 60: 107-124). It is unexpected that the expression of MYBS3 is induced by cold. By both gain- and loss-of-function analyses, MYBS3 is shown essential for cold stress tolerance in rice. Transcription profiling of transgenic rice over- or under-expressing MYBS3 led to identification of genes that are activated or repressed by MYBS3 and play diverse functions. The DREB1-dependent cold response signaling pathway is among those repressed by MYBS3 in rice. This finding suggests that the DREB1- and MYBS3-dependent pathways may complement each other and act sequentially to adapt to immediate and persistent cold stress in rice.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE

Materials and Methods
Plant Materials

The rice cultivar *Oryza sativa* L. cv. Tainung 67 was used in this study. Induction of rice calli was performed as described (Yu, et al., 1991, J Biol Chem 266: 21131-21137). For hydroponic culture of rice seedlings, seeds were sterilized with 3% NaOCl for 30 min, washed extensively with distilled water, and germinated in Petri dishes with wetted filter papers at 37° C. in the dark. After 48 h incubation, germinated seeds were cultivated in a half-strength Kimura B solution containing the following macronutrients: $(NH4)_2SO_4$ (0.18 mM), $KNO_3$ (0.09 mM), $MgSO_4$ (0.27 mM), $KH_2PO_4$ (0.09 mM), and $Ca(NO_3)_2$ (0.18 mM), and micronutrients: Fe-citrate (0.03 μM), $H_3BO_3$ (2.5 μM), $MnSO_4.H_2O$ (0.2 μM), $ZnSO_4.7H_2O$ ($0.2 \mu M$), $CuSO_4 \cdot 5H_2O$ ($0.05 \mu M$), and $H_2MoO_4$ ($0.05 \mu M$). The pH of the solution was adjusted to 4.7-4.8 using 0.5 N HCl. The culture solution was replaced with fresh solution every 2 days. Seedlings were grown under a 14-h light/10-h dark cycle for 10 days in a 28° C. chamber before treatments.

Primers

All primers used for the cloning of cDNAs or plasmid constructions and quantitative RT-PCR are listed in Table 1 below.

TABLE 1

Primers

| Target gene | Primer | Annealing temperature (° C.) | Fragment size (bp) |
|---|---|---|---|
| MYBS3 | S3F1: 5'-CCT TTCTGGCAA AATCAG AAAGA-3' (SEQ ID NO: 11)<br>S3R1: 5'-ATG AACTGG AACAGGCTTGACA-3' (SEQ ID NO: 12) | 60 | 78 |
| MYBS3 promoter | S3PF: GCGGATCCCCTTTTGACTTGCAGGTTAATTACTTCAGG (SEQ ID NO: 13)<br>S3PR: CATGCCATGGTTTAAACCCCCCCTCCGTCCCTCCACCTTCC (SEQ ID NO: 14) | 68 | 2500 |
| DREB1A | 1AF: 5'-GGACCTGTACTACGCGAGCTT-3' (SEQ ID NO: 15)<br>1AR: 5'-GGCAAAATTGTACAGTTGATTGA-3' (SEQ ID NO: 16) | 60 | 138 |
| DREB1A promoter | 1APro: 5'-TTGACCGGGATACCGAATTA-3' (SEQ ID NO: 17)<br>1APro: 5-GTAATGGCGATGGGAGAAGA-3' (SEQ ID NO: 18) | 60 | 1054 |
| DREB1B | 1BF: 5'-AGCTCGCCGGCTCCGACA-3' (SEQ ID NO: 19)<br>1BR: 5'-GGGAGAAATCTGGCACATTCC-3' (SEQ ID NO: 20) | 60 | 194 |
| DREB1B promoter | 1BPro: 5'-AGGTAAGCCATTAGCGCATG-3' (SEQ ID NO: 21)<br>1BPro: 5'-GGATGACTCTCTCTGGTTCA-3' (SEQ ID NO: 22) | 60 | 747 |
| DREB1C | 1CF: 5'-GAGTTGGAGCTAGCAGTTTTGAG-3' (SEQ ID NO: 23)<br>1CR: 5'-TAGCTGTATAGGAGGAGCAAAGC-3' (SEQ ID NO: 24) | 60 | 54 |
| Amy3 | Amy3F: 5'-GTAGGCAGGCTCTCTAGCCTCTAGG-3' (SEQ ID NO: 25)<br>Amy3R: 5'-GTAGGCAGGCTCTCTAGCCTCTAGG-3' (SEQ ID NO: 26) | 60 | 112 |
| Cytochrome P450 | CytF: 5'-GTCATCCAGGAGACGATGAGG-3' (SEQ ID NO: 27)<br>CytR: 5'-GATGTTGCGGAACAGAGGTAG-3' (SEQ ID NO: 28) | 60 | 129 |
| 18S rRNA | 18SF: 5'-CCTATCAACTTTCGATGGTAGGATA-3' (SEQ ID NO: 29)<br>18SR: 5'-CGTTAAGGGATTTAGATTGTACTCATT-3' (SEQ ID NO: 30) | 60 | 229 |
| Trehalose-6-phosphate phosphatase 1 gene (Os02g44230) | T6PP1 F: 5'-GGAGTTCCTCAATTTCTTGGTG-3' (SEQ ID NO: 31)<br>T6PP1 R: 5'-CGCCTCGGAAACTACAGTTATT-3' (SEQ ID NO: 32) | 60 | 116 |
| Trehalose-6-phosphate phosphatase 2 gene (Os10g40550) | T6PP F: 5'-AGGATGCATTCAAGGTTCTGA-3' (SEQ ID NO: 33)<br>T6PP R: 5'-CAAGATGCCAGTTTCTTCAGG-3' (SEQ ID NO: 34) | 60 | 139 |
| GFP | GFP_F: 5'-CCTGTCCTTTTACCAGACAACC-3' (SEQ ID NO: 35)<br>GFP_R: 5'-GGACCATGTGGTCTCTCTTTTC-3' (SEQ ID NO: 36) | 60 | 85 |
| Multidrug-resistantce (Os01g50100) | MRT_F: 5'-CAGGCAGAGGAACAGGTGAT-3' (SEQ ID NO: 37)<br>MRT_R: 5'-CGTACCGGAACAAGCTGAAC-3' (SEQ ID NO: 38) | 60 | 108 |
| Glutamate decarboxylase (Os03g13300) | GD_F: 5' AAGACGCTGCTGATTGATATGAT-3' (SEQ ID NO: 39)<br>GD_R: 5'-TGGTAGCTCACACCATGAATGTA-3' (SEQ ID NO: 40) | 60 | 50 |
| WRKY77 (Os01g40260) | WRKY77_F: 5'-GGAATGGACAATTAGTTTGTCTCC-3' (SEQ ID NO: 41)<br>WRKY77_R: 5'-ATATATCGATGGGCCGTAATTTT-3' (SEQ ID NO: 42) | 60 | 73 |

Plasmid Construction

The GATEWAY gene cloning system (Invitrogen, Carlsbad, CA) was used to construct the MYBS3-GFP fusion gene. Briefly, the full-length cDNA of MYBS3 was inserted between the attL1 and attL2 sites in pENTR/D-TOPO, generating the entry vector pENT-MYBS3. The CaMV35S promoter upstream of GFP in pCAMBIA1302 (see the website at cambia.org.au/daisy/cambia/585.html) was replaced with the maize ubiquitin (Ubi) promoter, and the ccdB DNA fragment flanked by attR1 and attR2 sties was inserted between the Ubi promoter and GFP, generating the destination vector pDEST-GFP. MYBS3 in pENT-MYBS3 was then inserted upstream of GFP in pDEST-GFP through the GATEWAY lambda recombination system, generating p1302-MYBS3-GFP. The 2.5-kb MYBS3 promoter fragment (upstream of ATG) was PCR synthesized and used for replacement of the Ubi promoter in pDEST-GFP, generating the Ubi::MYBS3-GFP construct.

For generating constructs used for the embryo transient expression assay, the 1054-bp DREB1A and 747-bp DREB1B promoters (upstream of ATG) were PCR-synthesized and fused upstream of Luc cDNA in pLuc (Lu, et al., 1998, J Biol Chem 273: 10120-10131). Plasmid p3Luc.18 contains αAmy3 SRC (−186 to −82 upstream of the transcription start site) fused to the CaMV35S minimal promoter-Adh intron-Luc fusion gene (Lu, et al., 1998, J Biol Chem 273: 10120-10131).

For generating constructs used for rice transformation, plasmid pBS-MYBS3 (Lu, et al., 2002, Plant Cell 14: 1963-1980) containing the Ubi promoter fused upstream of MYBS3 cDNA was linearized with EcoRI and inserted into the binary vector pSMY1H (Ho, et al., 2000, Plant Physiol 122: 57-66), generating pSMY-MYBS3 (FIG. 1). To make the MYBS3 RNA interference construct, a 227-bp sequence derived from the 3'UTR of MYBS3 cDNA was synthesized by PCR, fused in antisense and sense orientations flanking the 750-bp GFP cDNA. This MYBS3 RNAi fragment was used to replace the MYBS3 cDNA in pUbi-MYBS3, generating pUbi-MYBS3(Ri). pUbi-MYBS3(Ri) was linearized with EcoRI and inserted into the binary vector pSMY1H, generating pSMY-MYBS3(Ri) (FIG. 1).

Rice Transformation

Plasmids p1302-MYBS3-GFP, pSMY-MYBS3, pSMY-MYBS3(Ri) as constructed above were introduced into *Agrobacterium tumefaciens* strain EHA101, and rice transformation was performed as described elsewhere (Ho, et al., 2000, Plant Physiol 122: 57-66).

RNA Extraction and Real-Time Quantitative RT-PCR Analysis

Total RNA was extracted from leaves of rice seedlings with Trizol reagent (Invitrogen) and treated with RNase-free DNase I (Promega, Madison, Wis.). Four μg of RNA was used for cDNA preparation with reverse transcriptase (Applied Biosystems, Foster City, Calif.), and cDNA was then diluted to 10 ng/μl. Five μl of cDNA was mixed with primers and the 2× Power SYBR Green PCR Master Mix reagent, and applied to an ABI 7500 Fast Real-Time PCR System (Applied Biosystems). The quantitative variation between different samples was evaluated by the delta-delta CT method, and the amplification of 18S ribosomal RNA was used as an internal control to normalize all data.

Subcellular Localization of MYBS3-GFP Fusion Protein

Protoplasts were isolated from transformed calli as described (Lu, et al., 1998, J Biol Chem 273: 10120-10131). GFP expression was detected under a LSM510 confocal laser scanning microscope (Carl Zeiss) using a 40× objective lens and the confocal microscopy software Release 2.8 (Carl Zeiss).

Stress Treatments

Ten-day-old seedlings cultured in the half-strength Kimura B solution at 28° C. and with 16-h light and 8-h dark cycle in a growth chamber were used for all stress treatments. Stress treatments are as follows: ABA, seedlings were transferred to a culture solution containing 20 μM ABA; drought, seedlings were air-dried until 10% or 30% of fresh weight was lost; cold, seedlings were transferred to 4° C.; salt, seedlings were transferred to a culture solution containing 200 mM NaCl; heat, seedlings were transferred to 45° C.

Microarray Analysis

Total RNA was extracted from leaves of rice seedlings using the Qiagen RNeasy Plant Mini Kits (Qiagen, Valencia, Calif.) according to the Qiagen manual. RNA quality was examined by the Agilent 2100 bioanalyzer (Affymetrix, Palo Alto, Calif.), and biotinylated target RNA was prepared from total RNA. Samples were hybridized to the Affymetrix Rice GeneChip (Affymetrix, Santa Clara, Calif.) as described in the GeneChip Expression Analysis Technical Manual. Two biological replicates were performed for cold treated samples per time point.

The hybridization signals were scanned with an Affymetrix GeneChip scanner 3000 7G, and the cell intensity (CEL) files were obtained from software Affymetrix GCOS version 1.4 (Affymetrix). CEL files were loaded into GeneSpring GX 9.0 (Agilent Technologies, Palo Alto, Calif.). Filtering tools in the GeneSpring software were used to identify genes significantly up-regulated and down-regulated between different chips. All genes up-regulated or down-regulated by over-expression or under-expression of MYBS3 or by cold are listed in Tables S7-S11 of Su, et al, Plant Physiol. 2010; 153(1):145-58.

Accession Number

DREB1A (Os09g35030); DREB1B (Os09g35010); DREB1C (Os06g03670); αAmy3/RAmy3D (Os08g36910); Cytochrome P450 gene (Os02g47470); Glutamate decarboxylase gene (Os03g13300); WRKY77 (Os01g40260); Multidrug resistance protein 4 gene (Os01g50100); Trehalose-6-phosphate phosphatase 1 gene (Os02g44230); and Trehalose-6-phosphate phosphatase 2 gene (Os10g40550).

Results

Expression of MYBS3 is Ubiquitous and Activated by Cold Stress

Figure 2:
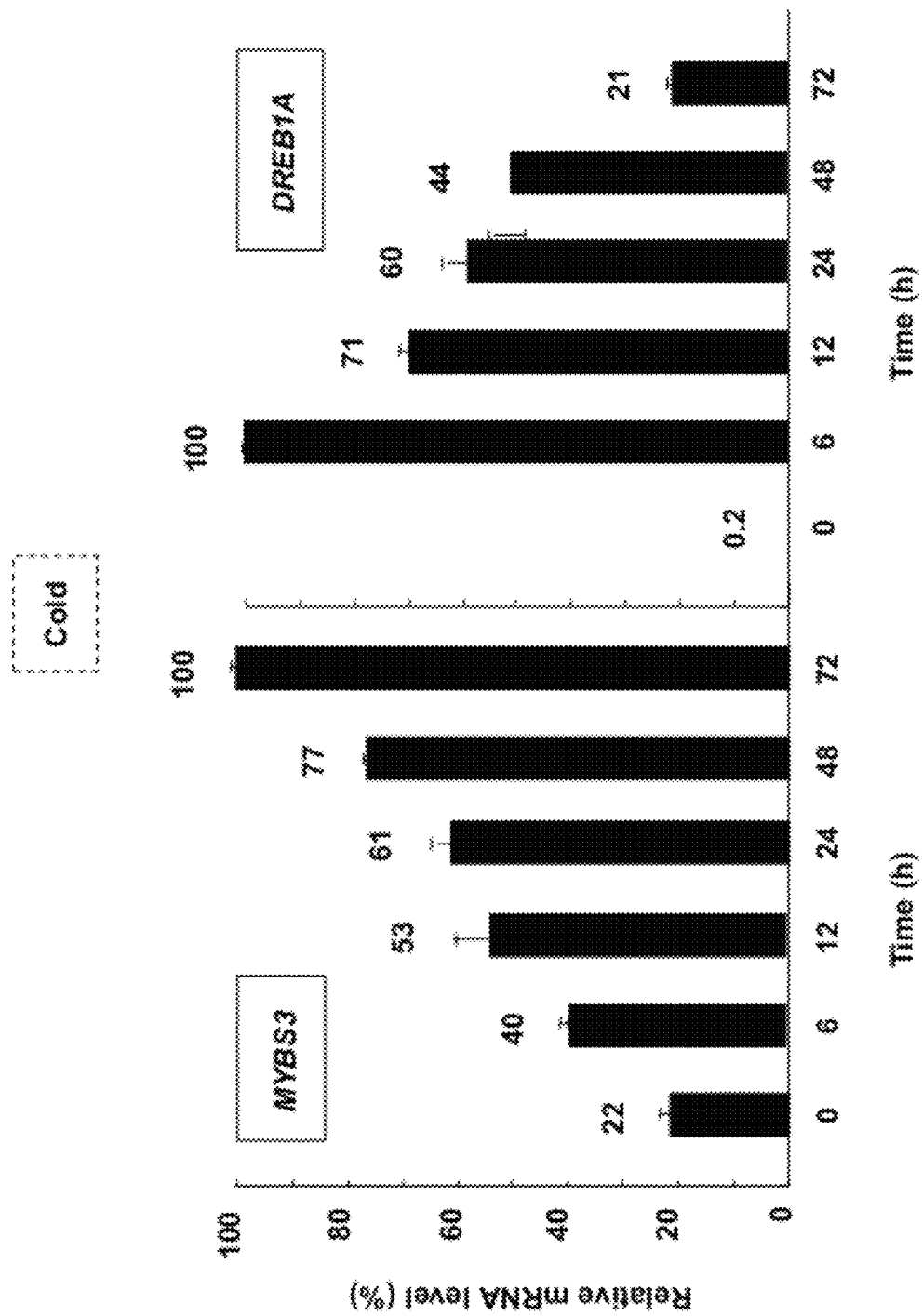
FIG. 2 is a bar graph showing expression of MYBS3 and DREB1A in 10-day-old rice seedlings that were shifted from 28° C. to 4° C. and incubated for 72 h. Total RNAs were isolated from seedlings and subjected to quantitative real-time RT-PCR analysis. The highest mRNA level was assigned a value of 100, and the mRNA levels of other samples were calculated relative to this value. The error bars indicate the SE of three replicates.

Expression of MYBS3 was found to be ubiquitous in all tissues in 7-day-old seedlings and 3-month-old mature plants (including spike, stem, sheath, leaf, senescent leaf, leaf in light, root in light, leaf in dark, and root in dark) and in suspension cells of rice cultured in media with or without sucrose for 2 days. The regulation of MYBS3 expression by various stresses was investigated by subjecting 10-day-old rice seedlings to ABA (20 μM), drought (air dry), cold (4° C.), salt (200 mM NaCl), and heat (45° C.) treatments. The accumulation of MYBS3 mRNA was induced by cold in roots and by cold and salt in shoots, but reduced by ABA in shoots. In 10-day-old rice seedlings, the expression pattern of MYBS3 and DREB1A under cold stress was further compared. The amount of MYBS3 mRNA was detectable at 28° C., and increased 5-fold at 4° C. after 72 h; in contrast, the accumulation of DREB1A mRNA was barely detectable at 28° C., increased drastically after shifting to 4° C. and peaked at 6 h, but declined to one fifth after 72 h (FIG. 2).

To determine whether MYBS3 is regulated by cold at the transcriptional level, the 2.5-kb MYBS3 promoter was fused to the reporter gene GFP encoding a green fluorescence protein and introduced into the rice genome. Ubi promoter fused to GFP was used as a control. Transgenic rice seedlings were grown at 4° C. Under the control of MYBS3 promoter, the accumulation of GFP mRNA was 2.5 times higher at 12 h and stayed high up to 24 h. In contrast, under the control of Ubi promoter, the accumulation of GFP mRNA decreased by nearly 50% at 6 h, and then stayed at similar levels up to 24 h. This result indicates that the MYBS3 promoter is activated by cold.

MYBS3 is a transcriptional repressor of αAmy3 SRC in rice suspension cells (Lu, et al., 2002, Plant Cell 14: 1963-1980). To determine whether MYBS3 is localized in nucleus, the Ubi promoter was fused to the MYBS3-GFP fusion DNA. The Ubi::MYBS3-GFP and Ubi::GFP constructs were introduced into the rice genome. Protoplasts were isolated from transformed calli, incubated at 4° C. or 28° C., and examined.

Accumulation of MYBS3-GFP was detected mainly in the nucleus, whereas GFP alone was distributed throughout the cell except the vacuole, at both 4° C. and 28° C., suggesting that MYBS3 is constitutively localized in the nucleus.

MYBS3 is Sufficient and Necessary for Cold Tolerance in Rice

Since MYBS3 was induced by cold, its role in cold tolerance in rice was explored by gain- and loss-of-function approaches. Constructs Ubi::MYBS3 and Ubi::MYBS3 (RNAi) (RNA interference) (FIG. 1) were introduced into the rice genome, and several transgenic lines were obtained. Compared to the untransformed wild type (WT) rice, the accumulation of MYBS3 mRNA was 62.5 and 19.4 times that of WT in MYBS3-overexpression [MYBS3(Ox)] lines S3(Ox)-110-1 and S3(Ox)-112-7, and 0.19 and 0.16 times that of WT in MYBS3-underexpression [MYBS3(Ri)] lines S3(Ri)-42-10 and S3(Ri)-52-7. Each of these lines contained only one copy of inserted DNA.

Figure 3:
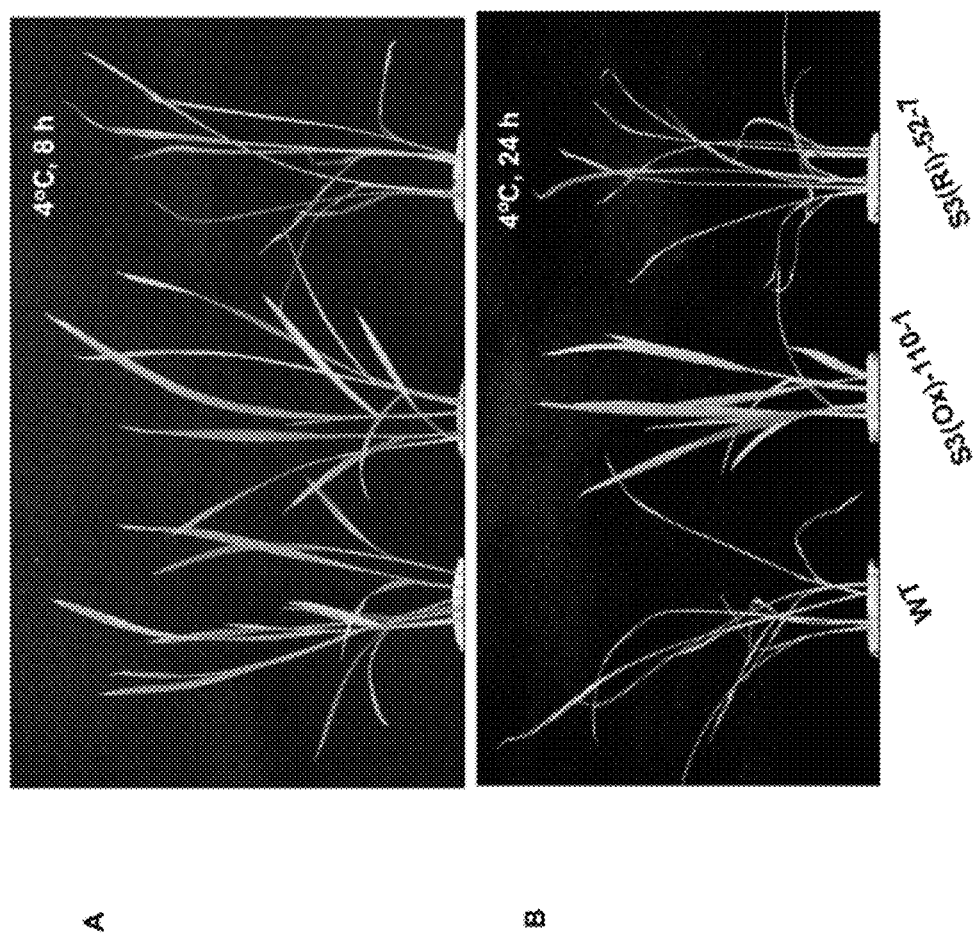
FIG. 3 includes two photographs showing 10-day-old seedlings of wild type (WT) and lines S3(Ox)-110-1 and S3(Ri)-52-7 that were incubated at 4° C. for 8 h (A) or 24 h (B).

To test the cold tolerance of transgenic rice, seedlings were shifted from 28° C. to 4° C. MYBS3(Ox) lines and WT remained normal while MYBS3(Ri) lines started to show leaf rolling at 4° C. after 8 h (FIG. 3A), and both WT and MYBS3 (Ri) lines showed leaf rolling and wilting at 4° C. after 24 h in hydroponic culture (FIG. 3B) or 1 week in soil. Seedlings seemed to be more sensitive to cold in hydroponic culture, probably due to weaker growth in hydroponic culture than in soil. Line S3(Ox)-110-1, which accumulated three times more MYBS3 mRNA than S3(Ox)-112-7, conferred higher cold tolerance than line S3(Ox)-112-7. Quantitative analysis also indicated that MYBS3(Ox) lines were more cold tolerant than WT and MYBS3(Ri) lines, and WTs were more cold tolerant than MYBS3(Ri) lines (Table 2). These observations suggest that MYBS3 is sufficient and necessary for cold tolerance in rice, and the degree of cold tolerance correlates with the MYBS3 expression level.

TABLE 2

MYBS3(Ox) lines are more cold tolerant.

| Line | No. of plants survived* | Total no. of plants tested | Survival rate (%) |
|---|---|---|---|
| Wild type | 3 | 30 | 10.0 ± 0.0 |
| S3(Ox)-110-1 | 18 | 21 | 85.7 ± 10.5 |
| S3(Ox)-112-7 | 26 | 32 | 81.3 ± 11.1 |
| S3(Ri)-42-10 | 0 | 20 | 0.0 ± 0.0 |
| S3(Ri)-52-7 | 0 | 21 | 0.0 ± 0.0 |

*Number of plants survived after exposure to 4° C. for 24 h. Experiments were repeated 4 times. Five to eight plants per line were tested in each experiment. The survival rate is a mean ± SD.

The morphology of transgenic rice was similar to the WT, except under greenhouse growth conditions, where plants of the MYBS3(Ox) lines were 20% shorter, had 30% lower tiller numbers, and headed 1 week later than the WT and MYBS3 (Ri) line. However, in field conditions, most agronomic traits and yield of MYBS3(Ox) lines were similar to those of the WT (Table 3).

TABLE 3

Comparison of agronomic traits of a MYBS3(Ox) line with wild type grown in field.

| Trait | WT | S3(Ox)-110-1 |
|---|---|---|
| Plant height (cm) | 101.6 ± 3.7* | 95.5 ± 5.4 |
| Tiller number | 12.3 ± 2.5 | 19.5 ± 6.8 |
| Panicle number/plant | 12.9 ± 2.9 | 19.0 ± 6.1 |
| Panicle length (cm) | 18.9 ± 1.3 | 18.4 ± 0.1 |

TABLE 3-continued

Comparison of agronomic traits of a MYBS3(Ox) line with wild type grown in field.

| Trait | WT | S3(Ox)-110-1 |
|---|---|---|
| Grain number/panicle | 118.0 ± 14.5 | 103.5 ± 8.8 |
| Fertility (%) | 95.7 ± 1.2 | 93.8 ± 1.7 |
| Grain yield (g/plant) | 41.7 ± 11.0 | 45.4 ± 15.9 |
| 1000 Grains weight (g) | 26.3 ± 0.5 | 24.3 ± 0.4 |

Twenty plants each of WT and line S3(Ox)-110-1 per replicate, and with total of 3 replicates, were grown during February to July, 2008. The value is a mean±SD.

MYBS3 Regulates the Expression of Genes with Diverse Functions

To identify downstream genes regulated by MYBS3 under cold stress, seedlings of S3(Ox)-110-1, S3(Ri)-52-7 and WT were grown at 4 and 28° C. for 24 h. Total RNAs were isolated for microarray analysis using the Affymetrix rice gene chip array containing 55,515 probe sets. Relative change was calculated by comparing the data for MYBS3(Ox) line or MYBS3(Ri) line against those for WT grown at 4° C. and 28° C., generating six comparisons. Only relative changes of 3-fold or more were taken to be significantly different. Based on a Venn diagram analysis, 89 genes were up-regulated in the MYBS3(Ox) line (compared with WT) at either 4 or 28° C., and 1466 genes were up-regulated in WT at 4° C. (compared with 28° C.). Among these genes, 17 genes were up-regulated by over-expression of MYBS3 as well as up-regulated by cold in WT (Table S1 of Su, et al, Plant Physiol. 2010; 153(1):145-58). On the other hand, 291 genes were down-regulated in the MYBS3(Ox) line (compared with WT) at either 4 or 28° C., and 871 genes were down-regulated in WT at 4° C. (compared with 28° C.). Among these genes, 53 genes were down-regulated by over-expression of MYBS3 as well as down-regulated by cold in WT (Table S1 of Su, et al, Plant Physiol. 2010; 153(1):145-58).

Another analysis revealed that 389 genes were up-regulated in the MYBS3(Ri) line (compared with WT) at either 4 or 28° C. Among these genes, 17 genes were up-regulated by under-expression of MYBS3 as well as up-regulated by cold in WT (Table S2 of Su, et al, Plant Physiol. 2010; 153(1):145-58). On the other hand, 124 genes were down-regulated in the MYBS3(Ri) line (compared with WT) at either 4 or 28° C. Among these genes, 37 genes were down-regulated by over-expression of MYBS3 as well as by cold in WT (Table S2 of Su, et al, Plant Physiol. 2010; 153(1):145-58).

The cold- and MYBS3-regulated genes seem to be involved in diverse functions, and many of them have also been shown to be regulated by drought and salt stresses (Tables S1 and S2 of Su, et al, Plant Physiol. 2010; 153(1): 145-58). Among the 17 genes up-regulated by over-expression of MYBS3 as well as up-regulated by cold in WT, five genes that have also been shown to be up-regulated by drought (Table Si of Su, et al, Plant Physiol. 2010; 153(1): 145-58) and cold (Jain, et al., 2007, Plant Physiol 143: 1467-1483), such as genes encoding glutamate decarboxylase, WRKY77, multidrug resistance protein 4, and trehalose-6-phosphate phosphatases (TPP1 and TPP2), were selected for further quantitative real-time RT-PCR analysis. The accumulation of mRNA of all five genes was significantly increased in WT and further increased in the MYBS3(Ox) line but reduced in the MYBS3(Ri) line at 4° C. (Table S3 of Su, et al, Plant Physiol. 2010; 153(1):145-58), indicating that these genes are downstream of the MYBS3-mediated cold signaling pathway.

MYBS3 Suppresses the DREB1-Dependent Pathway Under Prolonged Cold Stress

We noticed that in the microarray analysis, the DREB1 family, including DREB1A, DREB1B and DREB1C, and another two DREB1-like genes (ERF#025 and ERF#104) were up-regulated in WT at 4° C., but the induction was surprisingly reduced or abolished in the MYBS3(Ox) line at 4° C. To investigate how MYBS3 regulates DREB1 gene expression, the accumulation of mRNAs of three DREB1 genes was further analyzed with the quantitative real-time RT-PCR analysis. Compared with WT, accumulation of MYBS3 mRNA increased significantly at 28° C. and was further induced 2-fold at 4° C. in the MYBS3(Ox) line. The accumulation of MYBS3 mRNA was reduced in the MYBS3 (Ri) line at both 4 and 28° C. In contrast, the cold-induced DREB1A, DREB1B and DREB1C expression was significantly suppressed in the MYBS3(Ox) line at 4° C. Furthermore, the cold inducibility of αAmy3/RAmy3D and a cytochrome P450 gene, both members of the cold-inducible DREB1A regulon (Ito, et al., 2006, Plant Cell Physiol 47: 141-153), were also significantly reduced in the MYBS3(Ox) line at 4° C. The accumulation of DREB1, αAmy3/RAmy3D and cytochrome P450 mRNAs were significantly higher in the MYBS3(Ri) line than in the MYBS3(Ox) line at 4° C., although levels did not reach to that in WT at 4° C.

MYBS3 has been shown to repress αAmy3 SRC through the TA box (Lu, et al., 2002, Plant Cell 14: 1963-1980). Examination of promoter regions within 1 kb upstream of the translation start codon (ATG) revealed the presence of TA box and/or its variants in DREB1 genes. To determine whether MYBS3 represses DREB1 promoters, a rice embryo transient expression assay was performed. Rice embryos were cotransfected with the effector construct containing Ubi promoter fused to MYBS3 cDNA and the reporter construct containing DREB1A (1054 bp), DREB1B (747 bp) or αAmy3 SRC (105 bp) promoter sequence fused to luciferase cDNA (Luc). Both DREB1 promoters were significantly induced at 4° C., but only the DREB1B promoter was repressed by over-expression of MYBS3 at 4° C. The αAmy3 SRC was repressed by over-expression of MYBS3 at both 4 and 28° C., consistent with the role of MYBS3 as a repressor of αAmy3 SRC (Lu, et al., 2002, Plant Cell 14: 1963-1980). These results indicate that MYBS3 could repress DREB1B promoter and αAmy3 SRC at 4° C.

Discussion

A Novel MYBS3-Mediated Cold Signaling Pathway

Figure 4:
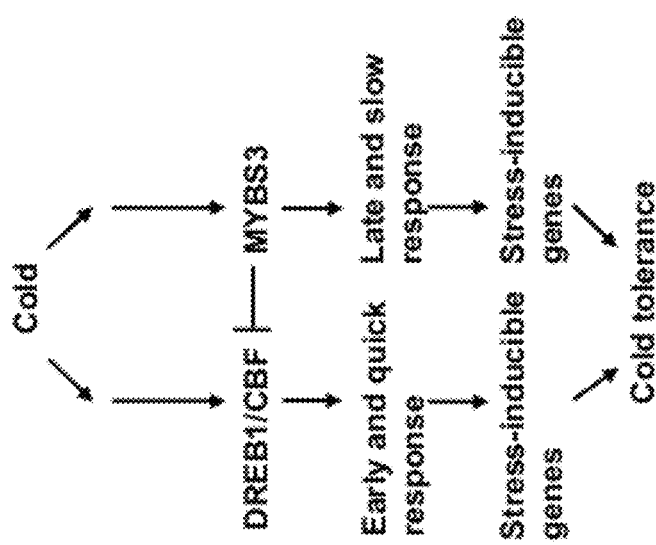
FIG. 4 is a schematic flow chart for a proposed role of MYBS3 in cold stress tolerance in rice.

Both gain- and loss-of-function analyses demonstrated that the MYBS3-mediated pathway was essential for cold stress tolerance in rice. DREB1A responded early and transiently, which is consistent with previous reports in *Arabidopsis* and rice (Liu, et al., 1998, Plant Cell 10: 1391-1406; Shinwari, et al., 1998, Biochem Biophys Res Commun 250: 161-170; Dubouzet, et al., 2003, Plant J 33: 751-763; and Vogel, et al., 2005, Plant J 41: 195-211), whereas MYBS3 responded relatively slowly, to cold stress in rice (FIG. 4). The DREB1-mediated process is most likely crucial in responding to short term cold stress (cold shock), and the MYBS3-mediated system is more important for long-term adaptation to persistent cold stress.

Transcriptome profiling analyses suggest that multiple cold response pathways exist in *Arabidopsis* and rice (Fowler, et al., 2002, Plant Cell 14: 1675-1690; Vogel, et al., 2005, Plant J 41: 195-211; Cheng, et al., 2007, BMC Genomics 8: 175; and Chinnusamy, et al., 2007, Trends Plant Sci 12: 444-451). However, the MYBS3-mediated cold signaling pathway has never been observed previously. MYBS3 acts as a transcriptional repressor of αAmy3 SRC in the sugar signaling pathway in rice (Lu, et al., 2002, Plant Cell 14: 1963-1980), and is constitutively localized in the nucleus in cultured rice suspension cells. These studies indicate that MYBS3 may play multiple regulatory roles in plant growth in addition to cold response in rice. Consequently, gene expression in MYBS3(Ox) or MYBS3(Ri) line altered at 28° C. may not, whereas that altered at 4° C. may, be involved in cold response.

The MYBS3-regulated genes encompass a wide range of functions. In the microarray analysis, among the 17 genes up-regulated for at least 3-fold by over-expression of MYBS3 as well as by cold in WT, several of them have previously been implicated in stress responses and/or tolerance in plants (Table S1 of Su, et al, Plant Physiol. 2010; 153(1):145-58), such as glutamate decarboxylase, which catalyzes the conversion of glutamate to γ-aminobutyrate (GABA) and is activated in response to heat in *Arabidopsis* roots (Bouche et al., 2004, Plant Mol Biol 55: 315-325) and to anoxia in rice roots (Aurisano, et al., 1995, Plant Cell Physiol. 36: 1525-1529); WRKY77, which activates the ABA-inducible HVA22 promoter in cereal grains (Xie, et al., 2005, Plant Physiol 137: 176-189) and several WRKYs have been shown to confer biotic and abiotic stress tolerance in *Arabidopsis* (Ross, et al., 2007, J Integr Plant Biol 49: 827-842; Lai et al., 2008, BMC Plant Biol 8: 68; and Zhou et al., 2008, Plant Biotechnol J 6: 486-503); multidrug resistance protein 4, whose expression is activated by arsenate and arsenite stresses in rice seedlings (Chakrabarty, et al., 2009, Chemosphere 74: 688-702) and its homologous genes confer salt tolerance (Lee, et al., 2004, Plant Physiol 134: 528-538) and oxidative stress tolerance against pathogens (Sun, et al., 2006, Plant Cell 18: 3686-3705) in various plant species.

TPPs are a group of genes worthwhile noting. Trehalose is a disaccharide sugar widely distributed in bacteria, fungi, plants and invertebrate animals, and is produced from glucose by trehalose-6-phosphate synthase (TPS) and TPP, and serves as sugar storage, metabolic regulator, and protectant again abiotic stresses (Strom, et al., 1993, Mol Microbiol 8: 205-210; and Elbein, et al., 2003, Glycobiology 13: 17R-27R). Trehalose has been shown to stabilize dehydrated enzymes, proteins, and lipid membranes, as well as to protect biological structures from damage during desiccation (Elbein, et al., 2003, Glycobiology 13: 17R-27R). TPP1 and TPP2 are two major TPP genes expressed in rice seedlings (Shima, et al., 2007, Febs J 274: 1192-1201). Their expression is induced by cold and other abiotic stresses (Pramanik, et al., 2005, Plant Mol Biol 58: 751-762; Shima, et al., 2007, Febs J 274: 1192-1201; Ge, et al., 2008, Planta 228: 191-201). Trehalose accumulates rapidly and transiently, which follows the transient induction of TPP activity, in rice tissues during chilling stress (Pramanik, et al., 2005, Plant Mol Biol 58: 751-762). Over-expression of TPS and TPP enhances accumulation of trehalose and tolerance to cold stress in transgenic tobacco and rice (Garg, et al., 2002, Proc Natl Acad Sci USA 99: 15898-15903; Jang, et al., 2003 Plant Physiol 131: 516-524; Ge, et al., 2008, Planta 228: 191-201; and Iordachescu, et al., 2008, J Integr Plant Biol 50: 1223-1229). However, the regulatory mechanism of TPPs by cold or other stresses is unclear.

The accumulation of these MYBS3-activated genes were significantly increased in the MYBS3(Ox) line and decreased in the MYBS3(Ri) line at 4° C. MYBS3 confers stress tolerance to transgenic rice through the activation of these genes whose products are involved either in the regulation of gene expression for cold adaptation or for protection of cells from chilling injury.

Complexity in Cold Regulation

The temporal expression patterns and magnitudes of activation of DREB1A and MYBS3 expression by cold are quite different (FIG. 2). Several factors have been found to regulate the expression of DREB1/CBF as mentioned in the introduction, but the detailed information about the cold signaling pathways upstream of DREB1/CBF is rather limited. Recently, a calmodulin binding transcription factor (CAMTA) was found to bind to the conserved motif 2 (CM2) present in promoters (within 200 by upstream of ATG), and function as a positive regulator, of the rapidly cold-inducible CBF2 and ZAT12 transcription factors in *Arabidopsis* (Doherty, et al., 2009, Plant Cell 21: 972-984). CM2 is present in one copy in the MYBS3 promoter (−117 to −112 upstream of ATG) (Table S4 of Su, et al, Plant Physiol. 2010; 153(1):145-58). For cold up-regulated but MYBS3 down-regulated genes, CM2 is present in two copies each in DREB1B (−134 to −129 and −80 to −75) and αAmy3 (−158 to −153 and −149 to −144) promoters; for cold up-regulated and MYBS3 up-regulated genes, CM2 is present in the glutamate decarboxylase (−54 to −49) and WRKY77 promoters (−96 to −91) (Table S4 of Su, et al, Plant Physiol. 2010; 153(1):145-58). Some of other CMs shared by the *Arabidopsis* CBF2 and ZAT12 promoters (Doherty, et al., 2009, Plant Cell 21: 972-984) could also be found in DREB1B, DREB1C, αAmy3 and cytochrome P450 promoters (Table S4 of Su, et al, Plant Physiol. 2010; 153(1):145-58), but the function of these cis-acting elements and the identify of their interacting transcription factors in cold signaling have not been determined (Doherty, et al., 2009, Plant Cell 21: 972-984).

CMs 1-7 have been found in the *Arabidopsis* CBF2 promoter (within 200 by upstream of ATG) (Doherty, et al., 2009, Plant Cell 21: 972-984), however, only CM4 is present in the 1-kb promoter region of DREB1C (the rice CBF2 homolog), suggesting that the mechanism of cold regulation on the DREB1/CBF family might have diverged throughout evolution. No CM is present in the 1-kb promoter region of DREB1A, indicating unidentified cis-acting element(s) could be responsible for cold induction of DREB1A. It appears that combinations of various cis-acting elements and interacting transcription factors constitute the quantitative and temporal regulation of the DREB1- and MYBS3-dependent cold signaling cascades.

It is also noticed that the DREB1A target sequence DRE (Ito, et al., 2006, Plant Cell Physiol 47: 141-153), is present in αAmy3 (−153 to −148) and cytochrome P450 (−605 to −600) promoters, and interestingly, it overlaps with the two CM2s in αAmy3 promoter. None of the 1-kb promoter regions of MYBS3-activated genes further characterized in this study contains DRE.

How MYBS3 represses the expression of the DREB1 regulon is unclear. The TA box has been shown to function in both sense and antisense orientations (Lu, et al., 1998, J Biol Chem 273: 10120-10131). Promoters of the cold inducible but MYBS3 repressible genes, except cytochrome P450, contain TA box or its variants (Yu, 1999, Regulation of alpha-amylase gene expression. In K Shimamoto, ed, Molecular Biology of Rice, Springer-Verlag, Tokyo, pp 161-178; and Wang, et al., 2007, Plant Mol Biol 63: 441-463) in sense or antisense orientation (Table S5 of Su, et al, Plant Physiol. 2010; 153 (1):145-58), which could be the target of repression by MYBS3. However, in the transient expression assay, the 747-bp DREB1B promoter and 105-bp αAmy3 SRC, but not the 1054-bp DREB1A promoter, were repressed by over-expression of MYBS3 at 4° C. One explanation is that the TA3 box (−625 to −620) in the 1054-bp DREB1A promoter did not function as well as the TA2 box (−85 to −80) in the 747-bp DREB1B promoter and the TA1 box (the canonical TA box) (2 copies between −116 to −105) in the 105-bp αAmy3 SRC in the rice embryo transient expression assay.

How MYBS3 activates the expression of downstream genes in the cold signaling pathway, by serving as a transcriptional activator or repressing a transcriptional repressor, is unclear. However, except TPP2, other MYBS3 up-regulated genes also contain TA box or its variants (Table S5 of Su, et al, Plant Physiol. 2010; 153(1):145-58). Both MYBS1 and MYBS3 bind specifically to the TA box, however, MYBS1 activates and MYBS3 represses αAmy3 SRC under sugar starvation (Lu, et al., 2002, Plant Cell 14: 1963-1980). MYBs with one single DNA binding domain (1R MYB) have been proposed to bind DNA as a dimer, and MYBS1 does whereas MYBS3 doesn't form a homodimer (Lu, et al., 2002, Plant Cell 14: 1963-1980). Whether MYBS3 could be converted into an activator, by interacting with other 1R MYB and forming a heterodimer or with other transcription factor(s), remains for further study.

Taken together, above studies suggest the complexity of cold regulation in plants, which involves multiple cis-acting elements and transcription factors. Additionally, the regulation of the MYBS3-dependent pathway differs from that of the DREB1- or ROS-mediated pathways in response to cold stress (Ito, et al., 2006, Plant Cell Physiol 47: 141-153; Cheng, et al., 2007, BMC Genomics 8: 175), which suggests that MYBS3 defines a new signaling pathway mediating cold adaptation in rice. It appears that distinct regulatory pathways function in fine tuning the qualitative and quantitative gene expressions for short- and long-term cold adaptation in rice (FIG. 4).

MYBS3 as a Tool for Improving Cold Stress Tolerance in Crops

Compared with microbial TPP, the rice TPP has been shown to be rather unstable, which leads to low level accumulation of trehalose in rice under normal growth conditions (Shima, et al., 2007, Febs J 274: 1192-1201). Although in WT plant, the expression of two rice TPPs is induced by cold, it peaks around 24 h and declined afterward at 4-6° C. (Pramanik, et al., 2005, Plant Mol Biol 58: 751-762; and Ge, et al., 2008, Planta 228: 191-201). The significant activation of TPP expression in the MYBS3(Ox) line may increase the accumulation of trehalose to levels high enough to confer cold tolerance in rice.

In the MYBS3(Ri) line, the expression of three DREB1 genes were 50-94% of the WT at 4° C., probably due to weaker growth and reduced cellular activities of plants under cold stress, as mentioned above that MYBS3 may play multiple regulatory roles in plant growth in addition to cold response in rice. However, it suggests that high-level DREB1 expression is insufficient to sustain cold tolerance if the level of MYBS3 expression is too low to efficiently activate the TPP-mediated cold response pathway. Consequently, the sequential expression of DREB1 and MYBS3 provides rice two complementary mechanisms for conferring cold tolerance in rice, with the DREB1-mediated process mediates the immediate cold shock response and the MYBS3-mediated system adjusts the long-term cold adaptation in rice. The antithetical regulation of αAmy3 in rice seedlings by two different pathways is physiologically meaningful: the transient activation of αAmy3 expression by DREB1 allows hydrolysis of reserved starch for providing immediate need of carbon source and energy to combat the cold shock, while the subsequent suppression of αAmy3 expression by MYBS3 allows rice to conserve carbohydrates until re-growth is allowed at elevated temperatures. It would be interesting to test whether stacking of these two systems, by over-expression of both DREB1 and MYBS3, could further enhance the cold tolerance in rice.

Overexpression of proteins or enzymes associated with stress responses has been a common practice in improving stress tolerance of crop plants. However, constitutive overexpression of these proteins frequently leads to impaired plant growth or yield penalty. For example, though transgenic *Arabidopsis* and rice constitutively overexpressing CBF/DREB1 and a NAC6 transcription factor are highly tolerant to freezing, the growth rates of these transgenic plants, however, are severely retarded under normal growth conditions (Jaglo-Ottosen, et al., 1998, Science 280: 104-106; Liu, et al., 1998, Plant Cell 10: 1391-1406; Kasuga, et al., 1999, Nat Biotechnol 17: 287-291; Gilmour, et al., 2000, Plant Physiol 124: 1854-1865; Ito, et al., 2006, Plant Cell Physiol 47: 141-153; and Nakashima et al., 2007, Plant J 51: 617-630). Using stress-inducible promoters for the expression of these transcription factors minimize their negative effects on plant growth (Kasuga, et al., 1999, Nat Biotechnol 17: 287-291; and Nakashima, et al., 2007, Plant J 51: 617-630). Transgenic seedlings were able to withstand 4° C. for at least 1 week after shifting from 28° C., which could significantly protect seedlings from chilling injury in rice fields in areas where are easily prone to transient temperature drops in early spring. Although the growth of MYBS3(Ox) lines was affected to certain extent in the greenhouse, the growth and yield of line S3(Ox)-110-1 was normal in field (Table 3). In conclusion, MYBS3 can be used for the improvement of cold tolerance in rice and possibly other crop plants.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A transgenic plant comprising:

a first transgene that contains a first nucleic acid sequence operably linked to a promoter, the first nucleic acid sequence encoding a MYBS3 protein having the sequence of SEQ ID NO:1, and a second transgene that contains a second nucleic acid sequence operably linked to a promoter, the second nucleic acid sequence encoding a DREB1A protein having the sequence of SEQ ID NO:4, wherein the transgenic plant expresses both a higher level of the MYBS3 protein and a higher level of the DREB1A protein as compared to a host plant of the transgenic plant that lacks the first transgene and the second transgene, the transgenic plant being more tolerant to chill as compared to the host plant.

2. The transgenic plant of claim 1, wherein the plant is rice, maize, wheat, barley, sorghum, sugarcane, turf grass, Miscanthus, switchgrass, napier grass, soybean, canola, potato, tomato, bean, pea, or jatropha.

3. The transgenic plant of claim 2, wherein the plant is rice.

4. A method of generating the transgenic plant of claim 1, comprising introducing into a cell of a host plant the first transgene and the second transgene; and identifying and selecting a transgenic plant that is more tolerant to chill as compared to the host plant.

5. The method of claim 4, wherein the host plant is rice, maize, wheat, barley, sorghum, sugarcane, turf grass, Miscanthus, switchgrass, napier grass, soybean, canola, potato, tomato, bean, pea, or jatropha.

6. The method of claim 5, wherein the host plant is rice.

* * * * *

SEQUENCE LISTING

```
<160> NUMBER OF SEQ ID NOS: 66

<210> SEQ ID NO 1
<211> LENGTH: 318
<212> TYPE: PRT
<213> ORGANISM: Oryza sativa

<400> SEQUENCE: 1

Met Thr Arg Arg Cys Ser His Cys Ser His Asn Gly His Asn Ser Arg
1               5                   10                  15

Thr Cys Pro Asn Arg Gly Val Lys Ile Phe Gly Val Arg Leu Thr Asp
                20                  25                  30

Gly Ser Ile Arg Lys Ser Ala Ser Met Gly Asn Leu Ser Leu Leu Ser
            35                  40                  45

Ser Ala Ala Gly Ser Thr Ser Gly Gly Ala Ser Pro Ala Asp Gly Pro
    50                  55                  60

Asp Ala Ala Pro Thr Ala Ala Asp Gly Tyr Ala Ser Asp Asp Phe Val
65                  70                  75                  80

Gln Gly Phe Ser Ser Ala Thr Arg Asp Arg Lys Lys Gly Val Pro Trp
                85                  90                  95

Thr Glu Glu Glu His Arg Arg Phe Leu Leu Gly Leu Gln Lys Leu Gly
                100                 105                 110

Lys Gly Asp Trp Arg Gly Ile Ser Arg Asn Phe Val Val Ser Arg Thr
            115                 120                 125

Pro Thr Gln Val Ala Ser His Ala Gln Lys Tyr Phe Ile Arg Gln Ser
    130                 135                 140

Asn Met Thr Arg Arg Lys Arg Arg Ser Ser Leu Phe Asp Met Val Pro
145                 150                 155                 160

Asp Glu Ser Met Asp Leu Pro Pro Leu Pro Gly Gly Gln Glu Pro Glu
                165                 170                 175

Thr Gln Val Leu Asn Gln Pro Ala Leu Pro Pro Pro Lys Glu Glu Glu
            180                 185                 190

Glu Val Asp Ser Met Glu Ser Asp Thr Ser Ala Val Ala Glu Ser Ser
    195                 200                 205

Ser Ala Ser Ala Ile Met Pro Asp Asn Leu Gln Ser Thr Tyr Pro Val
    210                 215                 220
```

```
Ile Val Pro Ala Tyr Phe Ser Pro Phe Leu Gln Phe Ser Val Pro Phe
225                 230                 235                 240

Trp Gln Asn Gln Lys Asp Glu Asp Gly Pro Val Gln Glu Thr His Glu
            245                 250                 255

Ile Val Lys Pro Val Pro Val His Ser Lys Ser Pro Ile Asn Val Asp
        260                 265                 270

Glu Leu Val Gly Met Ser Lys Leu Ser Ile Gly Glu Ser Asn Gln Glu
    275                 280                 285

Thr Glu Ser Thr Ser Leu Ser Leu Asn Leu Val Gly Gly Gln Asn Arg
290                 295                 300

Gln Ser Ala Phe His Ala Asn Pro Pro Thr Arg Ala Gln Ala
305                 310                 315

<210> SEQ ID NO 2
<211> LENGTH: 1287
<212> TYPE: DNA
<213> ORGANISM: Oryza sativa

<400> SEQUENCE: 2
atcgatcgat cgatctccat aggtggggga agggaagctt tggaaggtgg agggacggag      60
ggggggatga cgaggcggtg ctcgcactgc agccacaacg ggcacaactc gcggacgtgc     120
cccaaccgcg gggtcaagat cttcggggtg cgcctcaccg atggctccat ccgcaagagc     180
gccagcatgg ggaacctctc cctcctctcc tccgccgccg atccaccag cggcggcgcc      240 tcccccgccg acggcccga cgccgccccc accgccgccg acggctacgc ctccgacgac      300
ttcgtccagg gcttctcctc cgccacccgc gaccgcaaga agggtgttcc ttggactgaa     360
gaagaacacc ggaggttttt gcttggattg caaaagcttg caaaggtga ttggcgagga      420 atctctcgta atttcgtggt ctcaagaaca cctactcaag tagccagtca tgctcagaaa     480
tattttatac gccaatccaa tatgaccaga aggaaaagaa ggtctagcct ttttgacatg     540
gtgccagatg agtctatgga ccttccacca cttcctggag gtcaagaacc agagacccaa     600
gtattaaatc aaccagcact acctccaccg aaggaggaag aggaggtaga ttctatggag     660
tcagatactt ctgccgttgc agagagctct tccgcttctg ctatcatgcc agataatttg     720
cagtcgacct atccagtgat tgttccagct tatttctcgc cctttttgca attctcggtt     780
cctttctggc aaaatcagaa agatgaagat ggtcctgtgc aagaaacaca tgagattgtc     840
aagcctgttc cagttcattc aaagagccca atcaacgttg atgagcttgt tggcatgtcg     900
aagctcagca taggagagtc caatcaagag acagagtcta cttctctttc attaaatctg     960
gtaggaggtc aaaatagaca atcagctttc catgcaaatc caccaacaag ggcacaggca    1020
tgatctggtt gtgcacacaa ctgcatttag atgaatccaa ggcaaaataa gctttgcctc    1080
cttgtttttt tgtttttatt ttaagattaa ccgttctccg tagtctgtat catgtgctgt    1140
aagttatgct atgtatgaat gtatctgttg tttgtctggc acacatgata aatcactcta    1200
tgttaacaaa atcagtaatg gtagtgctga tcttcgtggt tgtactgttg taaactcttt    1260
tataagaaaa aaaatatta gttagtc                                         1287

<210> SEQ ID NO 3
<211> LENGTH: 717
<212> TYPE: DNA
<213> ORGANISM: Oryza sativa

<400> SEQUENCE: 3
```

```
atgtgcggga tcaagcagga gatgagcggc gagtcgtcgg ggtcgccgtg cagctcggcg    60
tcggcggagc ggcagcacca gacggtgtgg acggcgccgc cgaagaggcc ggcggggcgg   120
accaagttca gggagacgag gcacccggtg ttccgcggcg tgcggcggag gggcaatgcc   180
gggaggtggg tgtgcgaggt gcgggtgccc gggcggcgcg gctgcaggct ctggctcggc   240
acgttcgaca ccgccgaggg cgcggcgcgc gcgcacgacg ccgccatgct cgccatcaac   300
gccggcggcg gcggcggcgg gggagcatgc tgcctcaact cgccgactc cgcgtggctc    360 ctcgccgtgc cgcgctccta ccgcaccctc gccgacgtcc gccacgccgt cgccgaggcc   420
gtcgaggact cttccggcg ccgcctcgcc gacgacgcgc tgtccgccac gtcgtcgtcc    480
tcgacgacgc cgtccacccc acgcaccgac gacgacgagg agtccgccgc caccgacggc   540
gacgagtcct cctccccggc cagcgacctg gcgttcgaac tggacgtcct gagtgacatg   600
ggctgggacc tgtactacgc gagcttggcg caggggatgc tcatggagcc accatcggcg   660
gcgctcggcg acgacggtga cgccatcctc gccgacgtcc cactctggag ctactag      717
```

<210> SEQ ID NO 4
<211> LENGTH: 238
<212> TYPE: PRT
<213> ORGANISM: Oryza sativa

<400> SEQUENCE: 4

```
Met Cys Gly Ile Lys Gln Glu Met Ser Gly Glu Ser Ser Gly Ser Pro
1               5                   10                  15

Cys Ser Ser Ala Ser Ala Glu Arg Gln His Gln Thr Val Trp Thr Ala
                20                  25                  30

Pro Pro Lys Arg Pro Ala Gly Arg Thr Lys Phe Arg Glu Thr Arg His
            35                  40                  45

Pro Val Phe Arg Gly Val Arg Arg Gly Asn Ala Gly Arg Trp Val
        50                  55                  60

Cys Glu Val Arg Val Pro Gly Arg Arg Gly Cys Arg Leu Trp Leu Gly
65                  70                  75                  80

Thr Phe Asp Thr Ala Glu Gly Ala Ala Arg Ala His Asp Ala Ala Met
                85                  90                  95

Leu Ala Ile Asn Ala Gly Gly Gly Gly Gly Gly Ala Cys Cys Leu
                100                 105                 110

Asn Phe Ala Asp Ser Ala Trp Leu Leu Ala Val Pro Arg Ser Tyr Arg
            115                 120                 125

Thr Leu Ala Asp Val Arg His Ala Val Ala Glu Ala Val Glu Asp Phe
130                 135                 140

Phe Arg Arg Arg Leu Ala Asp Asp Ala Leu Ser Ala Thr Ser Ser Ser
145                 150                 155                 160

Ser Thr Thr Pro Ser Thr Pro Arg Thr Asp Asp Glu Glu Ser Ala
                165                 170                 175

Ala Thr Asp Gly Asp Glu Ser Ser Pro Ala Ser Asp Leu Ala Phe
            180                 185                 190

Glu Leu Asp Val Leu Ser Asp Met Gly Trp Asp Leu Tyr Tyr Ala Ser
        195                 200                 205

Leu Ala Gln Gly Met Leu Met Glu Pro Pro Ser Ala Ala Leu Gly Asp
    210                 215                 220

Asp Gly Asp Ala Ile Leu Ala Asp Val Pro Leu Trp Ser Tyr
225                 230                 235
```

<210> SEQ ID NO 5

-continued

```
<211> LENGTH: 657
<212> TYPE: DNA
<213> ORGANISM: Oryza sativa

<400> SEQUENCE: 5
atggaggtgg aggaggcggc gtacaggacg gtgtggtcgg agccgccgaa gaggccggcg      60
ggaaggacca agttcaggga gacgaggcac ccggtgtacc gcggcgtgcg gcggcgcggg     120
gggcggccgg gcgcggcggg gaggtgggtg tgcgaggtgc gggtgcccgg ggcgcgcggc     180
tccaggctgt ggctcggcac gttcgccacc gccgaggcgg cggcgcgcgc gcacgacgcc     240
gccgcgctgg cgctccgcgg cagggccgcc tgcctcaact cgccgactc cgcgtggcgg      300 atgccgcccg tccccgcgtc cgccgcgctc gccggcgcga ggggggtcag ggacgccgtc     360
gccgtggccg tcgaggcgtt ccagcgccag tcggccgcgc gtcgtctcc ggcggagacc      420 ttcgccaacg atggcgacga agaagaagac aacaaggacg tgttgccggt ggcggcggcg     480
gaggtgttcg acgcggggc gttcgagctc gacgacgggt tcaggttcgg cgggatggac     540
gccgggtcgt actacgcgag cttggcgcag ggctgctcg tcgagccgcc ggccgccgga      600
gcgtggtggg aggacggcga gctcgccggc tccgacatgc cgctctggag ctactaa       657

<210> SEQ ID NO 6
<211> LENGTH: 218
<212> TYPE: PRT
<213> ORGANISM: Oryza sativa

<400> SEQUENCE: 6

Met Glu Val Glu Glu Ala Ala Tyr Arg Thr Val Trp Ser Glu Pro Pro
1               5                   10                  15

Lys Arg Pro Ala Gly Arg Thr Lys Phe Arg Glu Thr Arg His Pro Val
            20                  25                  30

Tyr Arg Gly Val Arg Arg Gly Arg Pro Gly Ala Ala Gly Arg
        35                  40                  45

Trp Val Cys Glu Val Arg Val Pro Gly Ala Arg Gly Ser Arg Leu Trp
    50                  55                  60

Leu Gly Thr Phe Ala Thr Ala Glu Ala Ala Arg Ala His Asp Ala
65                  70                  75                  80

Ala Ala Leu Ala Leu Arg Gly Arg Ala Ala Cys Leu Asn Phe Ala Asp
                85                  90                  95

Ser Ala Trp Arg Met Pro Pro Val Pro Ala Ser Ala Ala Leu Ala Gly
            100                 105                 110

Ala Arg Gly Val Arg Asp Ala Val Ala Val Ala Val Glu Ala Phe Gln
        115                 120                 125

Arg Gln Ser Ala Ala Pro Ser Ser Pro Ala Glu Thr Phe Ala Asn Asp
    130                 135                 140

Gly Asp Glu Glu Glu Asp Asn Lys Asp Val Leu Pro Val Ala Ala Ala
145                 150                 155                 160

Glu Val Phe Asp Ala Gly Ala Phe Glu Leu Asp Asp Gly Phe Arg Phe
                165                 170                 175

Gly Gly Met Asp Ala Gly Ser Tyr Tyr Ala Ser Leu Ala Gln Gly Leu
            180                 185                 190

Leu Val Glu Pro Pro Ala Ala Gly Ala Trp Trp Glu Asp Gly Glu Leu
        195                 200                 205

Ala Gly Ser Asp Met Pro Leu Trp Ser Tyr
    210                 215
```

-continued

```
<210> SEQ ID NO 7
<211> LENGTH: 645
<212> TYPE: DNA
<213> ORGANISM: Oryza sativa

<400> SEQUENCE: 7
atggagtact acgagcagga ggagtacgcg acggtgacgt cggcgccgcc gaagcggccg      60
gcggggagga ccaagttcag ggagacgagg cacccggtgt accgcggcgt gcggcggcgg     120
gggcccgcgg ggcggtgggt gtgcgaggtc agggagccca acaagaagtc ccgcatctgg     180
ctcggcacct tcgccaccgc cgaggccgcc gcgcgcgccc acgacgtcgc cgcgctcgcc     240
ctccgcggcc gcggcgcgtg cctcaacttc gccgactcgg cccgcctcct ccgcgtcgac     300
ccggccaccc tcgccacccc cgacgacatc cgccgcgccg ccatcgagct cgccgagtca     360
tgcccgcacg acgccgccgc cgccgccgcc tccagctccg ccgccgccgt cgaggcctcc     420
gccgccgccg cgcccgccat gatgatgcag taccaggacg acatggcggc gacgccgtcc     480
agctacgact acgcgtacta cggcaacatg gacttcgacc agccgtccta ctactacgac     540
gggatgggcg gcggcggcga gtaccagagc tggcagatgg acgcgacga cgatggtggc     600 gccggcggct acggcggcgg cgacgtcaca ctctggagct actga                    645

<210> SEQ ID NO 8
<211> LENGTH: 214
<212> TYPE: PRT
<213> ORGANISM: Oryza sativa

<400> SEQUENCE: 8

Met Glu Tyr Tyr Glu Gln Glu Glu Tyr Ala Thr Val Thr Ser Ala Pro
1               5                   10                  15

Pro Lys Arg Pro Ala Gly Arg Thr Lys Phe Arg Glu Thr Arg His Pro
            20                  25                  30

Val Tyr Arg Gly Val Arg Arg Gly Pro Ala Gly Arg Trp Val Cys
        35                  40                  45

Glu Val Arg Glu Pro Asn Lys Lys Ser Arg Ile Trp Leu Gly Thr Phe
    50                  55                  60

Ala Thr Ala Glu Ala Ala Ala Arg Ala His Asp Val Ala Ala Leu Ala
65                  70                  75                  80

Leu Arg Gly Arg Gly Ala Cys Leu Asn Phe Ala Asp Ser Ala Arg Leu
                85                  90                  95

Leu Arg Val Asp Pro Ala Thr Leu Ala Thr Pro Asp Asp Ile Arg Arg
            100                 105                 110

Ala Ala Ile Glu Leu Ala Glu Ser Cys Pro His Asp Ala Ala Ala Ala
        115                 120                 125

Ala Ala Ser Ser Ala Ala Ala Val Glu Ala Ser Ala Ala Ala Ala
    130                 135                 140

Pro Ala Met Met Met Gln Tyr Gln Asp Asp Met Ala Ala Thr Pro Ser
145                 150                 155                 160

Ser Tyr Asp Tyr Ala Tyr Tyr Gly Asn Met Asp Phe Asp Gln Pro Ser
                165                 170                 175

Tyr Tyr Tyr Asp Gly Met Gly Gly Gly Gly Glu Tyr Gln Ser Trp Gln
            180                 185                 190

Met Asp Gly Asp Asp Asp Gly Gly Ala Gly Gly Tyr Gly Gly Gly Asp
        195                 200                 205

Val Thr Leu Trp Ser Tyr
    210
```

<210> SEQ ID NO 9
<211> LENGTH: 762
<212> TYPE: DNA
<213> ORGANISM: Oryza sativa

<400> SEQUENCE: 9

| | |
|---|---|
| atggagaaga acaccgccgc cagcgggcaa ttgatgacct cctccgcgga ggcgacgccg | 60 |
| tcgtcgccga agcggccggc ggggcgaacc aagttccagg agacgaggca cctagtgttc | 120 |
| cgtggggtgc gatggcgtgg gtgcgcgggg cggtgggtgt gcaaggtgcg tgtcccgggc | 180 |
| agccgcggtg accgtttctg gataggcacg tctgacaccg ccgaggagac cgcgcgcacg | 240 |
| cacgacgccg ccatgctcgc cttgtgcggg gcctccgcca gcctcaactt cgccgactct | 300 |
| gcctggctgc tccacgtccc gcgcgccccc gtcgtctccg gactccggcc accagctgcc | 360 |
| cgatgtgcaa cgcgctgcct gcaaggccat cgccgagttc cagcgccggg ccggggagc | 420 |
| accgccactg ccactgccac ctccggcgat gctgcatcga ccgctcctcc gtcggcaccc | 480 |
| gttctgtcag ccaaacaatg cgaattcatc tttctttctt cactagattg ttggatgtta | 540 |
| atgtcaaagc ttatcagcag tagcagagca aaaggatcgt tgtgcctgcg aaaaaatccc | 600 |
| atttcatttt gcatggttac aaattcttac actgctcttt tgctcgaata cattatattg | 660 |
| cagatgaatt caatgatcgt tttaatccac gaattatcaa aatatcaagt ctttctgcta | 720 |
| ctaaccatga taacacacca cctttttcaa tggaggaggt ag | 762 |

<210> SEQ ID NO 10
<211> LENGTH: 253
<212> TYPE: PRT
<213> ORGANISM: Oryza sativa

<400> SEQUENCE: 10

Met Glu Lys Asn Thr Ala Ala Ser Gly Gln Leu Met Thr Ser Ser Ala
1               5                   10                  15

Glu Ala Thr Pro Ser Ser Pro Lys Arg Pro Ala Gly Arg Thr Lys Phe
            20                  25                  30

Gln Glu Thr Arg His Leu Val Phe Arg Gly Val Arg Trp Arg Gly Cys
        35                  40                  45

Ala Gly Arg Trp Val Cys Lys Val Arg Val Pro Gly Ser Arg Gly Asp
    50                  55                  60

Arg Phe Trp Ile Gly Thr Ser Asp Thr Ala Glu Glu Thr Ala Arg Thr
65                  70                  75                  80

His Asp Ala Ala Met Leu Ala Leu Cys Gly Ala Ser Ala Ser Leu Asn
                85                  90                  95

Phe Ala Asp Ser Ala Trp Leu Leu His Val Pro Arg Ala Pro Val Val
            100                 105                 110

Ser Gly Leu Arg Pro Pro Ala Ala Arg Cys Ala Thr Arg Cys Leu Gln
        115                 120                 125

Gly His Arg Arg Val Pro Ala Pro Gly Arg Gly Ser Thr Ala Thr Ala
    130                 135                 140

Thr Ala Thr Ser Gly Asp Ala Ala Ser Thr Ala Pro Pro Ser Ala Pro
145                 150                 155                 160

Val Leu Ser Ala Lys Gln Cys Glu Phe Ile Phe Leu Ser Ser Leu Asp
                165                 170                 175

Cys Trp Met Leu Met Ser Lys Leu Ile Ser Ser Arg Ala Lys Gly
            180                 185                 190

Ser Leu Cys Leu Arg Lys Asn Pro Ile Ser Phe Cys Met Val Thr Asn

```
            195                 200                 205
Ser Tyr Thr Ala Leu Leu Leu Glu Tyr Ile Ile Leu Gln Met Asn Ser
    210                 215                 220

Met Ile Val Leu Ile His Glu Leu Ser Lys Tyr Gln Val Phe Leu Leu
225                 230                 235                 240

Leu Thr Met Ile Thr His His Leu Phe Gln Trp Arg Arg
                245                 250

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
cctttctggc aaaatcagaa aga                                           23

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
atgaactgga acaggcttga ca                                            22

<210> SEQ ID NO 13
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 13
gcggatcccc ttttgacttg caggttaatt acttcagg                           38

<210> SEQ ID NO 14
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 14
catgccatgg tttaaacccc ccctccgtcc ctccaccttc c                       41

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
ggacctgtac tacgcgagct t                                             21

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide
```

```
<400> SEQUENCE: 16
ggcaaaattg tacagttgat tga                                    23

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttgaccggga taccgaatta                                        20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gtaatggcga tgggagaaga                                        20

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
agctcgccgg ctccgaca                                          18

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
gggagaaatc tggcacattc c                                      21

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
aggtaagcca ttagcgcatg                                        20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ggatgactct ctctggttca                                        20

<210> SEQ ID NO 23
<211> LENGTH: 23
```

```
<212> TYPE: DNA
<213> ORGANISM: Artificial sequence
<220> FEATURE:
<223> OTHER INFORMATION: Synthetic oligonucleotide

<400> SEQUENCE: 23
gagttggagc tagcagtttt gag                                              23

<210> SEQ ID NO 24
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 24
tagctgtata ggaggagcaa agc                                              23

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
gtaggcaggc tctctagcct ctagg                                            25

<210> SEQ ID NO 26
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 26
gtaggcaggc tctctagcct ctagg                                            25

<210> SEQ ID NO 27
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 27
gtcatccagg agacgatgag g                                                21

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28
gatgttgcgg aacagaggta g                                                21

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 29
```
cctatcaact ttcgatggta ggata                                          25

<210> SEQ ID NO 30
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 30
cgttaaggga tttagattgt actcatt                                        27

<210> SEQ ID NO 31
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 31
ggagttcctc aatttcttgg tg                                             22

<210> SEQ ID NO 32
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 32
cgcctcggaa actacagtta tt                                             22

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 33
aggatgcatt caaggttctg a                                              21

<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
caagatgcca gtttcttcag g                                              21

<210> SEQ ID NO 35
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 35
cctgtccttt taccagacaa cc                                             22

<210> SEQ ID NO 36
<211> LENGTH: 22
<212> TYPE: DNA
<213> ORGANISM: Artificial sequence

```
<220> FEATURE:
<223> OTHER INFORMATION: Synthetic oligonucleotide

<400> SEQUENCE: 36
ggaccatgtg gtctctcttt tc                                              22

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
caggcagagg aacaggtgat                                                 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
cgtaccggaa caagctgaac                                                 20

<210> SEQ ID NO 39
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 39
aagacgctgc tgattgatat gat                                             23

<210> SEQ ID NO 40
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 40
tggtagctca caccatgaat gta                                             23

<210> SEQ ID NO 41
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 41
ggaatggaca attagtttgt ctcc                                            24

<210> SEQ ID NO 42
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 42
atatatcgat gggccgtaat ttt                                             23
```

<210> SEQ ID NO 43
<211> LENGTH: 1129
<212> TYPE: DNA
<213> ORGANISM: Arabidopsis thaliana

<400> SEQUENCE: 43

```
atgactcgtc gatgttctca ctgcaatcac aatggccaca actctcggac ttgtcccaat        60
cgcggcgtga agctctttgg tgttcggctc accgaaggtt cgatccggaa aagtgcaagt       120
atgggtaatc ttagccatta cacgggttct ggatcgggtg ggcatggaac cgggtccaac       180
actccgggtt ctccgggtga tgtccctgac catgtcgctg gtgatggtta cgcttctgag       240
gatttcgttg ctggctcttc ctctagccgc gagagaaaga aaggaactcc atggacagag       300
gaagaacaca ggatgttctt attaggttta cagaagctgg gtaaaggtga ttggagaggt       360
atctcaagaa actatgtgac cactaggaca cctacacaag ttgctagcca tgctcagaag       420
tatttcatca gacaatccaa tgtctctcgt cgcaaaagac gttctagtct ctttgatatg       480
gttcctgatg aggttggaga tattcccatg gatttgcaag aaccagagga agataatatt       540
cctgtggaaa ctgaaatgca aggtgctgac tctattcatc agacacttgc tcctagctca       600
cttcacgcac cgtcaatctt ggaaatcgaa gaatgtgaat caatggactc acaaactct       660
accaccgggg aaccaaccgc aactgccgct gctgcttctt cttcttccag actagaagaa       720
accacacaac tgcaatcaca actgcaaccg cagccgcaac tacctggctc attccccata       780
ctatatccga cctactttc accatattac ccgtttccat cccaatatg gcctgctggt       840
tatgttcctg aaccacccaa gaagaggaa actcatgaaa ttctcagacc aactgctgtg       900
cactcgaaag ctcctatcaa tgttgacgag cttcttggta tgtctaagct cagccttgca       960
gagtccaaca acatggaga tccgatcag tctctttcat tgaagctagg tggcgggtca      1020
tcttcaagac aatcagcatt tcacccgaat cctagctctg atagttcaga catcaaaagc      1080
gtgatacacg ctttataaaa gacctgagga agtgatggtc taaaatggg                  1129
```

<210> SEQ ID NO 44
<211> LENGTH: 365
<212> TYPE: PRT
<213> ORGANISM: Arabidopsis thaliana

<400> SEQUENCE: 44

```
Met Thr Arg Arg Cys Ser His Cys Asn His Asn Gly His Asn Ser Arg
 1               5                  10                  15

Thr Cys Pro Asn Arg Gly Val Lys Leu Phe Gly Val Arg Leu Thr Glu
            20                  25                  30

Gly Ser Ile Arg Lys Ser Ala Ser Met Gly Asn Leu Ser His Tyr Thr
        35                  40                  45

Gly Ser Gly Ser Gly Gly His Gly Thr Gly Ser Asn Thr Pro Gly Ser
    50                  55                  60

Pro Gly Asp Val Pro Asp His Val Ala Gly Asp Gly Tyr Ala Ser Glu
65                  70                  75                  80

Asp Phe Val Ala Gly Ser Ser Ser Ser Arg Glu Arg Lys Lys Gly Thr
                85                  90                  95

Pro Trp Thr Glu Glu His Arg Met Phe Leu Leu Gly Leu Gln Lys
            100                 105                 110

Leu Gly Lys Gly Asp Trp Arg Gly Ile Ser Arg Asn Tyr Val Thr Thr
        115                 120                 125

Arg Thr Pro Thr Gln Val Ala Ser His Ala Gln Lys Tyr Phe Ile Arg
```

```
                    130             135                 140
Gln Ser Asn Val Ser Arg Arg Lys Arg Arg Ser Ser Leu Phe Asp Met
145                 150                 155                 160

Val Pro Asp Glu Val Gly Asp Ile Pro Met Asp Leu Gln Glu Pro Glu
                165                 170                 175

Glu Asp Asn Ile Pro Val Glu Thr Glu Met Gln Gly Ala Asp Ser Ile
            180                 185                 190

His Gln Thr Leu Ala Pro Ser Ser Leu His Ala Pro Ser Ile Leu Glu
        195                 200                 205

Ile Glu Glu Cys Glu Ser Met Asp Ser Thr Asn Ser Thr Thr Gly Glu
    210                 215                 220

Pro Thr Ala Thr Ala Ala Ala Ala Ser Ser Ser Arg Leu Glu Glu
225                 230                 235                 240

Thr Thr Gln Leu Gln Ser Gln Leu Gln Pro Gln Pro Gln Leu Pro Gly
                245                 250                 255

Ser Phe Pro Ile Leu Tyr Pro Thr Tyr Phe Ser Pro Tyr Tyr Pro Phe
            260                 265                 270

Pro Phe Pro Ile Trp Pro Ala Gly Tyr Val Pro Glu Pro Pro Lys Lys
        275                 280                 285

Glu Glu Thr His Glu Ile Leu Arg Pro Thr Ala Val His Ser Lys Ala
    290                 295                 300

Pro Ile Asn Val Asp Glu Leu Leu Gly Met Ser Lys Leu Ser Leu Ala
305                 310                 315                 320

Glu Ser Asn Lys His Gly Glu Ser Asp Gln Ser Leu Ser Leu Lys Leu
                325                 330                 335

Gly Gly Gly Ser Ser Arg Gln Ser Ala Phe His Pro Asn Pro Ser
            340                 345                 350

Ser Asp Ser Ser Asp Ile Lys Ser Val Ile His Ala Leu
        355                 360                 365

<210> SEQ ID NO 45
<211> LENGTH: 1164
<212> TYPE: DNA
<213> ORGANISM: Arabidopsis thaliana

<400> SEQUENCE: 45
atgactcgtc ggtgttcgca ttgtagcaac aatgggcaca attcacgcac gtgtccaacg    60
cgtggtggtg gcacgtgcgg tggaagtggc ggaggaggag gaggtggtgg tggaggaggg   120
tctggttcct cctccgccgt gaagttattt ggtgtgaggt taacggatgg ctcgattatt   180
aaaaagagtg cgagtatggg taatctctcg gcattggctg ttgcggcggc ggcggcaacg   240
caccaccgtt tatctccgtc gtctcctctg gcgacgtcaa atcttaatga ttcgccgtta   300
tcggatcatg cccgatactc taatttgcat cataatgaag ggtatttatc tgatgatcct   360
gctcatggtt ctgggtctag tcaccgtcgt ggtgagagga agagaggtgt tccttggact   420
gaagaggaac atagactatt cttagtcggt cttcagaaac tcgggaaagg agattggcgc   480
ggtatttcga gaaactatgt aacgtcaaga actcctacac aagtggctag tcatgctcaa   540
aagtatttta ttcgacatac tagttcaagc cgcaggaaaa gacggtctag cctcttcgac   600
atggttacag atgagatggt aaccgattca tcgccaacac aggaagagca gaccttaaac   660
ggttcctctc caagcaagga acctgaaaag aaaagctacc ttccttcact tgagctctca   720
ctcaataata ccacagaagc tgaagaggtc gtagccacgg cgccacgaca ggaaaaatct   780
caagaagcta tagaaccatc aaatggtgtt tcaccaatgc tagtcccggg tggcttcttt   840
```

```
cctccttgtt ttccagtgac ttacacgatt tggctccctg cgtcacttca cggaacagaa      900
catgccttaa acgctgagac ttcttctcag cagcatcagg tcctaaaacc aaaacctgga      960
tttgctaaag aacgtgtgaa catggacgag ttggtcggta tgtctcagct tagcatagga     1020
atggcgacaa gacacgaaac cgaaacttcc ccttccccgc tatctttgag actagagccc     1080
tcaaggccat cagcgtttca ctcgaatggc tcggttaatg gtgcagattt gagtaaaggc     1140
aacagcgcga ttcaggctat ctaa                                            1164

<210> SEQ ID NO 46
<211> LENGTH: 387
<212> TYPE: PRT
<213> ORGANISM: Arabidopsis thaliana

<400> SEQUENCE: 46

Met Thr Arg Arg Cys Ser His Cys Ser Asn Asn Gly His Asn Ser Arg
1               5                   10                  15

Thr Cys Pro Thr Arg Gly Gly Gly Thr Cys Gly Gly Ser Gly Gly Gly
                20                  25                  30

Gly Gly Gly Gly Gly Gly Gly Gly Ser Gly Ser Ser Ser Ala Val Lys
            35                  40                  45

Leu Phe Gly Val Arg Leu Thr Asp Gly Ser Ile Ile Lys Lys Ser Ala
    50                  55                  60

Ser Met Gly Asn Leu Ser Ala Leu Ala Val Ala Ala Ala Ala Ala Thr
65                  70                  75                  80

His His Arg Leu Ser Pro Ser Pro Leu Ala Thr Ser Asn Leu Asn
                85                  90                  95

Asp Ser Pro Leu Ser Asp His Ala Arg Tyr Ser Asn Leu His His Asn
            100                 105                 110

Glu Gly Tyr Leu Ser Asp Asp Pro Ala His Gly Ser Gly Ser Ser His
        115                 120                 125

Arg Arg Gly Glu Arg Lys Arg Gly Val Pro Trp Thr Glu Glu Glu His
    130                 135                 140

Arg Leu Phe Leu Val Gly Leu Gln Lys Leu Gly Lys Gly Asp Trp Arg
145                 150                 155                 160

Gly Ile Ser Arg Asn Tyr Val Thr Ser Arg Thr Pro Thr Gln Val Ala
                165                 170                 175

Ser His Ala Gln Lys Tyr Phe Ile Arg His Thr Ser Ser Ser Arg Arg
            180                 185                 190

Lys Arg Arg Ser Ser Leu Phe Asp Met Val Thr Asp Glu Met Val Thr
        195                 200                 205

Asp Ser Ser Pro Thr Gln Glu Glu Gln Thr Leu Asn Gly Ser Ser Pro
    210                 215                 220

Ser Lys Glu Pro Glu Lys Lys Ser Tyr Leu Pro Ser Leu Glu Leu Ser
225                 230                 235                 240

Leu Asn Asn Thr Thr Glu Ala Glu Glu Val Val Ala Thr Ala Pro Arg
                245                 250                 255

Gln Glu Lys Ser Gln Glu Ala Ile Glu Pro Ser Asn Gly Val Ser Pro
            260                 265                 270

Met Leu Val Pro Gly Gly Phe Pro Pro Cys Phe Pro Val Thr Tyr
        275                 280                 285

Thr Ile Trp Leu Pro Ala Ser Leu His Gly Thr Glu His Ala Leu Asn
    290                 295                 300

Ala Glu Thr Ser Ser Gln Gln His Gln Val Leu Lys Pro Lys Pro Gly
```

```
                305                 310                 315                 320
        Phe Ala Lys Glu Arg Val Asn Met Asp Glu Leu Val Gly Met Ser Gln
                        325                 330                 335

Leu Ser Ile Gly Met Ala Thr Arg His Glu Thr Glu Thr Ser Pro Ser
                        340                 345                 350

Pro Leu Ser Leu Arg Leu Glu Pro Ser Arg Pro Ser Ala Phe His Ser
                        355                 360                 365

Asn Gly Ser Val Asn Gly Ala Asp Leu Ser Lys Gly Asn Ser Ala Ile
                        370                 375                 380

Gln Ala Ile
        385

<210> SEQ ID NO 47
<211> LENGTH: 948
<212> TYPE: DNA
<213> ORGANISM: Zea May

<400> SEQUENCE: 47
atgacgcggc ggtgctcgca ctgcagccac aacgggcaca actcgcggac gtgccccaac    60
cgcggggtca agatcttcgg ggtgcacctc accgatggct cggccatccg caagagcgcg   120
agcatgggga acctctccct cctctccgcg ggatccacca gcggcggcgc gtcccccgcc   180
gacgggcccg acctcgccga cggcggcggg ggctacgcct ccgacgactt cgtccagggg   240
tcgtcctccg ccagccgcga tcgaaagaaa ggtgttcctt ggactgaaga agaacaccgg   300 aggttttttgc tgggattaca aaagctcggg aaaggggatt ggcgaggaat ttctcgtaat   360
tttgtggtct caagaacacc tactcaagta gcaagtcatg ctcaaaagta tttatacgc    420 caatcaaata tgagcagaag gaagagaagg tctagccttt tcgacatggt tcctgatgag   480
tccatggacc ttccgccct tcctggaagt caagaaccag agacctcaat gttaaatcaa    540
ccgccactgc ctcctgctgt ggaggaggag gtggaatcga tggagtcaga tacttctgct   600
gtcgcagaga gttctggagc ttctgctctc atgcccgaga gtttacagcc tacctatccg   660
atgattgttc cagcttattt ctcgccgttc ttgcaattct cagttccttt ctggccaaat   720
caggaagatg gaggcgatct tccccaagaa acacacgaga ttgtcaagcc tgttgcagtt   780
cattcccaga atccaattaa tgttgatgaa ctcgtgggca tgtcaaagct aagcatatgg   840
gagcatggtc aggagacagt gtctacttct ctgtcgctaa atctgctagg gggtcaaaat   900
aggcagtcgg ctttccatgc aaaccctcaa acaagagctc aagcctga               948

<210> SEQ ID NO 48
<211> LENGTH: 315
<212> TYPE: PRT
<213> ORGANISM: Zea May

<400> SEQUENCE: 48

Met Thr Arg Arg Cys Ser His Cys Ser His Asn Gly His Asn Ser Arg
1               5                   10                  15

Thr Cys Pro Asn Arg Gly Val Lys Ile Phe Gly Val His Leu Thr Asp
                20                  25                  30

Gly Ser Ala Ile Arg Lys Ser Ala Ser Met Gly Asn Leu Ser Leu Leu
            35                  40                  45

Ser Ala Gly Ser Thr Ser Gly Gly Ala Ser Pro Ala Asp Gly Pro Asp
        50                  55                  60

Leu Ala Asp Gly Gly Gly Gly Tyr Ala Ser Asp Asp Phe Val Gln Gly
65                  70                  75                  80
```

```
Ser Ser Ser Ala Ser Arg Asp Arg Lys Lys Gly Val Pro Trp Thr Glu
            85                  90                  95
Glu Glu His Arg Arg Phe Leu Leu Gly Leu Gln Lys Leu Gly Lys Gly
            100                 105                 110
Asp Trp Arg Gly Ile Ser Arg Asn Phe Val Val Ser Thr Pro Thr
            115                 120                 125
Gln Val Ala Ser His Ala Gln Lys Tyr Phe Ile Arg Gln Ser Asn Met
130                 135                 140
Ser Arg Arg Lys Arg Arg Ser Ser Leu Phe Asp Met Val Pro Asp Glu
145                 150                 155                 160
Ser Met Asp Leu Pro Pro Leu Pro Gly Ser Gln Glu Pro Glu Thr Ser
            165                 170                 175
Met Leu Asn Gln Pro Pro Leu Pro Pro Ala Val Glu Glu Val Glu
            180                 185                 190
Ser Met Glu Ser Asp Thr Ser Ala Val Ala Glu Ser Ser Gly Ala Ser
            195                 200                 205
Ala Leu Met Pro Glu Ser Leu Gln Pro Thr Tyr Pro Met Ile Val Pro
            210                 215                 220
Ala Tyr Phe Ser Pro Phe Leu Gln Phe Ser Val Pro Phe Trp Pro Asn
225                 230                 235                 240
Gln Glu Asp Gly Gly Asp Leu Pro Gln Glu Thr His Glu Ile Val Lys
            245                 250                 255
Pro Val Ala Val His Ser Gln Asn Pro Ile Asn Val Asp Glu Leu Val
            260                 265                 270
Gly Met Ser Lys Leu Ser Ile Trp Glu His Gly Gln Gly Thr Val Ser
            275                 280                 285
Thr Ser Leu Ser Leu Asn Leu Leu Gly Gly Gln Asn Arg Gln Ser Ala
            290                 295                 300
Phe His Ala Asn Pro Gln Thr Arg Ala Gln Ala
305                 310                 315

<210> SEQ ID NO 49
<211> LENGTH: 876
<212> TYPE: DNA
<213> ORGANISM: Zea May

<400> SEQUENCE: 49
atggctcggc catccgcaag agcgcaagca tggggaacct ctccctcctc tccgcggggt      60
caaccagcgg cggcgcgtcg cccgccgacg ggcccgacct cgccgacggc ggcgggggct     120
acgcctccga cgacttcgtc cagggggtcgt cctccgccag ccgcgagcgt aagaaaggtg     180
ttccttggac tgaagaagaa caccggaggt ttttgctggg gattacaaa agcttgggg       240
aaaggtgatt ggcgagggga ttttctcgta attttcgtgg tctcaaagaa caccctactc     300
aaagtagcaa agtcatgctc aaaaaatatt tttatacgtc aaatcaaata tgagcagaag     360
ggaagagaag gtctagcctt ttttgacatg gtgcctgatg agtccatgga ccttccaccc     420
cttcctggaa gtcaagagcc agagacctca gtgttaaatc aaccaccact gcctcccct      480
gtggaggagg aggaggaggt ggaatcgatg gagtcagata cttctgctgt tgcggagagt     540
tctgcagctt cagctcttat gcccgagagt ttacagccta cctatccgat gattgttcca     600
gcttatttct caccgttctt gcaattctca gttcctttct ggccaaatca ggaagatgga     660
ggtgatctgc ctcaagaaac gcacgagatt gtcaagcctg ttgcagttca ttccaagaat     720
ccaattaatg ttgatgaact tgtgagcatg tcaaagctaa gcataggga gcctggtcag     780
```

```
gaaacggtgt ctacttctct gtcgttaaat ctgctggtgg gtcaaaatag gcagtcggcc    840
ttccatgcaa atcctcaaac gagggctcaa gcttga                              876
```

<210> SEQ ID NO 50
<211> LENGTH: 291
<212> TYPE: PRT
<213> ORGANISM: Zea May

<400> SEQUENCE: 50

```
Met Ala Arg Pro Ser Ala Arg Ala Gln Ala Trp Gly Thr Ser Pro Ser
1               5                   10                  15

Ser Pro Arg Gly Gln Pro Ala Ala Arg Arg Pro Pro Thr Gly Pro
            20                  25                  30

Thr Ser Pro Thr Ala Ala Gly Ala Thr Pro Pro Thr Thr Ser Ser Arg
        35                  40                  45

Gly Arg Pro Pro Pro Ala Ala Ser Val Arg Lys Val Phe Leu Gly Leu
    50                  55                  60

Lys Lys Asn Thr Gly Gly Phe Leu Leu Gly Ile Thr Lys Ser Leu Gly
65                  70                  75                  80

Lys Gly Asp Trp Arg Gly Asp Phe Leu Val Ile Phe Val Val Ser Lys
                85                  90                  95

Asn Thr Leu Leu Lys Val Ala Lys Ser Cys Ser Lys Asn Ile Phe Ile
            100                 105                 110

Arg Gln Ile Lys Tyr Glu Gln Lys Gly Arg Glu Gly Leu Ala Phe Phe
        115                 120                 125

Asp Met Val Pro Asp Glu Ser Met Asp Leu Pro Leu Pro Gly Ser
    130                 135                 140

Gln Glu Pro Glu Thr Ser Val Leu Asn Gln Pro Pro Leu Pro Pro
145                 150                 155                 160

Val Glu Glu Glu Glu Val Glu Ser Met Glu Ser Asp Thr Ser Ala
                165                 170                 175

Val Ala Glu Ser Ser Ala Ala Ser Ala Leu Met Pro Glu Ser Leu Gln
            180                 185                 190

Pro Thr Tyr Pro Met Ile Val Pro Ala Tyr Phe Ser Pro Phe Leu Gln
        195                 200                 205

Phe Ser Val Pro Phe Trp Pro Asn Gln Glu Asp Gly Gly Asp Leu Pro
    210                 215                 220

Gln Glu Thr His Glu Ile Val Lys Pro Val Ala Val His Ser Lys Asn
225                 230                 235                 240

Pro Ile Asn Val Asp Glu Leu Val Ser Met Ser Lys Leu Ser Ile Gly
                245                 250                 255

Glu Pro Gly Gln Glu Thr Val Ser Thr Ser Leu Ser Leu Asn Leu Leu
            260                 265                 270

Val Gly Gln Asn Arg Gln Ser Ala Phe His Ala Asn Pro Gln Thr Arg
        275                 280                 285

Ala Gln Ala
    290
```

<210> SEQ ID NO 51
<211> LENGTH: 951
<212> TYPE: DNA
<213> ORGANISM: Sorghum bicolor

<400> SEQUENCE: 51

```
atgacgcggc ggtgctcgca ctgcagccac aacgggcaca actcgcggac gtgccccaac    60
```

-continued

```
cgcggggtca agatcttcgg ggtgcgcctc accgatggct ccgccatccg caagagcgcc    120
agcatgggga acctctccct cctctccgcg ggatccacca gcggcggcgc gtccccgcc     180
gacgggcccg acctcgccga cggcggcgcc ggggatacg  cctccgacga cttcgtccag    240
ggctcctcct ccgccagccg cgagcgcaag aaaggtgttc cttggactga agaagaacac    300
cggaggtttt tgctgggatt acaaaagctt gggaaaggtg attggcgagg aatttctcgt    360
aatttcgtgg tctcaagaac acctactcaa gtagcaagtc atgctcaaaa atattttata    420
cgtcaatcaa atatgagcag aaggaagaga aggtctagcc ttttgacat  ggtgcctgat    480
gagtccatgg accttccacc ccttcctgga agtcaagaac cagagacctc agtgttaaat    540
caagcaccac tgccgcctcc tgtggaggag gaggtggaat caatggagtc agatacttct    600
gctgttgcag agagttctac ggcttctgct ctcatgcccg agagtttaca acctaattat    660
ccgatgattg ttccagctta tttctcaccg ttcttgcaat tctcagttcc tttctggcca    720
aatcaggaag atggaggcga tctgccccaa gaaacacacg agattgtcaa gcctgtggca    780
gttcattcca agaatccaat taatgttgat gaacttgtgg gcatgtcaaa gctaagcata    840
ggggagcctg gtcaggagac agtttctact tctctgtcgc taaatctgct aggggtcaa    900
aataggcagt cggcttttcca tgcaaatcct caaacgagag ctcaagcctg a             951

<210> SEQ ID NO 52
<211> LENGTH: 316
<212> TYPE: PRT
<213> ORGANISM: Sorghum bicolor

<400> SEQUENCE: 52

Met Thr Arg Arg Cys Ser His Cys Ser His Asn Gly His Asn Ser Arg
1               5                   10                  15

Thr Cys Pro Asn Arg Gly Val Lys Ile Phe Gly Val Arg Leu Thr Asp
                20                  25                  30

Gly Ser Ala Ile Arg Lys Ser Ala Ser Met Gly Asn Leu Ser Leu Leu
            35                  40                  45

Ser Ala Gly Ser Thr Ser Gly Gly Ala Ser Pro Ala Asp Gly Pro Asp
        50                  55                  60

Leu Ala Asp Gly Gly Ala Gly Gly Tyr Ala Ser Asp Phe Val Gln
65                  70                  75                  80

Gly Ser Ser Ser Ala Ser Arg Glu Arg Lys Lys Gly Val Pro Trp Thr
                85                  90                  95

Glu Glu Glu His Arg Arg Phe Leu Leu Gly Leu Gln Lys Leu Gly Lys
                100                 105                 110

Gly Asp Trp Arg Gly Ile Ser Arg Asn Phe Val Val Ser Arg Thr Pro
            115                 120                 125

Thr Gln Val Ala Ser His Ala Gln Lys Tyr Phe Ile Arg Gln Ser Asn
        130                 135                 140

Met Ser Arg Arg Lys Arg Arg Ser Ser Leu Phe Asp Met Val Pro Asp
145                 150                 155                 160

Glu Ser Met Asp Leu Pro Pro Leu Pro Gly Ser Gln Glu Pro Glu Thr
                165                 170                 175

Ser Val Leu Asn Gln Ala Pro Leu Pro Pro Val Glu Glu Val
                180                 185                 190

Glu Ser Met Glu Ser Asp Thr Ser Ala Val Ala Glu Ser Ser Thr Ala
            195                 200                 205

Ser Ala Leu Met Pro Glu Ser Leu Gln Pro Asn Tyr Pro Met Ile Val
```

```
              210                 215                 220

Pro Ala Tyr Phe Ser Pro Phe Leu Gln Phe Ser Val Pro Phe Trp Pro
225                 230                 235                 240

Asn Gln Glu Asp Gly Gly Asp Leu Pro Gln Glu Thr His Glu Ile Val
                245                 250                 255

Lys Pro Val Ala Val His Ser Lys Asn Pro Ile Asn Val Asp Glu Leu
            260                 265                 270

Val Gly Met Ser Lys Leu Ser Ile Gly Glu Pro Gly Gln Glu Thr Val
        275                 280                 285

Ser Thr Ser Leu Ser Leu Asn Leu Leu Gly Gly Gln Asn Arg Gln Ser
    290                 295                 300

Ala Phe His Ala Asn Pro Gln Thr Arg Ala Gln Ala
305                 310                 315

<210> SEQ ID NO 53
<211> LENGTH: 1086
<212> TYPE: DNA
<213> ORGANISM: Sorghum bicolor

<400> SEQUENCE: 53
atgacgcgga ggtgctcgca ctgcagcaac aacggccaca actcgcgcac ctgccccgcc    60
cgctccggcg gcggggtgag gctatttggc gtgcgcctca acggcgcc ggctccggcg     120 gcgatgaaga gagcgccag catgagctgc atcgcgtcct cgctcggggg cgggtccggg    180
ggctcgtcgc cgccggcggg aggagtgggt ggtggcaggg gaggaggaga cggcggggcc    240
ggctacgtct ccgatgatcc cgggcacgcc tcctgctcga cgaatggccg cgtcgagcgg    300
aagaaaggta caccttggac tgaagaagag catagaatgt ttctgatggg tcttcagaag    360
cttggtaagg gagattggcg cgggatatct cgaaactttg ttgtttccag gaccccgact    420
caagtggcaa gccatgctca aaagtacttt attagacaga caaactcatc aagacggaag    480
aggcggtcaa gcttgtttga catggttgca gaaatgccag tagacgagtc cctagctgct    540
gcggaacaaa ttactatcca aaatactcaa gatgaagctg caagttcaaa tcaactgccg    600
accttacatc ttgggcatca gaaggaagca gagtttgcta agcaaatgcc aacttttcag    660
ctaaggcagc atgaggaatc tgaatatgca gaaccttcat tgacattacc agatttagag    720
atgaactcca gtgtaccatt caataccata gctgttccga cgatgccagc attctaccct    780
gcgttggtcc ctgttccact aactctttgg cctccaagtg ttgcccatgt ggaggacgca    840
ggcacaaccc atgaaatcct aaaccaact cctttgaatg gtaaggaggt gattaaagca    900
gatgatgttg ttggtatgtc taagctcagc attggtgagg ccagctctgg ctccatggaa    960
cccacagctc tttcccttca gcttattgga tcgacagata caaggcagtc agcttttcat   1020
gtgagtccac caatgaatag acctgaacta agcaagagaa acagcagtcc aattcatgcc   1080
gtttga                                                              1086

<210> SEQ ID NO 54
<211> LENGTH: 361
<212> TYPE: PRT
<213> ORGANISM: Sorghum bicolor

<400> SEQUENCE: 54

Met Thr Arg Arg Cys Ser His Cys Ser Asn Asn Gly His Asn Ser Arg
1               5                   10                  15

Thr Cys Pro Ala Arg Ser Gly Gly Gly Val Arg Leu Phe Gly Val Arg
            20                  25                  30
```

Leu Thr Thr Ala Pro Ala Pro Ala Met Lys Lys Ser Ala Ser Met
        35                  40                  45

Ser Cys Ile Ala Ser Ser Leu Gly Gly Gly Gly Gly Ser Ser Pro
    50                  55                  60

Pro Ala Gly Gly Val Gly Gly Arg Gly Gly Asp Gly Gly Ala
65                  70                  75                  80

Gly Tyr Val Ser Asp Asp Pro Gly His Ala Ser Cys Ser Thr Asn Gly
                85                  90                  95

Arg Val Glu Arg Lys Lys Gly Thr Pro Trp Thr Glu Glu His Arg
                100             105                 110

Met Phe Leu Met Gly Leu Gln Lys Leu Gly Lys Gly Asp Trp Arg Gly
            115                 120                 125

Ile Ser Arg Asn Phe Val Val Ser Arg Thr Pro Thr Gln Val Ala Ser
        130                 135                 140

His Ala Gln Lys Tyr Phe Ile Arg Gln Thr Asn Ser Ser Arg Arg Lys
145                 150                 155                 160

Arg Arg Ser Ser Leu Phe Asp Met Val Ala Glu Met Pro Val Asp Glu
                165                 170                 175

Ser Leu Ala Ala Ala Glu Gln Ile Thr Ile Gln Asn Thr Gln Asp Glu
            180                 185                 190

Ala Ala Ser Ser Asn Gln Leu Pro Thr Leu His Leu Gly His Gln Lys
        195                 200                 205

Glu Ala Glu Phe Ala Lys Gln Met Pro Thr Phe Gln Leu Arg Gln His
    210                 215                 220

Glu Glu Ser Glu Tyr Ala Glu Pro Ser Leu Thr Leu Pro Asp Leu Glu
225                 230                 235                 240

Met Asn Ser Ser Val Pro Phe Asn Thr Ile Ala Val Pro Thr Met Pro
                245                 250                 255

Ala Phe Tyr Pro Ala Leu Val Pro Val Pro Leu Thr Leu Trp Pro Pro
            260                 265                 270

Ser Val Ala His Val Glu Asp Ala Gly Thr Thr His Glu Ile Leu Lys
        275                 280                 285

Pro Thr Pro Leu Asn Gly Lys Glu Val Ile Lys Ala Asp Asp Val Val
    290                 295                 300

Gly Met Ser Lys Leu Ser Ile Gly Glu Ala Ser Ser Gly Ser Met Glu
305                 310                 315                 320

Pro Thr Ala Leu Ser Leu Gln Leu Ile Gly Ser Thr Asp Thr Arg Gln
                325                 330                 335

Ser Ala Phe His Val Ser Pro Pro Met Asn Arg Pro Glu Leu Ser Lys
            340                 345                 350

Arg Asn Ser Ser Pro Ile His Ala Val
        355                 360

<210> SEQ ID NO 55
<211> LENGTH: 1002
<212> TYPE: DNA
<213> ORGANISM: Glycine max

<400> SEQUENCE: 55
atgacgcggc gttgctcgca ttgcagccac aatgggcaca actcaagaac ttgccctaac      60
cgcggggtga agctcttcgg ggtccgatta accgatgggt cgatccggaa gagtgctagc     120
atgggcaatc taacccacta tgccggttcc gggtcgggtc cactccatac cgggttgaat     180
aaccccggtt cgcccgggga aaccccgat catgccgccg cagtcgccga cggttacttg      240

```
tccgaggact tcgttcccgg gtcttcttct agctcccgtg aaagaaagaa gggtgttcca    300
tggactgagg aggaacatag aatgttttta ctcggattgc agaagctggg caaaggtgat    360
tggcgtggaa ttgcaaggac ctatgttata tcaaggacac ctactcaagt ggctagccat    420
gctcagaaat atttcatcag gcagagcaat gtgtccaggc ggaaaagacg gtccagcttg    480
tttgatattg ttgcagatga agcagctgac actgcaatgg tacagcaaga cttcttgtct    540
gctaatcagt tacccactga aacagaaggc aataacccct tgccagctcc tcctcccctc    600
gacgaagagt gcgaatccat ggattccaca aactcaaatg atggagagcc tgccccatca    660
aagccagaaa acacacagtc atcttatcca atgttatatc ctgcatatta ttctccggtg    720
ttcccgtttc tctgcccta ttggtcagga tacagtccag agtccaccaa gaaggaggag    780
acacatgaag tactgaagcc aactgcagtt cattctaaaa gccctatcaa tgttgatgaa    840
ctggttggca tttcaaaatt gagtttaggg gagtctattg gtgactctgg tccctcctct    900
ctgtctcgaa aacttatcga agaaggaccc tctagacagt cagcttttca tgcaacaccg    960
acatgtggca gttcaaatgg cagtgccatc catgcagttt aa                      1002
```

<210> SEQ ID NO 56
<211> LENGTH: 333
<212> TYPE: PRT
<213> ORGANISM: Glycine max

<400> SEQUENCE: 56

```
Met Thr Arg Arg Cys Ser His Cys Ser His Asn Gly His Asn Ser Arg
1               5                   10                  15

Thr Cys Pro Asn Arg Gly Val Lys Leu Phe Gly Val Arg Leu Thr Asp
            20                  25                  30

Gly Ser Ile Arg Lys Ser Ala Ser Met Gly Asn Leu Thr His Tyr Ala
        35                  40                  45

Gly Ser Gly Ser Gly Pro Leu His Thr Gly Leu Asn Asn Pro Gly Ser
    50                  55                  60

Pro Gly Glu Thr Pro Asp His Ala Ala Ala Val Ala Asp Gly Tyr Leu
65                  70                  75                  80

Ser Glu Asp Phe Val Pro Gly Ser Ser Ser Ser Arg Glu Arg Lys
                85                  90                  95

Lys Gly Val Pro Trp Thr Glu Glu His Arg Met Phe Leu Leu Gly
            100                 105                 110

Leu Gln Lys Leu Gly Lys Gly Asp Trp Arg Gly Ile Ala Arg Thr Tyr
        115                 120                 125

Val Ile Ser Arg Thr Pro Thr Gln Val Ala Ser His Ala Gln Lys Tyr
    130                 135                 140

Phe Ile Arg Gln Ser Asn Val Ser Arg Lys Arg Ser Ser Leu
145                 150                 155                 160

Phe Asp Ile Val Ala Asp Glu Ala Ala Asp Thr Ala Met Val Gln Gln
                165                 170                 175

Asp Phe Leu Ser Ala Asn Gln Leu Pro Thr Glu Thr Glu Gly Asn Asn
            180                 185                 190

Pro Leu Pro Ala Pro Pro Leu Asp Glu Glu Cys Glu Ser Met Asp
        195                 200                 205

Ser Thr Asn Ser Asn Asp Gly Glu Pro Ala Pro Ser Lys Pro Glu Asn
    210                 215                 220

Thr Gln Ser Ser Tyr Pro Met Leu Tyr Pro Ala Tyr Tyr Ser Pro Val
225                 230                 235                 240
```

Phe Pro Phe Pro Leu Pro Tyr Trp Ser Gly Tyr Ser Pro Glu Ser Thr
                245                 250                 255

Lys Lys Glu Glu Thr His Glu Val Leu Lys Pro Thr Ala Val His Ser
            260                 265                 270

Lys Ser Pro Ile Asn Val Asp Glu Leu Val Gly Ile Ser Lys Leu Ser
        275                 280                 285

Leu Gly Glu Ser Ile Gly Asp Ser Gly Pro Ser Ser Leu Ser Arg Lys
    290                 295                 300

Leu Ile Glu Glu Gly Pro Ser Arg Gln Ser Ala Phe His Ala Thr Pro
305                 310                 315                 320

Thr Cys Gly Ser Ser Asn Gly Ser Ala Ile His Ala Val
                325                 330

<210> SEQ ID NO 57
<211> LENGTH: 1002
<212> TYPE: DNA
<213> ORGANISM: Glycine max

<400> SEQUENCE: 57
atgacgcggc gttgctcgca ttgcagccac aatgggcaca actccagaac ctgccctaac      60
cgcggggtta agctcttcgg ggtccgatta accgacgggt cgatccggaa gagcgccagc     120
atgggcaacc taaccccacta cgctggttcc gggtcggccc cgctccatgt cgggttgaat     180
aacccgggtt cacccgggga cgcccgat cacgccgccg ccgccgccga cggctacgcc      240
tccgaggact cgttcccgg gtcttcttct agctcccgtg aaagaaagaa gggtgttcca      300
tggactgagg aggaacatag aatgttttg ctcggattgc agaagctggg caaaggtgat     360
tggcgtggaa ttgcaaggaa ctatgttata tcaaggacgc ctactcaagt ggccagccat     420
gctcagaaat atttcatcag gcaaagcaat gtgtccaggc gaaaagacg gtccagcttg     480
tttgatattg ttgcagatga agcagctgac actgcaatgg tacagcaaga cttcttgtct     540
gctaatgagt taccaactga aacagaaggc aataacccct gcctgctcc tcctcccctc     600
gatgaagagt gtgaatcaat ggattccaca aactcaaatg atggagagcc tgccccatca     660
aagccagaaa acacacatcc atcttatcct atgttatatc ctgcgtatta ttctccagtg     720
ttcccgtttc ctctgcccta ttggtcagga tacagtccag agcccaccaa gaaggaggaa      780
acacatgaag tgctgaaacc aactgcagta cattctaaaa gccctatcaa tgttgatgaa      840
ctggttggca tatcaaaact gagtttaggg gagtctattg gtgactcggg tccctccacc      900
ctgtctcgaa aacttattga agaaggaccc tctagacaat cagctttttca tgcaacacca      960
acatgtggtg atatgaatgg cagtgccatc catgcagttt aa                         1002

<210> SEQ ID NO 58
<211> LENGTH: 333
<212> TYPE: PRT
<213> ORGANISM: Glycine max

<400> SEQUENCE: 58

Met Thr Arg Arg Cys Ser His Cys Ser His Asn Gly His Asn Ser Arg
1               5                  10                  15

Thr Cys Pro Asn Arg Gly Val Lys Leu Phe Gly Val Arg Leu Thr Asp
            20                  25                  30

Gly Ser Ile Arg Lys Ser Ala Ser Met Gly Asn Leu Thr His Tyr Ala
        35                  40                  45

Gly Ser Gly Ser Ala Pro Leu His Val Gly Leu Asn Asn Pro Gly Ser

```
                    50                  55                  60
Pro Gly Glu Thr Pro Asp His Ala Ala Ala Ala Asp Gly Tyr Ala
 65                  70                  75                  80

Ser Glu Asp Phe Val Pro Gly Ser Ser Ser Ser Arg Glu Arg Lys
                     85                  90                  95

Lys Gly Val Pro Trp Thr Glu Glu His Arg Met Phe Leu Leu Gly
                100                 105                 110

Leu Gln Lys Leu Gly Lys Gly Asp Trp Arg Gly Ile Ala Arg Asn Tyr
                115                 120                 125

Val Ile Ser Arg Thr Pro Thr Gln Val Ala Ser His Ala Gln Lys Tyr
                130                 135                 140

Phe Ile Arg Gln Ser Asn Val Ser Arg Arg Lys Arg Arg Ser Ser Leu
145                 150                 155                 160

Phe Asp Ile Val Ala Asp Glu Ala Ala Asp Thr Ala Met Val Gln Gln
                165                 170                 175

Asp Phe Leu Ser Ala Asn Glu Leu Pro Thr Glu Thr Glu Gly Asn Asn
                180                 185                 190

Pro Leu Pro Ala Pro Pro Leu Asp Glu Glu Cys Glu Ser Met Asp
                195                 200                 205

Ser Thr Asn Ser Asn Asp Gly Glu Pro Ala Pro Ser Lys Pro Glu Asn
                210                 215                 220

Thr His Pro Ser Tyr Pro Met Leu Tyr Pro Ala Tyr Tyr Ser Pro Val
225                 230                 235                 240

Phe Pro Phe Pro Leu Pro Tyr Trp Ser Gly Tyr Ser Pro Glu Pro Thr
                245                 250                 255

Lys Lys Glu Glu Thr His Glu Val Leu Lys Pro Thr Ala Val His Ser
                260                 265                 270

Lys Ser Pro Ile Asn Val Asp Glu Leu Val Gly Ile Ser Lys Leu Ser
                275                 280                 285

Leu Gly Glu Ser Ile Gly Asp Ser Gly Pro Ser Thr Leu Ser Arg Lys
                290                 295                 300

Leu Ile Glu Glu Gly Pro Ser Arg Gln Ser Ala Phe His Ala Thr Pro
305                 310                 315                 320

Thr Cys Gly Asp Met Asn Gly Ser Ala Ile His Ala Val
                325                 330

<210> SEQ ID NO 59
<211> LENGTH: 1008
<212> TYPE: DNA
<213> ORGANISM: Vitis vinifera

<400> SEQUENCE: 59
atgactcgcc gctgctcgca ttgcagtcac aacgggcaca attccaggac atgccccaac      60
cgcggggtca agatcttcgg ggttcgattg actgatgggt tgatccgtaa gagtgctagt     120
atgggcaatc tcagccacta cgccgggtcg acctctggtc atcatcagaa cggcgtttcc     180
ggtaacaatt cggtctctcc cggagagact ccagagcacg gcgccgcggc cgatggatac     240
gcctccgagg gtttcgttcc cggttcatca tccagccggg agcgcaagaa aggcactcca     300
tggactgaag aggaacacag aatgtttcta cttggactgc agaagcttgg aaaagggggat    360 tggcgtggaa tttcacgtaa ttatgttata tcaaggacac ctactcaagt cgccagccat     420
gctcagaaat atttcatcag gcaaactaat gtgtctagga gaaaaagacg gtccagcttg     480
tttgatattg tagctgatga atctgtcgac actccaatgg tatcacggga tttcttctcc     540
```

```
accaacccttt cgcaagctga acactaagc aataacccat tgcctgttcc tccggctctg    600
gatgaagaat gtgaatcaat ggattctacc aactcgaatg atggagaacc gcccattcca    660
aagccggatg gcttacaagg ctgtcccca gtaatatatc ctacttattt ctcaccattc     720
ttcccatttt cttttccatt ctggccggga acagttcag agccaactaa atggagact     780 catgaggtgc ttaagccaac agctgtacat tctaagagtc caatcaatgt tgatgagctg    840
gttggcatgt caaaactgag tttaggagaa tccatcggtc atgctggtcc ctcctctctc    900
acactgaaac tgcttgaagg gtcaagcagg caatctgctt tccatgctaa tccagcctct    960
ggcagttcaa gcatgaactc gagcggcagt ccaatccatg cagtttga              1008
```

<210> SEQ ID NO 60
<211> LENGTH: 335
<212> TYPE: PRT
<213> ORGANISM: Vitis vinifera

<400> SEQUENCE: 60

```
Met Thr Arg Arg Cys Ser His Cys Ser His Asn Gly His Asn Ser Arg
1               5                   10                  15

Thr Cys Pro Asn Arg Gly Val Lys Ile Phe Gly Val Arg Leu Thr Asp
            20                  25                  30

Gly Leu Ile Arg Lys Ser Ala Ser Met Gly Asn Leu Ser His Tyr Ala
        35                  40                  45

Gly Ser Thr Ser Gly His His Gln Asn Gly Val Ser Gly Asn Asn Ser
    50                  55                  60

Val Ser Pro Gly Glu Thr Pro Glu His Gly Ala Ala Ala Asp Gly Tyr
65                  70                  75                  80

Ala Ser Glu Gly Phe Val Pro Gly Ser Ser Ser Arg Glu Arg Lys
            85                  90                  95

Lys Gly Thr Pro Trp Thr Glu Glu His Arg Met Phe Leu Leu Gly
            100                 105                 110

Leu Gln Lys Leu Gly Lys Gly Asp Trp Arg Gly Ile Ser Arg Asn Tyr
        115                 120                 125

Val Ile Ser Arg Thr Pro Thr Gln Val Ala Ser His Ala Gln Lys Tyr
130                 135                 140

Phe Ile Arg Gln Thr Asn Val Ser Arg Arg Lys Arg Arg Ser Ser Leu
145                 150                 155                 160

Phe Asp Ile Val Ala Asp Glu Ser Val Asp Thr Pro Met Val Ser Arg
                165                 170                 175

Asp Phe Phe Ser Thr Asn Pro Ser Gln Ala Glu Thr Leu Ser Asn Asn
            180                 185                 190

Pro Leu Pro Val Pro Pro Ala Leu Asp Glu Glu Cys Glu Ser Met Asp
        195                 200                 205

Ser Thr Asn Ser Asn Asp Gly Glu Pro Pro Ile Pro Lys Pro Asp Gly
    210                 215                 220

Leu Gln Gly Cys Pro Pro Val Ile Tyr Pro Thr Tyr Phe Ser Pro Phe
225                 230                 235                 240

Phe Pro Phe Ser Phe Pro Phe Trp Pro Gly Asn Ser Ser Glu Pro Thr
                245                 250                 255

Lys Met Glu Thr His Glu Val Leu Lys Pro Thr Ala Val His Ser Lys
            260                 265                 270

Ser Pro Ile Asn Val Asp Glu Leu Val Gly Met Ser Lys Leu Ser Leu
        275                 280                 285

Gly Glu Ser Ile Gly His Ala Gly Pro Ser Ser Leu Thr Leu Lys Leu
```

```
                290                 295                 300
Leu Glu Gly Ser Ser Arg Gln Ser Ala Phe His Ala Asn Pro Ala Ser
305                 310                 315                 320

Gly Ser Ser Ser Met Asn Ser Ser Gly Ser Pro Ile His Ala Val
                325                 330                 335
```

<210> SEQ ID NO 61
<211> LENGTH: 1038
<212> TYPE: DNA
<213> ORGANISM: Vitis vinifera

<400> SEQUENCE: 61

```
atgactcgcc gctgctcgca ttgcagtcac aacgggcaca attccaggac atgccccaac      60
cgcggggtca agatcttcgg ggttcgattg actgatgggt tgatccgtaa gagtgctagt     120
atgggcaatc tcagccacta cgccgggtcg acctctggtc atcatcagaa cggcgtttcc     180
ggtaacaatt cggtctctcc cggagagact ccagagcacg gcgccgcggc cgatggatac     240
gcctccgagg gtttcgttcc cggttcatca tccagccggg agcgcaagaa aggcactcca     300
tggactgaag aggaacacag aatgtttcta cttggactgc agaagcttgg aaaaggggat     360
tggcgtggaa tttcacgtaa ttatgttata tcaaggacac tactcaagt cgccagccat     420
gctcagaaat atttcatcag gcaaaccaat gtgtctagga gaaaaagacg gtccagcttg     480
tttgatattg tagctgatga atctgttgac actccaatgg tatcacggga tttcttctcc     540
accaacccct tcgcaagctga aacactaagc aataacccat gcctgttcc tccggctctg     600
gatgaagaat gtgaatcaat ggattctacc aactcgaatg atggagaacc acccattcca     660
aagccggatg gcttacaagg ctgtccccca gtaatatatc ctacttattt ctcgccattc     720
ttcccatttt cttttccatt ctggccggga acagttcag agccaactaa aatggagact     780
catgaggtgc ttaagccaac agctgtacat tctaagagtc aatcaatgt tgatgagctg     840
gttggcatgt caaaactgag tttaggagaa tccatcggtc atgctggtcc ctcctctctc     900
acactgaaac tgcttgaagg gtcaagcagg caatctgctt tccatgctaa tccagcctct     960
ggcagttcaa gcatgaactc gagcggcagt ccaatccatg cacccaatgg gaagattctg    1020
ctggtatgga gattgtag                                                  1038
```

<210> SEQ ID NO 62
<211> LENGTH: 345
<212> TYPE: PRT
<213> ORGANISM: Vitis vinifera

<400> SEQUENCE: 62

```
Met Thr Arg Arg Cys Ser His Cys Ser His Asn Gly His Asn Ser Arg
1               5                   10                  15

Thr Cys Pro Asn Arg Gly Val Lys Ile Phe Gly Val Arg Leu Thr Asp
            20                  25                  30

Gly Leu Ile Arg Lys Ser Ala Ser Met Gly Asn Leu Ser His Tyr Ala
        35                  40                  45

Gly Ser Thr Ser Gly His His Gln Asn Gly Val Ser Gly Asn Asn Ser
    50                  55                  60

Val Ser Pro Gly Glu Thr Pro Glu His Gly Ala Ala Asp Gly Tyr
65                  70                  75                  80

Ala Ser Glu Gly Phe Val Pro Gly Ser Ser Ser Arg Glu Arg Lys
                85                  90                  95

Lys Gly Thr Pro Trp Thr Glu Glu Glu His Arg Met Phe Leu Leu Gly
```

```
            100             105             110
Leu Gln Lys Leu Gly Lys Gly Asp Trp Arg Gly Ile Ser Arg Asn Tyr
            115             120             125

Val Ile Ser Arg Thr Pro Thr Gln Val Ala Ser His Ala Gln Lys Tyr
            130             135             140

Phe Ile Arg Gln Thr Asn Val Ser Arg Arg Lys Arg Ser Ser Leu
145             150             155             160

Phe Asp Ile Val Ala Asp Glu Ser Val Asp Thr Pro Met Val Ser Arg
            165             170             175

Asp Phe Phe Ser Thr Asn Pro Ser Gln Ala Glu Thr Leu Ser Asn Asn
            180             185             190

Pro Leu Pro Val Pro Pro Ala Leu Asp Glu Glu Cys Glu Ser Met Asp
            195             200             205

Ser Thr Asn Ser Asn Asp Gly Glu Pro Pro Ile Pro Lys Pro Asp Gly
            210             215             220

Leu Gln Gly Cys Pro Pro Val Ile Tyr Pro Thr Tyr Phe Ser Pro Phe
225             230             235             240

Phe Pro Phe Ser Phe Pro Phe Trp Pro Gly Asn Ser Ser Glu Pro Thr
            245             250             255

Lys Met Glu Thr His Glu Val Leu Lys Pro Thr Ala Val His Ser Lys
            260             265             270

Ser Pro Ile Asn Val Asp Glu Leu Val Gly Met Ser Lys Leu Ser Leu
            275             280             285

Gly Glu Ser Ile Gly His Ala Gly Pro Ser Ser Leu Thr Leu Lys Leu
            290             295             300

Leu Glu Gly Ser Ser Arg Gln Ser Ala Phe His Ala Asn Pro Ala Ser
305             310             315             320

Gly Ser Ser Ser Met Asn Ser Ser Gly Ser Pro Ile His Ala Pro Asn
            325             330             335

Gly Lys Ile Leu Leu Val Trp Arg Leu
            340             345
```

<210> SEQ ID NO 63
<211> LENGTH: 1011
<212> TYPE: DNA
<213> ORGANISM: Lotus japonicus

<400> SEQUENCE: 63

```
atgacccggc gatgctcgca ttgcagccat ggtggccaca cgccaggac ctgccccaac      60
cgcggagtca agcttttcgg tgtccgattg actgatggct cgatccggaa gagtgctagt    120
atgggtaatc tcacccacta cactggctcc gggtctggac ctcttcttgg tgggtccaat    180
aaccctgatt ctcccggtga aaccctgat cacgccgccg ctgctgacgg ttacgcctct    240
gaggattttg ttcctggctc ttcttctagc tcccgtgaaa gaaaaaaggg cactccatgg    300
actgaggagg aacacagaat gttttactt ggattgcaga actgggcaa aggtgattgg    360
cgtggaattg caaggaacta tgttatttca aggacaccta ctcaagtggc cagtcatgct    420
cagaaatatt tcatcaggca aagcaatgtg tctaggagaa agagacggtc cagcttgttt    480
gatattgttg cagatgatgc gtccgacact ccaatggtag agcaagactt cttgtcagct    540
aatcagctac agactgaaac agaaggcaat aaccctttgc ctgctcctcc tcccattgat    600
gaagagtgtg aatccatgga ttccacaaac tcaatagatg gagactctgc cctgttaaag    660
cccgacactc caataccgcc aacctaccgc gtgttatatc ctgcatatta tcctccattc    720
```

```
taccccgtatc ctctgcctta ttggtctgga tacagtcctg cagagccccc aaagaaagag      780
gagacacatg aagtggtgaa gccaactgcg gtgctttcca aaagcccaat caatgtggat      840
gaacttgtcg gcatgtcaaa actgagtttg ggagactcca ttggtgactc tggcccctcc      900
tctctgtctc gaaaactcgt cgaagaagga ccttccagac aatcagcttt tcatgctact      960
ccagcatgtg gcagttcaaa tataaatggc agtgtcatac atgcagttta a              1011
```

<210> SEQ ID NO 64
<211> LENGTH: 336
<212> TYPE: PRT
<213> ORGANISM: Lotus japonicus

<400> SEQUENCE: 64

```
Met Thr Arg Arg Cys Ser His Cys Ser His Gly Gly His Asn Ala Arg
1               5                   10                  15

Thr Cys Pro Asn Arg Gly Val Lys Leu Phe Gly Val Arg Leu Thr Asp
                20                  25                  30

Gly Ser Ile Arg Lys Ser Ala Ser Met Gly Asn Leu Thr His Tyr Thr
            35                  40                  45

Gly Ser Gly Ser Gly Pro Leu Leu Gly Gly Ser Asn Asn Pro Asp Ser
        50                  55                  60

Pro Gly Glu Thr Pro Asp His Ala Ala Ala Asp Gly Tyr Ala Ser
65                  70                  75                  80

Glu Asp Phe Val Pro Gly Ser Ser Ser Ser Arg Glu Arg Lys Lys
                85                  90                  95

Gly Thr Pro Trp Thr Glu Glu His Arg Met Phe Leu Leu Gly Leu
            100                 105                 110

Gln Lys Leu Gly Lys Gly Asp Trp Arg Gly Ile Ala Arg Asn Tyr Val
        115                 120                 125

Ile Ser Arg Thr Pro Thr Gln Val Ala Ser His Ala Gln Lys Tyr Phe
    130                 135                 140

Ile Arg Gln Ser Asn Val Ser Arg Arg Lys Arg Ser Ser Leu Phe
145                 150                 155                 160

Asp Ile Val Ala Asp Ala Ser Asp Thr Pro Met Val Glu Gln Asp
                165                 170                 175

Phe Leu Ser Ala Asn Gln Leu Gln Thr Glu Thr Glu Gly Asn Asn Pro
            180                 185                 190

Leu Pro Ala Pro Pro Ile Asp Glu Glu Cys Glu Ser Met Asp Ser
        195                 200                 205

Thr Asn Ser Ile Asp Gly Asp Ser Ala Leu Leu Lys Pro Asp Thr Pro
    210                 215                 220

Ile Pro Pro Thr Tyr Pro Val Leu Tyr Pro Ala Tyr Tyr Pro Phe
225                 230                 235                 240

Tyr Pro Tyr Pro Leu Pro Tyr Trp Ser Gly Tyr Ser Pro Ala Glu Pro
                245                 250                 255

Pro Lys Lys Glu Glu Thr His Glu Val Val Lys Pro Thr Ala Val Leu
            260                 265                 270

Ser Lys Ser Pro Ile Asn Val Asp Glu Leu Val Gly Met Ser Lys Leu
        275                 280                 285

Ser Leu Gly Asp Ser Ile Gly Asp Ser Gly Pro Ser Ser Leu Ser Arg
    290                 295                 300

Lys Leu Val Glu Glu Gly Pro Ser Arg Gln Ser Ala Phe His Ala Thr
305                 310                 315                 320

Pro Ala Cys Gly Ser Ser Asn Ile Asn Gly Ser Val Ile His Ala Val
```

<210> SEQ ID NO 65
<211> LENGTH: 927
<212> TYPE: DNA
<213> ORGANISM: Lotus japonicus

<400> SEQUENCE: 65

```
atgtctcgca cgtgctcaca gtgcggcaac aacggccaca actcccgcac atgcaccgac    60
accgccgccg ctggagacaa cggcatcatg ctcttcggcg tgcgcctcac cgaaggctcc   120
acctcctcct ccgccttcat caggaagagc gctagcatga caacctctcc cagtataac   180
gaacccgaat ccaaccccgc tgacgcagct ggctacgcct ccgacgacgt cgttcatccc   240
tccgcacgcg cccgcgaccg caagcgaggt gtgccttgga cggaagaaga acacaaactg   300
tttctgttgg gattgcataa agtggggaag ggagattgga gaggaatttc tagaaacttc   360
gtcaaaactc gcacacccac tcaggttgct agtcatgctc agaagtattt cctccgccgt   420
cacaaccata accgccggcg ccggagatct agccttttcg acatcaccac cgatacggtg   480
atggaatctt caacaataat ggaggaagaa caagatcagc aagaaatggt gccgccagct   540
acctccgccg tgtatccgcc gttacattac ggtggcttcc acggcccagc gtttccaatg   600
gctctgtctc cggtggtatt gccggtggcc ggaggggaaa gaccggcaag gccgattagg   660
ccaacgccga ttttccctgt gcctccgtct tctaagatgg ctagtttgaa cttgaaagag   720
aaagcagctt ctccttcccc ttcttctcca tttgagcctc taccgctgtc gctgaagctg   780
cagccatctc cgccgccgtc caaggatcat tctccggcaa ccagtagcca ctcgtcgcca   840
tcatcgccgt cttcttcatc atcttttcag gctatgtctg cagggaagtt cagcggtggt   900
ggagatagca ttattagtgt tgcttga                                       927
```

<210> SEQ ID NO 66
<211> LENGTH: 308
<212> TYPE: PRT
<213> ORGANISM: Lotus japonicus

<400> SEQUENCE: 66

```
Met Ser Arg Thr Cys Ser Gln Cys Gly Asn Asn Gly His Asn Ser Arg
1               5                   10                  15

Thr Cys Thr Asp Thr Ala Ala Ala Gly Asp Asn Gly Ile Met Leu Phe
            20                  25                  30

Gly Val Arg Leu Thr Glu Gly Ser Thr Ser Ser Ala Phe Ile Arg
        35                  40                  45

Lys Ser Ala Ser Met Asn Asn Leu Ser Gln Tyr Asn Glu Pro Glu Ser
    50                  55                  60

Asn Pro Ala Asp Ala Ala Gly Tyr Ala Ser Asp Val Val His Pro
65                  70                  75                  80

Ser Ala Arg Ala Arg Asp Arg Lys Arg Gly Val Pro Trp Thr Glu Glu
                85                  90                  95

Glu His Lys Leu Phe Leu Leu Gly Leu His Lys Val Gly Lys Gly Asp
            100                 105                 110

Trp Arg Gly Ile Ser Arg Asn Phe Val Lys Thr Arg Thr Pro Thr Gln
        115                 120                 125

Val Ala Ser His Ala Gln Lys Tyr Phe Leu Arg Arg His Asn His Asn
    130                 135                 140

Arg Arg Arg Arg Arg Ser Ser Leu Phe Asp Ile Thr Thr Asp Thr Val
145                 150                 155                 160
```

```
Met Glu Ser Ser Thr Ile Met Glu Glu Glu Gln Asp Gln Gln Glu Met
                165                 170                 175

Val Pro Pro Ala Thr Ser Ala Val Tyr Pro Pro Leu His Tyr Gly Gly
            180                 185                 190

Phe His Gly Pro Ala Phe Pro Met Ala Leu Ser Pro Val Val Leu Pro
        195                 200                 205

Val Ala Gly Gly Glu Arg Pro Ala Arg Pro Ile Arg Pro Thr Pro Ile
    210                 215                 220

Phe Pro Val Pro Pro Ser Ser Lys Met Ala Ser Leu Asn Leu Lys Glu
225                 230                 235                 240

Lys Ala Ala Ser Pro Ser Pro Ser Ser Pro Phe Glu Pro Leu Pro Leu
                245                 250                 255

Ser Leu Lys Leu Gln Pro Ser Pro Pro Pro Ser Lys Asp His Ser Pro
            260                 265                 270

Ala Thr Ser Ser His Ser Ser Pro Ser Ser Pro Ser Ser Ser Ser Ser
        275                 280                 285

Phe Gln Ala Met Ser Ala Gly Lys Phe Ser Gly Gly Gly Asp Ser Ile
    290                 295                 300

Ile Ser Val Ala
305
```